US011155817B2

(12) United States Patent
Davidson et al.

(10) Patent No.: US 11,155,817 B2
(45) Date of Patent: Oct. 26, 2021

(54) THERAPEUTIC FOR TREATMENT OF DISEASES INCLUDING THE CENTRAL NERVOUS SYSTEM

(71) Applicant: The Children's Hospital of Philadelphia, Philadelphia, PA (US)

(72) Inventors: Beverly L. Davidson, Philadelphia, PA (US); Alejandro Mas Monteys, Philadelphia, PA (US); Megan S. Keiser, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 275 days.

(21) Appl. No.: 16/085,504

(22) PCT Filed: Mar. 17, 2017

(86) PCT No.: PCT/US2017/022973
§ 371 (c)(1),
(2) Date: Sep. 14, 2018

(87) PCT Pub. No.: WO2017/161273
PCT Pub. Date: Sep. 21, 2017

(65) Prior Publication Data
US 2019/0071671 A1 Mar. 7, 2019

Related U.S. Application Data

(60) Provisional application No. 62/310,229, filed on Mar. 18, 2016, provisional application No. 62/367,858, filed on Jul. 28, 2016.

(51) Int. Cl.
| | | |
|---|---|---|
| *C12N 15/113* | (2010.01) | |
| *C12N 15/86* | (2006.01) | |
| *A61K 35/76* | (2015.01) | |
| *C12N 7/00* | (2006.01) | |
| *A61P 25/28* | (2006.01) | |
| *A61K 9/00* | (2006.01) | |

(52) U.S. Cl.
CPC .......... *C12N 15/113* (2013.01); *A61K 9/0085* (2013.01); *A61K 35/76* (2013.01); *A61P 25/28* (2018.01); *C12N 7/00* (2013.01); *C12N 15/86* (2013.01); *C12N 2310/11* (2013.01); *C12N 2310/14* (2013.01); *C12N 2310/141* (2013.01); *C12N 2320/35* (2013.01); *C12N 2330/51* (2013.01); *C12N 2750/14122* (2013.01); *C12N 2750/14142* (2013.01); *C12N 2750/14143* (2013.01); *C12N 2750/14152* (2013.01); *C12N 2750/14171* (2013.01)

(58) Field of Classification Search
CPC .................................................. C12N 15/113
See application file for complete search history.

(56) References Cited

FOREIGN PATENT DOCUMENTS

| | | | | |
|---|---|---|---|---|
| WO | 2014/007858 A1 | 1/2014 | | |
| WO | WO-2014007858 A1 | * 1/2014 | .............. | A61P 43/00 |
| WO | 2014/144486 A2 | 9/2014 | | |
| WO | WO-2014144486 A2 | * 9/2014 | ......... | A61K 48/0025 |
| WO | 2016/196507 A1 | 12/2016 | | |

OTHER PUBLICATIONS

Lye et al., 1996, Exp. Parasitology, vol. 82, pp. 211-217) (Year: 1996).*
Choi et al. (2014, Molecular Brain, vol. 7(17), pp. 1-10) (Year: 2014).*
Bec et al. (2006, Gene Therapy, vol. 13, pp. 805-813). (Year: 2006).*
Dong et al., Characterization of Genome Integrity for Oversized Recombinant AAV Vector, Molecular Therapy, Nov. 10, 2009, 18(1):87-92.
Grieger, et al., Packaging Capacity of Adeno-Associated Virus Serotypes: Impact of Larger Genomes on Infectivity and Postentry Steps, Journal of Virology, Aug. 1, 2005, 79(15):9933-9944.
Keiser, M. et al., Broad distribution of ataxin 1 silencing in rhesus cerebella for spinocerebellar ataxia type 1 therapy, Oct. 21, 2015, Brain, 138(12):3555-3566.
Keiser, M.S., et al., RNAi prevents and reverses phenotypes induced by mutant human ataxin-1, Annals of Neurology, Nov. 1, 2016, 80(5):754-765.
Mas Monteys, A., et al., Single nucleotide seed modification restores in vivo tolerability of a toxic artificial miRNA sequence in the mouse brain, Nucleic Acids Research, Oct. 20, 2014, 42(21):13315-13327.
Wu, et al., Effect of genome size on AAV vector packaging, Molecular Therapy, Nov. 10, 2009, 18(1):80-86.

* cited by examiner

*Primary Examiner* — Thaian N. Ton
*Assistant Examiner* — David A Montanari
(74) *Attorney, Agent, or Firm* — Pillsbury Winthrop Shaw Pittman LLP; Robert M. Bedgood

(57) ABSTRACT

The present disclosure provides filler or stuffer sequences, compositions thereof including expression cassettes and vectors, such as viral (e.g., AAV) vectors and methods of delivering a therapeutic agent to a mammal and/or treating a disease.

19 Claims, 7 Drawing Sheets
Specification includes a Sequence Listing.

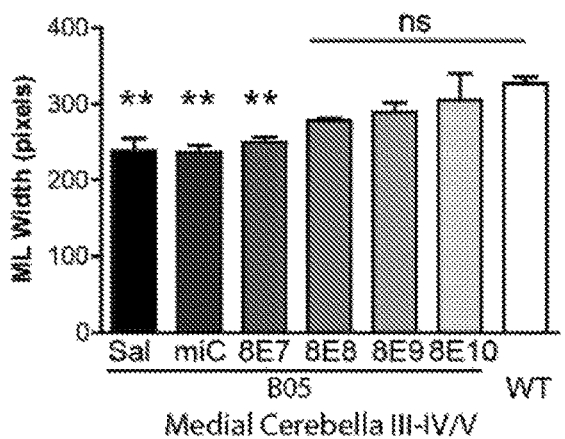
FIG. 3A
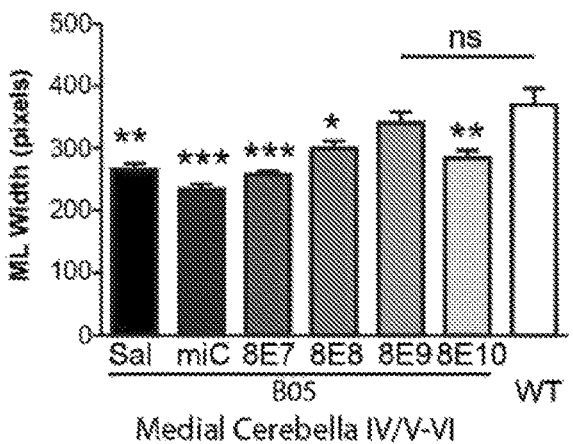
FIG. 3B
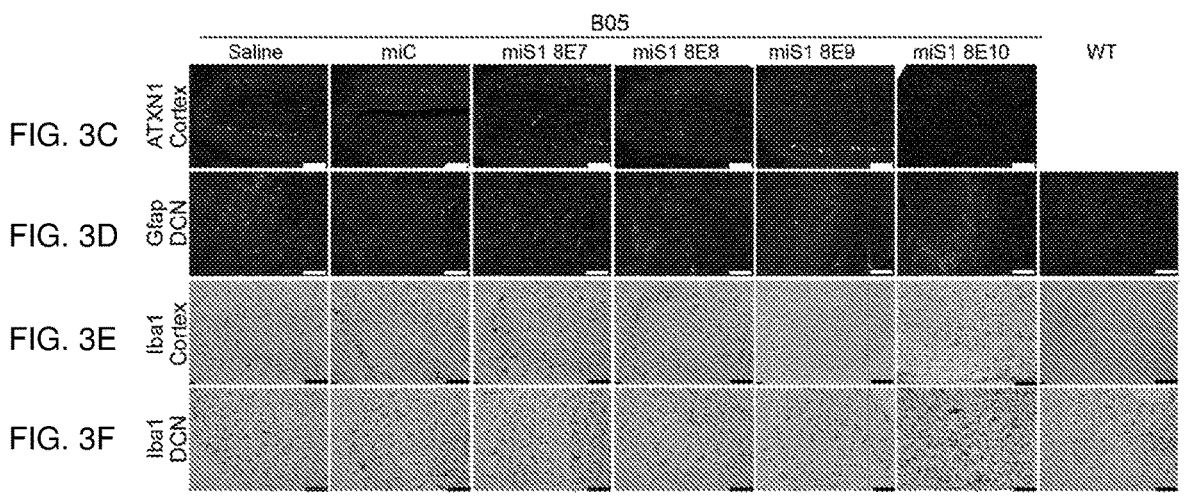
FIG. 3C
FIG. 3D
FIG. 3E
FIG. 3F

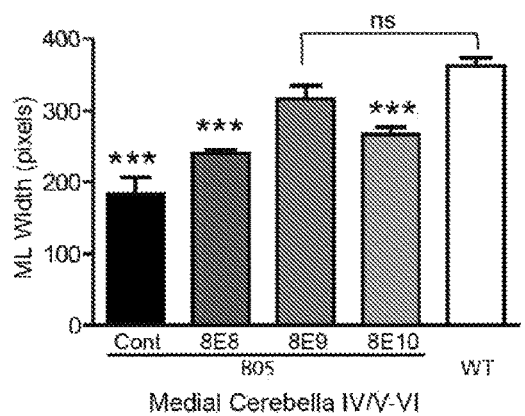
FIG. 6A
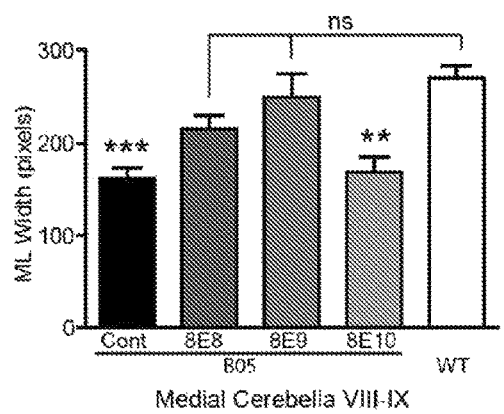
FIG. 6B
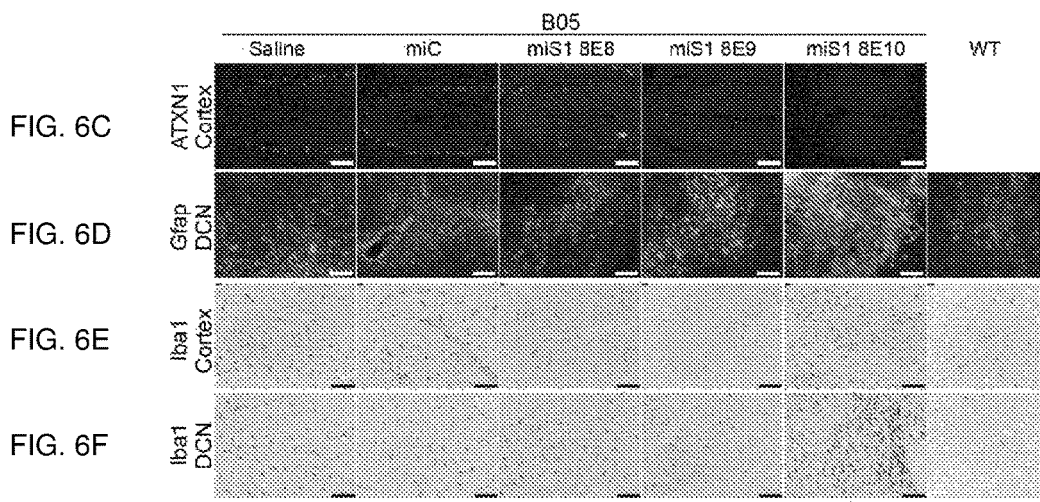
FIG. 6C
FIG. 6D
FIG. 6E
FIG. 6F

SEQUENCE LISTING

<160> NUMBER OF SEQ ID NOS: 8

<210> SEQ ID NO 1
<211> LENGTH: 3774
<212> TYPE: DNA
<213> ORGANISM: Artificial Sequence
<220> FEATURE:
<223> OTHER INFORMATION: Description of Artificial Sequence: Stuffer
      Sequence

<400> SEQUENCE: 1

```
gaattcaggc tatcccaggt tgccttggtt cttggcaatt gggaaattaa gagggcagag      60
agaatttgaa cagaaactgt tctaatattg gtcttttatt gtgtaagtat tgttctttgg     120
taaacctcct tcttttggtt tccaggaatt gctggacaca gtggcttggt gtgtgtctga     180
```

```
ggactgtagg ccttggccct aggttgtggt tttaggtctc aggtgctctt cctggctgtc      240
tccttgcttc tttcccttgt cctcttcttt gtttccagcc tttctccct tttgcttaag       300 tttggtgcag cagggtttgg ctgctctcag attcctgctt cctcagttgc tgtagttgtc      360
aggcccagaa ggctggcaga aggatcagga tctggctagg tttgctctca ctgtggcaga      420 gtaggggag gaggagagca aaagtgaccc caggccagct gtagggagct taggcttggt       480
caaccagcct tcaggtccta gactttgtct tctcttgagt ttggctgtgt gtgtttggtg      540
ggaactaggt tctacttagc ccaagaaatt gggcactttt tgcttgtggt ttctgtagag      600
aattgcactg ggtatctgac ttagcctggc agcttgcctc cctcaggtag gttagtctca      660
ggaagtgaag caaagtccag caagaacttc ttttgtggct taaagtctca attctgtgag      720
gtgctggcaa atcaccacca caatcaagag gctgaagtga ttttgtcta gggaggcagg       780 aaaggcttcc tggagtcagc agccagtagg tgaaagagta gattggagac cttcttaatc     840
ttcacaacct cttgtctcaa ggggtgccag gaagctgtgg aggctgaacc cttcttttgc      900
tgccagagag tgggacacct tgagggtcag gtcaagggt tgtaccttgt ttggtagaga       960 attagggggct cttgaagact ttggttgtgg tcaggggagt gtatcttta ggaagagtga      1020 ccaagtgagg aagggtagag gaggacaggt gggagggagt ccaggtggga gtgagtagac      1080
ccagcaggag tgcagggcct aaagccaggt tggtggcagg gctgtgagga gaggcagcca     1140
cctgtgtgtc tgaagaagca ggggcaagag ggaagaggcc agcagactgc cttcacccag     1200
aaactggaat agattgtgag agaccttcc ctgctcttag gaggggctga gttccagtcc       1260
tctcttgtta tacaaggggc ttggtatttg tttacaaaag gggtgtaaag ctagggcaag     1320
gtttgataag gcttctaggg gtatttaaga agtattgttg gggtaattgt ttgtccaatt     1380
aactttgctc ttgaaggac tttcagtaca aactgcaaca acaggattag gaagggaaaa      1440
tttctgagtt ggggttactc ctcagaattt cccagattgt gatctggttt tgattttcaa    1500
gcttgctgac ccaataggtt aacccacaag ttttaaccag accttctcag tccacttact     1560
tcaactgccc ttgccaaagt ccaagagatc ttaaactgtt gtttggcaca gcttcctccc    1620
tcttgggtgg gcaagctttt ggaagagaag gctcctttgg gtgagagtgg ggcaccaaag     1680
tcttccctgt cccttcccct agcttgagaa gcccttctct attgtggact ttgtgcaatt    1740
agcttaatta ctagcttgaa gttgaccttc tggaaatact ttctggttta gcctcacaag    1800
tgagcaagga gggttgagag ttgtgctgtg aggattgtgg ggcccagct ggcagcaggc     1860 tctgggtcag gggggcaggg accaaaggct tacctgacag tgaggagggg tctagtaggg   1920
gatcagttcc cctgttgttc tttagaacct tctggatatt cttcttccct gattgggggt     1980
tgtgaacaat agaatcaact tctacttgta gattgattta gggagaactt ataccctcagt    2040 tgttaagtca ccctgtccag attgtgggtt gctttcctat ttgttcagaa ctttcccaat    2100
tacctcagaa gcacttgaaa tttaaaggat tttaaccca acttagggat tatttcactt     2160
agctcttgca ctttttcttga taattgaatc ctcaggtatt cctctgtttg ggttactaat   2220
agttacttct ttttgggggg ttttcccctg aaaatctttt atccccaatt tgtggcttac   2280
cctctgaagg ttgtttgata attttggaag atttgaaagt cttcttatt tacaaggttt     2340 ggggtctctt taagctgctt ggttctcttg tcagctccca aagcagaaga aagctagctg    2400
aaaattgcaa tagagaagat acttctttc cacctgtttt caactcttat cttcttgaat    2460
ttcagggcac cttttccttgc tcctagtgct tgctatctgt ttattatttt ccttcctgaa    2520
```

```
taccctgaac tccagcttgt tctgctgtaa ttctggcctc cctggcttct tggactcctg    2580
ttccctttgc tctgtcttcc cccaagtcag ctcctgctga acagcttctc agctgaagtg    2640
aacctggagt gcctggatct tgctggatct ttgagtattg cctctggggt ccttggttcc    2700
ttctgctgag ttgctcagaa tctccactcc cccaaccttg tgtggcccct cctgcactcc    2760
tctgattccc cttgtcttcc ctggtttctt gctttggttt aaagtctcca cagaactttt    2820
gcagctcttc tgaagacctg gaagcttttt cttcttaatt ctcttctctt gacctctttt    2880
cccttctttg agagctagaa cttcccttgg tgaacttctc tttccagaat tacttgcctt    2940
cttttccctc ccacttacct gttgtccagg agaggtcaga ttgctgtgct tattggagga    3000
gaaccctttc ttccctgggc tcttcttctc acttgacttc accacttcac ctaattcctt    3060
ggaccctcag tggtgtcact gctggatttt tctttccttt ggctggcctt agggcacacc    3120
caggttgact agaatagtct tggtatttag atccactcac ttttttcagtt tctgtgtctg    3180 tctcttgcct gcttctgact taacccagag aaagcttctc tttcacaagg gttcttagat    3240
ttttgttcac tgagcacctt cttttctgag gcagtgtttt accaataggg gttttcctag    3300
tcagtctaac cttaccttc ttgttgggct tgtctttggt cctgacccct tctctgagtc    3360
tgtaacccag aattgctgta taacccaatt acttgaaatc ctttagaatc ttaacacttc    3420
ttacacctga tttcccctt tattgtatcc aaattgaacc aacccttgt gaatttgaca    3480 gtgatttctc ccagggatcc tagtgtataa ggaataggac ttagtatttt ctattggggg    3540
atataccact taccagatac tgatttgtt ggacttttaa ccctttttc tcttttgaa    3600 agaaagttag gaattatttc ttccagtaga accagtgtaa cctgaaagcc tttgaaagag    3660
tagtttgggt atagctatct gaaaggaatt tctttccaag ggatttcccc agtgctgaca    3720
acaaacaaac agacacaccc tgcaaggtga gtgtaaagaa cactagagca aggc          3774
```

<210> SEQ ID NO 2
<211> LENGTH: 4599
<212> TYPE: DNA
<213> ORGANISM: Artificial Sequence
<220> FEATURE:
<223> OTHER INFORMATION: Description of Artificial Sequence: Vector
      Sequence

<400> SEQUENCE: 2

```
ctgcgcgctc gctcgctcac tgaggccgcc cgggcgtcgg gcgacctttg gtcgcccggc     60
ctcagtgagc gagcgagcgc gcagagaggg agtggccaac tccatcacta ggggttcctt    120
gtagttaatg attaacccgc catgctactt atctacgtag ccatgctcta gtgaattcga    180
cgccgccatc tctaggcccg cgccggcccc ctcgcacaga cttgtgggag aagctcggct    240
actcccctgc cccggttaat ttgcatataa tatttcctag taactataga ggcttaatgt    300
gcgataaaag acagataatc tgttcttttt aatactagct acattttaca tgataggctt    360
ggatttctat aagagataca aatactaaat tattatttta aaaacagca caaaggaaa    420 ctcacccta ctgtaaagta attgtgtgtt ttgagactat aaatatccct tggagaaaag    480
ccttgtttgc gtttagtgaa ccgtcagatg gtaccgttta aactcgagtg agcgcagcaa    540
cgacctgaag atcgatccgt aaagccacag atggggtcga tcttcaggtc gttgcttcgc    600
ctactagagc ggccgccaca gcggggagat ccagacatga taagatacat ttttgaatt    660 caggctatcc caggttgcct tggttcttgg caattgggaa attaagaggg cagagagaat    720
ttgaacagaa actgttctaa tattggtctt ttattgtgta agtattgttc tttggtaaac    780
```

```
ctccttctttt tggtttccag gaattgctgg acacagtggc ttggtgtgtg tctgaggact    840
gtaggccttg gccctaggtt gtggttttag gtctcaggtg ctcttcctgg ctgtctcctt    900
gcttctttcc cttgtcctct tctttgtttc cagccttttc tcccttttgc ttaagtttgg    960
tgcagcaggg tttggctgct ctcagattcc tgcttcctca gttgctgtag ttgtcaggcc   1020
cagaaggctg cagaaggat caggatctgg ctaggtttgc tctcactgtg gcagagtagg   1080
gggaggagga gagcaaaagt gaccccaggc cagctgtagg gagcttaggc ttggtcaacc   1140
agccttcagg tcctagactt tgtcttctct tgagtttggc tgtgtgtgtt tggtgggaac   1200
taggttctac ttagcccaag aaattgggca cttttttgctt gtggtttctg tagagaattg   1260
cactgggtat ctgacttagc ctggcagctt gcctccctca ggtaggttag tctcaggaag   1320
tgaagcaaag tccagcaaga acttcttttg tggcttaaag tctcaattct gtgaggtgct   1380
ggcaaatcac caccacaatc aagaggctga agtgatttttt gtctagggag gcaggaaagg   1440
cttcctggag tcagcagcca gtaggtgaaa gagtagattg agaccttct taatcttcac   1500 aacctcttgt ctcaagggg gccaggaagc tgtggaggct gaacccttct tttgctgcca   1560
gagagtggga caccttgagg gtcaggtcaa ggggttgtac cttgtttggt agagaattag   1620
gggctcttga agactttggt tgtggtcagg ggagtgtatc ttttaggaag agtgaccaag   1680
tgaggaaggg tagaggagga caggtgggag ggagtccagg tgggagtgag tagacccagc   1740
aggagtgcag ggcctaaagc caggttggtg gcagggctgt gaggagaggc agccacctgt   1800
gtgtctgaag aagcaggggc aagagggaag aggccagcag actgccttca cccagaaact   1860
ggaatagatt gtgagagacc tttccctgct cttaggaggg gctgagttcc agtcctctct   1920
tgttatacaa ggggcttggt atttgtttac aaaaggggtg taaagctagg gcaaggtttg   1980
ataaggcttc taggggtatt taagaagtat tgttgggta attgtttgtc caattaactt   2040
tgctcttgga aggactttca gtacaaactg caacaacagg attaggaagg gaaaatttct   2100
gagttggggt tactcctcag aatttcccag attgtgatct ggttttgatt ttcaagcttg   2160
ctgacccaat aggttaaccc acaagtttta accagacctt ctcagtccac ttacttcaac   2220
tgcccttgcc aaagtccaag agatcttaaa ctgttgtttg gcacagcttc ctccctcttg   2280
ggtgggcaag cttttggaag agaaggctcc tttgggtgag agtggggcac caaagtcttc   2340
cctgtccctt cccctagctt gagaagccct tctctattgt ggactttgtg caattagctt   2400
aattactagc ttgaagttga ccttctggaa atactttctg gtttagcctc acaagtgagc   2460
aaggagggtt gagagttgtg ctgtgaggat tgtggggccc cagctggcag caggctctgg   2520
gtcagggggg cagggaccaa aggcttacct gacagtgagg aggggtctag tagggatca    2580 gttcccctgt tgttctttag aaccttctgg atattcttct tccctgattg ggggttgtga   2640
acaatagaat caacttctac ttgtagattg atttagggag aacttatacc tcagttgtta   2700
agtcaccctg tccagattgt gggttgcttt cctatttgtt cagaactttc ccaattacct   2760
cagaagcact tgaaatttaa aggatttaa ccccaactta gggattattt cacttagctc   2820
ttgcactttt cttgataatt gaatcctcag gtattcctct gtttgggtta ctaatagtta   2880
cttcttttgg gggggttttc ccctgaaaat ctttatccc caatttgtgg cttaccctct   2940
gaaggttgtt tgataatttt ggaagatttg aaagtcttct tattttacaa ggtttgggt    3000 ctctttaagc tgcttggttc tcttgtcagc tcccaaagca gaagaaagct agctgaaaat   3060
tgcaatagag aagatacttc ttttccacct gttttcaact cttatcttct tgaatttcag   3120
ggcacctttc cttgctccta gtgcttgcta tctgtttatt attttccttc ctgaataccc   3180
```

```
tgaactccag cttgttctgc tgtaattctg gcctccctgg cttcttggac tcctgtttcc    3240
tttgctctgt cttcccccaa gtcagctcct gctgaacagc ttctcagctg aagtgaacct    3300
ggagtgcctg gatcttgctg gatctttgag tattgcctct ggggtccttg gttccttctg    3360
ctgagttgct cagaatctcc actcccccaa ccttgtgtgg cccttcctgc actcctctga    3420
ttccccttgt cttccctggt ttcttgcttt ggtttaaagt ctccacagaa cttttgcagc    3480
tcttctgaag acctggaagc ttttctct taattctctt ctcttgacct cttttcctt     3540 ctttgagagc tagaacttcc cttggtgaac ttctctttcc agaattactt gccttctttt    3600
ccctcccact tacctgttgt ccaggagagg tcagattgct gtgcttattg gaggagaacc    3660 cttcttccc tgggctcttc ttctcacttg acttcaccac ttcacctaat tccttggacc    3720
ctcagtggtg tcactgctgg attttctctt cctttggctg ccttagggc acacccaggt    3780 tgactagaat agtcttggta tttagatcca ctcactttt cagtttctgt gtctgtctct    3840
tgcctgcttc tgacttaacc cagagaaagc ttctctttca caagggttct tagattttg     3900 ttcactgagc accttctttt ctgaggcagt gttttaccaa taggggtttt cctagtcagt    3960
ctaaccttac ctttcttgtt gggcttgtct ttggtcctga ccctttctct gagtctgtaa    4020
cccagaattg ctgtataacc caattacttg aaatcctta gaatcttaac acttcttaca    4080
cctgatttcc ccttttattg tatccaaatt gaaccaaccc tttgtgaatt tgacagtgat    4140
ttctcccagg gatcctagtg tataaggaat aggacttagt attttctatt ggggatata     4200 ccacttacca gatactgatt tgttggact tttaacccctt ttttctcttt ttgaaagaaa    4260
gttaggaatt atttcttcca gtagaaccag tgtaacctga aagcctttga aagagtagtt    4320
tgggtatagc tatctgaaag gaatttcttt ccaagggatt tccccagtgc tgacaacaaa    4380
caaacagaca caccctgcaa ggtgagtgta aagaacacta gagcaaggct acgtagataa    4440
gtagcatggc gggttaatca ttaactacaa ggaaccccta gtgatggagt tggccactcc    4500
ctctctgcgc gctcgctcgc tcactgaggc cgggcgacca aaggtcgccc gacgcccggg    4560 cttttgcccgg gcggcctcag tgagcgagcg agcgcgcag                         4599
```

<210> SEQ ID NO 3
<211> LENGTH: 23
<212> TYPE: RNA
<213> ORGANISM: Artificial Sequence
<220> FEATURE:
<223> OTHER INFORMATION: Description of Artificial Sequence: Stuffer
      Sequence

<400> SEQUENCE: 3
ggucgaucuu caggucguug cuu                                              23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Stuffer
      Sequence

<400> SEQUENCE: 4
ggtcgatctt caggtcgttg ctt                                              23

<210> SEQ ID NO 5
<211> LENGTH: 86
<212> TYPE: DNA

```
<213> ORGANISM: Artificial Sequence
<220> FEATURE:
<223> OTHER INFORMATION: Description of Artificial Sequence: Stuffer
      Sequence

<400> SEQUENCE: 5
ctcgagtgag cgcagcaacg acctgaagat cgatccgtaa agccacagat ggggtcgatc    60
ttcaggtcgt tgcttcgcct actaga                                        86

<210> SEQ ID NO 6
<211> LENGTH: 119
<212> TYPE: DNA
<213> ORGANISM: Adeno-associated virus

<400> SEQUENCE: 6
ctgcgcgctc gctcgctcac tgaggccgcc cgggcgtcgg gcgacctttg gtcgcccggc    60
ctcagtgagc gagcgagcgc gcagagaggg agtggccaac tccatcacta ggggttcct   119

<210> SEQ ID NO 7
<211> LENGTH: 130
<212> TYPE: DNA
<213> ORGANISM: Adeno-associated virus

<400> SEQUENCE: 7
aggaacccct agtgatggag ttggccactc cctctctgcg cgctcgctcg ctcactgagg    60
ccgggcgacc aaaggtcgcc cgacgcccgg gctttgcccg gcggcctcag tgagcgagc   120 gagcgcgcag                                                         130

<210> SEQ ID NO 8
<211> LENGTH: 11591
<212> TYPE: DNA
<213> ORGANISM: Artificial Sequence
<220> FEATURE:
<223> OTHER INFORMATION: Description of Artificial Sequence: Stuffer
      Sequence

<400> SEQUENCE: 8
gacgcgccct gtagcggcgc attaagcgcg gcgggtgtgg tggttacgcg cagcgtgacc    60
gctacacttg ccagcgccct agcgcccgct cctttcgctt tcttcccttc ctttctcgcc   120
acgttcgccg gctttccccg tcaagctcta aatcggggc tcccctttagg gttccgattt   180 agtgctttac ggcacctcga ccccaaaaaa cttgattagg gtgatggttc acgtagtggg   240
ccatcgccct gatagacggt ttttcgccct ttgacgttgg agtccacgtt cttaatagtg   300
gactcttgtt ccaaactgga acaacactca accctatctc ggtctattct tttgatttat   360
aagggatttt gccgatttcg gcctattggt taaaaatga gctgatttaa caaaaattta   420
acgcgaattt taacaaaata ttaacgctta caatttaggt ggcacttttc ggggaaatgt   480
gcgcggaacc cctatttgtt tatttttcta aatacattca aatatgtatc cgctcatgag   540
acaataaccc tgataaatgc ttcaataata ttgaaaaagg aagagtatga gccatattca   600
acgggaaacg tcttgctcga agccgcgatt aaattccaac atggatgctg atttatatgg   660
gtataaatgg gctcgcgata atgtcgggca atcaggtgcg acaatctatc gattgtatgg   720
gaagcccgat gcgccagagt tgtttctgaa acatggcaaa ggtagcgttg ccaatgatgt   780
tacagatgag atggtcagac taaactggct gacggaattt atgcctcttc cgaccatcaa   840
gcattttatc cgtactcctg atgatgcatg gttactcacc actgcgatcc ccgggaaaac   900
agcattccag gtattagaag aatatcctga ttcaggtgaa aatattgttg atgcgctggc   960
```

```
agtgttcctg cgccggttgc attcgattcc tgtttgtaat tgtccttta acagcgatcg    1020 cgtatttcgt ctcgctcagg cgcaatcacg aatgaataac ggtttggttg atgcgagtga    1080
ttttgatgac gagcgtaatg gctggcctgt tgaacaagtc tggaaagaaa tgcataagct    1140
tttgccattc tcaccggatt cagtcgtcac tcatggtgat ttctcacttg ataaccttat    1200
ttttgacgag gggaaattaa taggttgtat tgatgttgga cgagtcggaa tcgcagaccg    1260
ataccaggat cttgccatcc tatggaactg cctcggtgag ttttctcctt cattacagaa    1320
acggcttttt caaaaatatg gtattgataa tcctgatatg aataaattgc agtttcattt    1380
gatgctcgat gagttttct aactgtcaga ccaagtttac tcatatatac tttagattga    1440
tttaaaactt cattttaat ttaaaaggat ctaggtgaag atcctttttg ataatctcat    1500
gaccaaaatc ccttaacgtg agttttcgtt ccactgagcg tcagacccg tagaaaagat    1560 caaaggatct tcttgagatc cttttttct gcgcgtaatc tgctgcttgc aaacaaaaaa    1620
accaccgcta ccagcggtgg tttgtttgcc ggatcaagag ctaccaactc ttttccgaa    1680 ggtaactggc ttcagcagag cgcagatacc aaatactgtt cttctagtgt agccgtagtt    1740
aggccaccac ttcaagaact ctgtagcacc gcctacatac ctcgctctgc taatcctgtt    1800
accagtggct gctgccagtg gcgataagtc gtgtcttacc gggttggact caagacgata    1860
gttaccggat aaggcgcagc ggtcgggctg aacggggggt tcgtgcacac agcccagctt    1920
ggagcgaacg acctacaccg aactgagata cctacagcgt gagctatgag aaagcgccac    1980
gcttcccgaa gggagaaagg cggacaggta tccggtaagc ggcagggtcg gaacaggaga    2040
gcgcacgagg gagcttccag ggggaaacgc ctggtatctt tatagtcctg tcgggtttcg    2100
ccacctctga cttgagcgtc gatttttgtg atgctcgtca ggggggcgga gcctatggaa    2160
aaacgccagc aacgcggcct ttttacggtt cctggccttt tgctggcctt ttgctcacat    2220
gttctttcct gcgttatccc ctgattctgt ggataaccgt attaccgcct ttgagtgagc    2280
tgataccgct cgccgcagcc gaacgaccga gcgcagcgag tcagtgagcg aggaagcgga    2340
agagcgcctg atgcggtatt ttctccttac gcatctgtgc ggtatttcac accgcataga    2400
ccagccgcgt aacctggcaa atcggttac ggttgagtaa taaatggatg ccctgcgtaa    2460
gcgggtgtgg gcggacaata aagtcttaaa ctgaacaaaa tagatctaaa ctatgacaat    2520
aaagtcttaa actagacaga atagttgtaa actgaaatca gtccagttat gctgtgaaaa    2580
agcatactgg acttttgtta tggctaaagc aaactcttca ttttctgaag tgcaaattgc    2640
ccgtcgtatt aaagaggggc gtggccaagg gcatggtaaa gactatattc gcggcgttgt    2700
gacaatttac cgaacaactc cgcggccggg aagccgatct cggcttgaac gaattgttag    2760
gtggcggtac ttgggtcgat atcaaagtgc atcacttctt cccgtatgcc caactttgta    2820
tagagagcca ctgcgggatc gtcaccgtaa tctgcttgca cgtagatcac ataagcacca    2880
agcgcgttgg cctcatgctt gaggagattg atgagcgcgg tggcaatgcc ctgcctccgg    2940
tgctcgccgg agactgcgag atcatagata tagatctcac tacgcggctg ctcaaacttg    3000
ggcagaacgt aagccgcgag agcgccaaca accgcttctt ggtcgaaggc agcaagcgcg    3060
atgaatgtct tactacggag caagttcccg aggtaatcgg agtccggctg atgttgggag    3120
taggtggcta cgtctccgaa ctcacgaccg aaaagatcaa gagcagcccg catggatttg    3180
acttggtcag gccgagcct acatgtgcga atgatgccca tacttgagcc acctaacttt    3240
gttttagggc gactgccctg ctgcgtaaca tcgttgctgc tgcgtaacat cgttgctgct    3300
```

```
ccataacatc aaacatcgac ccacggcgta acgcgcttgc tgcttggatg cccgaggcat    3360
agactgtaca aaaaaacagt cataacaagc catgaaaacc gccactgcgc cgttaccacc    3420
gctgcgttcg gtcaaggttc tggaccagtt gcgtgagcgc atacgctact tgcattacag    3480
tttacgaacc gaacaggctt atgtcaactg ggttcgtgcc ttcatccgtt ccacggtgt     3540
gcgtcacccg gcaaccttgg gcagcagcga agtcgaggca tttctgtcct ggctggcgaa    3600
cgagcgcaag gtttcggtct ccacgcatcg tcaggcattg gcggccttgc tgttcttcta    3660
cggcaaggtg ctgtgcacgg atctgccctg gcttcaggag atcggaagac ctcggccgtc    3720
gcggcgcttg ccggtggtgc tgaccccgga tgaagtggtt cgcatcctcg gttttctgga    3780
aggcgagcat cgtttgttcg cccaggactc tagctatagt tctagtggtt ggctacagct    3840
tgcatgcctg caggcagctg cgcgctcgct cgctcactga ggccgcccgg gcgtcgggcg    3900
acctttggtc gcccggcctc agtgagcgag cgagcgcgca gagggagt ggccaactcc      3960
atcactaggg gttccttgta gttaatgatt aacccgccat gctacttatc tacgtagcca    4020
tgctctagtg aattcgacgc cgccatctct aggcccgcgc cggccccctc gcacagactt    4080
gtgggagaag ctcggctact cccctgcccc ggttaatttg catataatat ttcctagtaa    4140
ctatagaggc ttaatgtgcg ataaaagaca gataatctgt tcttttaat actagctaca     4200
ttttacatga taggcttgga tttctataag agatacaaat actaaattat tattttaaaa    4260
aacagcacaa aaggaaactc accctaactg taaagtaatt gtgtgttttg agactataaa    4320
tatcccttgg agaaaagcct tgtttgcgtt tagtgaaccg tcagatggta ccgtttaaac    4380
tcgagtgagc gcagcaacga cctgaagatc gatccgtaaa gccacagatg gggtcgatct    4440
tcaggtcgtt gcttcgccta ctagagcggc cgccacagcg gggagatcca gacatgataa    4500
gatacatttt ttgaattcag gctatcccag gttgccttgg ttcttggcaa ttgggaaatt    4560
aagagggcag agagaatttg aacagaaact gttctaatat tggtctttta ttgtgtaagt    4620
attgttcttt ggtaaacctc cttcttttgg tttccaggaa ttgctggaca cagtggcttg    4680
gtgtgtgtct gaggactgta ggccttggcc ctaggttgtg gttttaggtc tcaggtgctc    4740
ttcctggctg tctccttgct tcttttccctt gtcctcttct ttgttccag ccttttctcc    4800
cttttgctta agtttggtgc agcagggttt ggctgctctc agattcctgc ttcctcagtt    4860
gctgtagttg tcaggcccag aaggctggca gaaggatcag gatctggcta ggtttgctct    4920
cactgtggca gagtaggggg aggaggagag caaaagtgac cccaggccag ctgtagggag    4980
cttaggcttg gtcaaccagc cttcaggtcc tagactttgt cttctcttga gtttggctgt    5040
gtgtgtttgg tgggaactag gttctactta gcccaagaaa ttgggcactt tttgcttgtg    5100
gtttctgtag agaattgcac tgggtatctg acttagcctg gcagcttgcc tccctcaggt    5160
aggttagtct caggaagtga agcaaagtcc agcaagaact tcttttgtgg cttaaagtct    5220
caattctgtg aggtgctggc aaatcaccac cacaatcaag aggctgaagt gattttgtc     5280
tagggaggca ggaaaggctt cctggagtca gcagccagta ggtgaaagag tagattggag    5340
accttcttaa tcttcacaac ctcttgtctc aagggggtgcc aggaagctgt ggaggctgaa    5400
cccttctttt gctgccagag agtgggacac cttgagggtc aggtcaaggg gttgtaacctt   5460
gtttggtaga gaattagggg ctcttgaaga ctttggttgt ggtcagggga gtgtatcttt    5520
taggaagagt gaccaagtga ggaagggtag aggaggacag gtgggaggga gtccaggtgg    5580
gagtgagtag acccagcagg agtgcagggc ctaaagccag gttggtggca gggctgtgag    5640
gagaggcagc cacctgtgtg tctgaagaag caggggcaag agggaagagg ccagcagact    5700
```

```
gccttcaccc agaaactgga atagattgtg agagaccttt ccctgctctt aggagggggct   5760
gagttccagt cctctcttgt tatacaaggg gcttggtatt tgtttacaaa aggggtgtaa   5820
agctagggca aggtttgata aggcttctag gggtatttaa gaagtattgt tggggtaatt   5880
gtttgtccaa ttaactttgc tcttggaagg actttcagta caaactgcaa caacaggatt   5940
aggaagggaa aatttctgag ttggggttac tcctcagaat ttcccagatt gtgatctggt   6000
tttgattttc aagcttgctg acccaatagg ttaacccaca agttttaacc agaccttctc   6060
agtccactta cttcaactgc ccttgccaaa gtccaagaga tcttaaactg ttgtttggca   6120
cagcttcctc cctcttgggt gggcaagctt tggaagaga aggctccttt gggtgagagt   6180
ggggcaccaa agtcttccct gtcccttccc ctagcttgag aagcccttct ctattgtgga   6240
ctttgtgcaa ttagcttaat tactagcttg aagttgacct tctggaaata ctttctggtt   6300
tagcctcaca agtgagcaag gagggttgag agttgtgctg tgaggattgt ggggccccag   6360
ctggcagcag gctctgggtc aggggggcag ggaccaaagg cttacctgac agtgaggagg   6420
ggtctagtag gggatcagtt cccctgttgt tctttagaac cttctggata ttcttcttcc   6480
ctgattgggg gttgtgaaca atagaatcaa cttctacttg tagattgatt tagggagaac   6540
ttataccctca gttgttaagt caccctgtcc agattgtggg ttgcttttcct atttgttcag   6600
aactttccca attacctcag aagcacttga aatttaaagg attttaaccc caacttaggg   6660
attatttcac ttagctcttg cacttttctt gataattgaa tcctcaggta ttcctctgtt   6720
tgggttacta atagttactt ctttttggggg ggttttcccc tgaaaatctt ttatccccaa   6780
tttgtggctt accctctgaa ggttgtttga taattttgga agatttgaaa gtcttcttat   6840
tttacaaggt ttggggtctc tttaagctgc ttggttctct tgtcagctcc caaagcagaa   6900
gaaagctagc tgaaaattgc aatagagaag atacttcttt tccacctgtt ttcaactctt   6960
atcttcttga atttcagggc accttttcctt gctcctagtg cttgctatct gtttattatt   7020
ttccttcctg aatacccctga actccagctt gttctgctgt aattctggcc tccctggctt   7080
cttggactcc tgtttccttt gctctgtctt cccccaagtc agctcctgct gaacagcttc   7140
tcagctgaag tgaacctgga gtgcctggat cttgctggat ctttgagtat tgcctctggg   7200
gtccttggtt ccttctgctg agttgctcag aatctccact cccccaacct tgtgtggccc   7260
ttcctgcact cctctgattc cccttgtctt ccctggtttc ttgctttggt ttaaagtctc   7320
cacagaactt ttgcagctct tctgaagacc tggaagcttt ttcttcttaa ttctcttctc   7380
ttgacctctt ttcccttctt tgagagctag aacttccctt ggtgaacttc tctttccaga   7440
attacttgcc ttcttttccc tcccacttac ctgttgtcca ggagaggtca gattgctgtg   7500
cttattggag gagaaccctt tcttccctgg gctcttcttc tcacttgact tcaccacttc   7560
acctaattcc ttggaccctc agtggtgtca ctgctggatt tttctttcct ttggctggcc   7620
ttagggcaca cccaggttga ctagaatagt cttggtattt agatccactc acttttttcag   7680
tttctgtgtc tgtctcttgc ctgcttctga cttaacccag agaaagcttc tctttcacaa   7740
gggttcttag attttttgttc actgagcacc ttcttttctg aggcagtgtt ttaccaatag   7800
gggttttcct agtcagtcta accttacctt tcttgttggg cttgtctttg gtcctgaccc   7860
tttctctgag tctgtaaccc agaattgctg tataacccaa ttacttgaaa tcctttagaa   7920
tcttaacact tcttacacct gatttcccct tttattgtat ccaaattgaa ccaacccttt   7980
gtgaatttga cagtgatttc tcccagggat cctagtgtat aaggaatagg acttagtatt   8040
```

```
ttctattggg ggatatacca cttaccagat actgattttg ttggactttt aacccttttt    8100
tctcttttg aaagaaagtt aggaattatt tcttccagta gaaccagtgt aacctgaaag     8160
cctttgaaag agtagtttgg gtatagctat ctgaaaggaa tttctttcca agggatttcc    8220
ccagtgctga caacaaacaa acagacacac cctgcaaggt gagtgtaaag aacactagag    8280
caaggctacg tagataagta gcatggcggg ttaatcatta actacaagga acccctagtg    8340
atggagttgg ccactccctc tctgcgcgct cgctcgctca ctgaggccgg gcgaccaaag    8400
gtcgcccgac gcccgggctt tgcccgggcg gcctcagtga gcgagcgagc gcgcagctgc    8460
ctgcaggtct gagacaataa ccctgataaa tgcttcaata atgtaagctt gtcgagaagt    8520
actagaggat cataatcagc cataccacat ttgtagaggt tttacttgct ttaaaaaacc    8580
tcccacacct cccccctgaac ctgaaacata aatgaatgc aattgaggcc ttaattctag    8640
ccataaaagg tcttgagcag gccgttgaaa acctcagccg tatcagcaaa acggcggtgc    8700
ctggtgccgc cgcaatgacc attaaccgcg ttgcttcatc cgcgatagcg cagtcggcgt    8760
cacaggttgc ccgtgagaca aaggtacgcc ggaaactggt aaaggaaagg gccaggctga    8820
aaagggccac ggtcaaaaat ccgcaggcca gaatcaaagt tagccggggg gatttgcccg    8880
taatcaagct gggtaatgcg cgggttgtcc tttcgcgccg caggcgtcgt aaaaggggc    8940
agcgttcatc cctgaaaggt ggcggcagcg tgcttgtggt gggtaaccgt cgtattcccg    9000
gcgcgtttat tcagcaactg aaaaatggcc ggtggcatgt catgcagcgt gtggctggga    9060
aaaccgtta ccccattgat gtggtgaaaa tcccgatggc ggtgccgctg accacggcgt     9120
tgaaacaaaa tagtgagcgg atacggcgtg aacgtcttcc gaaagagctg ggctatgcgc    9180
tgaagcatca actcacactg gtaataaagc gtagaaacat actgaacctc cgtgcagccg    9240
tactggatgc actggagaag catgacaccg ggcgacgtt ttttgatggt cgccccgctg     9300
tttttgatga ggcggatttt ccggcagttg ccgtttatct caccggcgct gaatacacgg    9360
gcgaagagct ggacagcgat acctggcagg cggagctgca tatcgaagtt ttcctgcctg    9420
ctcaggtgcc ggattcagag ctggatgcgt ggatggagtc ccggatttat ccggtgatga    9480
gcgatagccc ggcactgtca gatttgatca ccagtatggt gaccagcggc tatgactacc    9540
ggcgcgacga tgatgcgggc ttgtggagtt cagccgatct gacttatgtc attacctatg    9600
aaatgtctcc acgcttatga gcagcagact caacaggaca aaaatccgca gcagcagagc    9660
gataccgaag cgtcacggct gaaatatacc gaagaggcgc agaaggctta cgaacggctg    9720
aagacgccgc tggagaaata taccgcccgt caggaagaac tgaacaaggc actgaaagac    9780
gggaaaatcc tgaaggcgga ttacaacacg ctgatggcgg cggcgaaaaa ggattatgaa    9840
gcgacgctga aaaagccgaa acagtccagc gtgaaggtgt ctgcgggcga tagtcaggaa    9900
gacagtgctc atgctgccct gctgacgctt caggcagaac tcctgacgct ggagaagcaa    9960
gccgagcaa atgagaaaat cagccagcag cgccgggatt tgtggaaggc ggagagtcag   10020
ttcgcggtac tggaggaggc ggcgcaacgt cgccaggtgt ctgcacagga gaaatccctg   10080
ctggcgcata agatgagac gctggagtac aaacgccagg tggctgcact tggcgacaag    10140
gttaggtatc aggagcgcct gaacgcgctg gcgcagcagg cggataaatt cgcacagcag   10200
caacgggcaa acgggccgc cattgatgcg aaaagccggg ggctgactga ccggcaggca   10260
gaacgggaag ccacggaaca gcgcctgaag gaacagtatg gcgataatcc gctggcgctg   10320
aataacgtca tgtcagagca gaaaaagacc tgggcggctg aagaccagct tcgcgggaac   10380
tggatggcag acctgaagtc cggctggagt gagtgggaag agagcgccac ggacagtatg   10440
```

```
tcgcaggtaa aaagtgcagc cacgcagacc tttgatggta ttgcacagaa tatggcggcg    10500
atgctgaccg gcagtgagca gaactggcgc agcttcaccc gttccgtgct gtccatgatg    10560
acagaaattc tgctttagca ggcaatggtg gggattgtcg ggagtatcgg cagcgccatt    10620 ggcgggctg ttggtggcgg cgcatccgcg tcaggcggta cagccattca ggccgctgcg    10680
gcgaaattcc attttgcaac cggaggattt acgggaaccg gcggcaaata tgagccagcg    10740
gggattgttc accgtggtga gtttgtcttc acgaaggagg caaccagccg gattggcgtg    10800
gggaatcttt accggctgat gcgcggctat gccaccggcg gttatgtcgg tacaccgggc    10860
agcatggcag acagccggtc gcaggcgtcc gggacgtttg agcagaataa ccatgtggtg    10920
attaacaacg acggcacgaa cgggcagata ggtccggctg ctctgaaggc ggtgtatgac    10980
atggcccgca agggtgcccg tgatgaaatt cagacacaga tgcgtgatgg tggcctgttc    11040
tcctgacctc cacgatgagg cgcgcccaat tgttgttgtt aacttgttta ttgcagctta    11100
taatggttac aaataaagca atagcatcac aaatttcaca aataaagcat ttttttcact    11160
gcattctagt tgtggtttgt ccaaactcat caatgtatct tatcatgtct ggatctgatc    11220
actgatatcg cctaggagat ccgaaccaga taagtgaaat ctagttccaa actattttgt    11280
catttttaat tttcgtatta gcttacgacg ctacacccag ttcccatcta ttttgtcact    11340
cttccctaaa taatccttaa aaactccatt tccacccctc ccagttccca actattttgt    11400
ccgcccacag cggggcattt ttcttcctgt tatgttttta atcaaacatc ctgccaactc    11460
catgtgacaa accgtcatct tcggctactt tttctctgtc acagaatgaa aatttttctg    11520
tcatctcttc gttattaatg tttgtaattg actgaatatc aacgcttatt tgcagcctga    11580
atggcgaatg g                                                         11591
```

THERAPEUTIC FOR TREATMENT OF DISEASES INCLUDING THE CENTRAL NERVOUS SYSTEM

RELATED APPLICATIONS

This patent application is the National Phase of International Application No. PCT/US2017/022973, filed Mar. 17, 2017, which designated the U.S. and that International Application was published under PCT Article 21(2) in English, which claims the benefit of priority to U.S. Provisional Patent Application No. 62/310,229, filed Mar. 18, 2016 and U.S. Provisional Patent Application No. 62/367,858, filed Jul. 28, 2016. The entire contents of the foregoing applications are incorporated herein by reference in their entirety, including all text, tables, sequence listing and drawings.

SEQUENCE LISTING

The instant application contains a Sequence Listing which has been submitted electronically in ASCII format and is hereby incorporated by reference in its entirety. Said ASCII copy, created on Sep. 14, 2018, is named "CHOP0461888 ST25.txt" and is 27.6 KB in size.

INTRODUCTION

Gene transfer is now widely recognized as a powerful tool for analysis of biological events and disease processes at both the cellular and molecular level. More recently, the application of gene therapy for the treatment of human diseases, either inherited (e.g., ADA deficiency) or acquired (e.g., cancer or infectious disease), has received considerable attention. With the advent of improved gene transfer techniques and the identification of an ever expanding library of defective gene-related diseases, gene therapy has rapidly evolved from a treatment theory to a practical reality.

Traditionally, gene therapy has been defined as a procedure in which an exogenous gene is introduced into the cells of a patient in order to correct an inborn genetic error. Although more than 4500 human diseases are currently classified as genetic, specific mutations in the human genome have been identified for relatively few of these diseases. Until recently, these rare genetic diseases represented the exclusive targets of gene therapy efforts. Accordingly, most of the NIH approved gene therapy protocols to date have been directed toward the introduction of a functional copy of a defective gene into the somatic cells of an individual having a known inborn genetic error. Only recently, have researchers and clinicians begun to appreciate that most human cancers, certain forms of cardiovascular disease, and many degenerative diseases also have important genetic components, and for the purposes of designing novel gene therapies, should be considered "genetic disorders." Therefore, gene therapy has more recently been broadly defined as the correction of a disease phenotype through the introduction of new genetic information into the affected organism.

In in vivo gene therapy, a transferred gene is introduced into cells of the recipient organism in situ that is, within the recipient. In vivo gene therapy has been examined in several animal models. Several recent publications have reported the feasibility of direct gene transfer in situ into organs and tissues such as muscle, hematopoietic stem cells, the arterial wall, the nervous system, and lung. Direct injection of DNA into skeletal muscle, heart muscle and injection of DNA-lipid complexes into the vasculature also has been reported to yield a detectable expression level of the inserted gene product(s) in vivo.

Recombinant adeno-associated virus (AAV) vectors have shown excellent therapeutic promise in several early phase clinical trials by multiple groups reported to date. Development of this new class of biologic product towards advanced clinical studies and eventual approval will involve further improvements in vector characterization and quality control methods, including a better understanding of how vector design and manufacturing process parameters affect impurity profiles in the purified clinical grade vectors. Removal of DNA impurities in AAV vectors is complicated by the fact that even with efficient nuclease treatment to remove accessible nucleic acids during vector purification, fragments of DNA may be packaged and thus resistant to nuclease treatment performed in a manner to maintain vector particle integrity.

An important objective in the design of rAAV production systems is to characterize and implement strategies to minimize/control the generation of vector-related impurities, including wild-type/pseudo wild-type AAV species (wtAAV), AAV-encapsidated residual DNA impurities, and empty AAV capsids. Such product-related impurities closely resemble the vector itself, and cannot easily be separated from bona fide vectors during the purification process. Non vector DNA impurities have been reported at an abundance in the range from 1 to 8% of total DNA in purified vector particles (Smith P H Wright J F. Qu G. et al 2003, *Mo. Therapy,* 7:8348; Chadeuf G. Ciron C. Moullier P. Salvetti A., *Mo. Therapy* 2005, 12:744. Report from the CHMP gene therapy expert group meeting. European Medicines Agency EMEA/CHMP 2005, 183989/2004). A significant portion of the encapsidated residual DNA is derived from the ITR-containing vector plasmid template.

SUMMARY

In accordance with the invention, provided are filler or stuffer nucleic acid sequences. Such filler or stuffer sequences are useful in the context of vectors as set forth herein. For example such filler or stuffer sequences can be used to adjust the length of a vector sequence for improved virus packaging and/or reduction in impurities, which include contaminating nucleic acid or empty virus vectors.

In one embodiment, a vector filler or stuffer sequence comprises a nucleic acid between about 500 and 5000 nucleotides in length and having at least 75% identity to a sequence as set forth in Example 1, e.g., SEQ ID NO:1.

In another embodiment, an AAV vector filler or stuffer sequence comprises a nucleic acid of about 500 to 5000 nucleotides in length and having at least 75% identity to a sequence as set forth in Example 1, e.g., SEQ ID NO:1.

In additional embodiments, a vector or AAV vector filler or stuffer sequence comprises or consists essentially of about 500 to 5000 nucleotides; comprises or consists essentially of about 1000 to 5000 nucleotides; comprises or consists essentially of about 1500 to 5000 nucleotides; comprises or consists essentially of about 2000 to 5000 nucleotides; comprises or consists essentially of about 2500 to 5000 nucleotides; comprises or consists essentially of about 3000 to 5000 nucleotides; comprises or consists essentially of about 3500 to 5000 nucleotides; comprises or consists essentially of about 4000 to 5000 nucleotides; comprises or consists essentially of about 4000 to 4800 nucleotides; comprises or consists essentially of about 4200 to 4800 nucleotides; comprises or consists essentially of about 4400 to 4800 nucleotides; comprises or consists essentially of about 4200 to 4600 nucleotides; comprises or consists essentially of about 4400 to 4600 nucleotides; comprises or consists essentially of about 4500 to 4600 nucleotides, or about 4600 nucleotides.

In additional embodiments, a vector or AAV vector filler or stuffer sequence comprises or consists essentially of about 500 to 5000 nucleotides of SEQ ID NO:1; comprises or consists essentially of about 1000 to 5000 nucleotides of SEQ ID NO:1; comprises or consists essentially of about 1500 to 5000 nucleotides of SEQ ID NO:1; comprises or consists essentially of about 2000 to 5000 nucleotides of SEQ ID NO:1; comprises or consists essentially of about 2500 to 5000 nucleotides of SEQ ID NO:1; comprises or consists essentially of about 3000 to 5000 nucleotides of SEQ ID NO:1; comprises or consists essentially of about 3500 to 5000 nucleotides of SEQ ID NO:1; comprises or consists essentially of about 4000 to 5000 nucleotides of SEQ ID NO:1; comprises or consists essentially of about 4000 to 4800 nucleotides of SEQ ID NO:1; comprises or consists essentially of about 4200 to 4800 nucleotides of SEQ ID NO:1; comprises or consists essentially of about 4400 to 4800 nucleotides of SEQ ID NO:1; comprises or consists essentially of about 4200 to 4600 nucleotides of SEQ ID NO:1; comprises or consists essentially of about 4400 to 4600 nucleotides of SEQ ID NO:1; comprises or consists essentially of about 4500 to 4600 nucleotides of SEQ ID NO:1; or about 4600 nucleotides of SEQ ID NO:1.

In further embodiments, a vector or AAV vector filler or stuffer sequence comprises or consists essentially of a nucleic acid with at least 80% identity to SEQ ID NO:1; comprises or consists essentially of a nucleic acid with at least 85% identity to SEQ ID NO:1; comprises or consists essentially of a nucleic acid with at least 90% identity to SEQ ID NO:1; comprises or consists essentially of a nucleic acid with at least 95% identity to SEQ ID NO:1; comprises or consists essentially of a nucleic acid with 100% identity to all or a part of SEQ ID NO:1.

In still further embodiments, a vector or AAV vector filler or stuffer sequence comprises or consists essentially of a nucleic with about 80%-85% identity to SEQ ID NO:1; comprises or consists essentially of a nucleic with about 85%-90% identity to SEQ ID NO:1; comprises or consists essentially of a nucleic with about 90%-95% identity to SEQ ID NO:1; comprises or consists essentially of a nucleic with about 95%-100% identity to SEQ ID NO:1.

The invention also provides plasmids comprising the filler or stuffer sequences set forth herein, e.g., as disclosed above. In one embodiment, a plasmid comprises a selectable marker (e.g., an antibiotic resistance gene) and/or an origin of replication. A particular non-limiting plasmid is pKFBextmU6miS1newStfr (SEQ ID NO:8).

The invention further provides filler or stuffer sequences set forth herein, e.g., as disclosed above, linked to other nucleic acid sequences. In one embodiment, a filler or stuffer sequence is linked to a heterologous nucleic acid; and/or linked to one or more AAV ITRs; and/or linked to a promoter; and/or linked to a poly-adenylation signal; and/or linked to an intron.

In embodiments with a heterologous nucleic acid sequence, filler or stuffer sequence(s) can flank the heterologous nucleic acid sequence. In embodiments with one or more AAV ITRs, filler or stuffer sequence(s) can be flanked by the AAV ITR(s). In embodiments with a heterologous nucleic acid sequence linked to one or more AAV ITRs, the AAV ITR(s) can flank the filler or stuffer sequence, e.g., AAV ITR(s) can be positioned at the 5' or 3' end of the filler or stuffer sequence; and/or the filler or stuffer sequence can flank the heterologous nucleic acid sequence, e.g., the filler or stuffer sequence can be positioned at the 5' or 3' end of the heterologous nucleic acid sequence.

In certain embodiments, one or more ITRs comprise an AAV2 ITR.

In certain embodiments, a promoter is a pol III promoter or a mU6 promoter.

In certain embodiments, wherein heterologous nucleic acid sequence encodes or produces (is transcribed into) a therapeutic agent.

In certain embodiments, the sequence encoding or producing a therapeutic agent comprises a nucleic acid encoding a protein or an inhibitory nucleic acid.

In certain embodiments, the heterologous nucleic acid sequence is flanked by a poly-Adenine sequence located 3' of the sequence.

In certain embodiments, the inhibitory nucleic acid comprises a micro-RNA (miRNA), siRNA (small interfering RNA), trans-splicing RNA, antisense RNA or triplex forming RNA molecule.

In certain embodiments, the inhibitory nucleic acid comprises SEQ ID NO:3, or a sequence complementary thereto.

In certain embodiments, the protein comprises a growth factor, a cytokine, a blood clotting factor, or an immunoglobulin.

The invention moreover provides cells comprising the filler or stuffer sequences set forth herein, e.g., as disclosed above.

The invention still further provides virus vectors comprising the filler or stuffer sequences set forth herein, e.g., as disclosed above.

In certain embodiments, a virus vector comprises a recombinant adeno-associated virus (rAAV) vector.

In certain embodiments, a virus vector comprises a recombinant adeno-associated virus (rAAV) vector comprising an AAV capsid protein comprising the filler or stuffer sequences set forth herein, e.g., as disclosed above.

In certain embodiments, a virus vector comprises a rAAV vector comprising an AAV capsid protein of an AAV1, AAV2, AAV3, AAV4, AAV5, AAV6, AAV7, AAV8, AAV9, and/or AAV10 capsid protein, or a hybrid or chimera of any of the foregoing AAV capsids.

The invention moreover provides methods of delivering a heterologous nucleic acid sequence (e.g., a therapeutic agent) to a cell of a subject (e.g. mammal). In certain embodiments, a method includes administering to the subject (e.g. mammal) a recombinant adeno-associated virus (rAAV) vector comprising an AAV capsid protein, a vector comprising a heterologous nucleic acid sequence (e.g., encoding a therapeutic agent) and a filler or stuffer sequence inserted between a pair of AAV inverted terminal repeats in a manner effective to infect the cell of the subject (e.g. mammal) such that the cell expresses the heterologous nucleic acid sequence (e.g., encoding a therapeutic agent) in the subject (e.g. mammal).

The invention additionally provides methods of treating a disease in a subject (e.g. mammal). In certain embodiments, a method includes administering to the subject (e.g. mammal) a recombinant adeno-associated virus (rAAV) vector comprising an AAV capsid protein, a vector comprising a heterologous nucleic acid sequence encoding a therapeutic agent and a filler or stuffer sequence inserted between a pair of AAV inverted terminal repeats in a manner effective to infect a cell of the subject (e.g. mammal), wherein the cell expresses the therapeutic agent so as to treat the disease.

The invention still moreover provides methods of delivering a therapeutic agent to a central nervous system (CNS) cell of a subject (e.g. mammal).

In certain embodiments, a method includes administering to the subject's (e.g. mammal's) CNS a recombinant adeno-associated virus (rAAV) vector comprising an AAV capsid protein, a vector comprising a heterologous nucleic acid sequence encoding a therapeutic agent and a filler or stuffer sequence inserted between a pair of AAV inverted terminal repeats in a manner effective to infect the CNS cell of the subject (e.g. mammal) such that the CNS cell expresses the therapeutic agent in the subject (e.g. mammal).

The invention yet additionally provides methods of treating a central nervous system (CNS) disease in a subject (e.g. mammal). In certain embodiments, a method includes administering to the subject's (e.g. mammal's) central nervous system (CNS) a recombinant adeno-associated virus (rAAV) vector comprising an AAV capsid protein, a vector comprising a heterologous nucleic acid sequence encoding a therapeutic agent and a filler or stuffer sequence inserted between a pair of AAV inverted terminal repeats in a manner effective to infect the CNS cell of the subject (e.g. mammal) such that the CNS cell expresses the therapeutic agent so as to treat the CNS disease.

In certain embodiments, rAAV vector is administered to the cerebellar cortex, inferior olive (medulla), and/or the ventral lateral thalamic nuclei.

In certain embodiments, rAAV vector is administered to the mammal's deep cerebella nuclei.

In certain embodiments, the cell is a cerebellar Purkinje cell (PC), brainstem neuron, or thalamus cell.

In certain embodiments, the cell is within the cerebellar cortex, inferior olive (medulla), or the ventral lateral thalamic nuclei.

In certain embodiments, the mammal is a primate, horse, sheep, goat, pig, or dog.

In certain embodiments, the mammal is a non-rodent mammal.

In certain embodiments, the mammal is human.

In certain embodiments, the therapeutic agent comprises a nucleic acid encoding a protein or an inhibitory nucleic acid.

In certain embodiments, the inhibitory nucleic acid is an RNAi or antisense RNA molecule.

In certain embodiments, the RNAi molecule comprises a siRNA (small interfering RNA) or miRNA (microRNA).

In certain embodiments, the mammal the RNAi molecule comprises a sequence set forth in Example 1, e.g., SEQ ID NO:3, or a sequence complementary thereto.

In certain embodiments, the protein comprises a growth factor, a cytokine, a blood clotting factor, or an immunoglobulin.

In certain embodiments, the CNS disease is a neurodegenerative disease.

In certain embodiments, the neurodegenerative disease is Alzheimer's disease, Huntington's disease, ALS, hereditary spastic hemiplegia, primary lateral sclerosis, spinal muscular atrophy, Kennedy's disease, a polyglutamine repeat disease, or Parkinson's disease.

In certain embodiments, the neurodegenerative disease is polyglutamine repeat disease.

In certain embodiments, the polyglutamine repeat disease is a spinocerebellar ataxia (SCA1, SCA2, SCA3, SCA6, SCA7, or SCA17).

In certain embodiments, the method reduces expression of ataxin-1.

In certain embodiments, the rAAV vector comprises an AAV1, AAV2, AAV3, AAV4, AAV5, AAV6, AAV7, AAV8, AAV9, and/or AAV10 capsid or a hybrid or chimera of any of the foregoing AAV capsids.

In certain embodiments, the rAAV vector is rAAV2/1.

In certain embodiments, the rAAV vector is administered in a single dose to the mammal's cerebellar cortex, inferior olive (medulla), or the ventral lateral thalamic nuclei and/or deep cerebella nuclei.

In certain embodiments, the rAAV vector is administered at a dose of about 1-5 ml of $1\times10^5$-$1\times10^{16}$ vector genomes (vg)/ml.

In certain embodiments, the rAAV vector is administered at a dose of about 1-3 ml of $1\times10^7$-$1\times10^{14}$ vector genomes (vg)/ml.

In certain embodiments, the rAAV vector is administered at a dose of about 1-2 ml of $1\times10^8$-$1\times10^{13}$ vector genomes (vg)/ml.

In certain embodiments, the cell expresses the therapeutic agent at a level that reduces Atxn1 mRNA or mutant Atxn1 mRNA level by at least 10% in the cerebellum, deep cerebella nuclei, brain stem (BS), and/or thalamus.

In certain embodiments, the cell expresses the therapeutic agent at a level that reduces Atxn1 mRNA or mutant Atxn1 mRNA level by at least 10-50% in the cerebellum, deep cerebella nuclei, brain stem (BS), and/or thalamus.

The invention yet further provides methods of producing recombinant AAV particles. In certain embodiments, a method includes introducing into packaging helper cells a recombinant AAV vector comprising filler or stuffer sequence(s) set forth herein, e.g., as disclosed above; and culturing the helper cells under conditions to produce recombinant AAV particles, wherein the recombinant AAV particles produced have the filler or stuffer sequence(s).

In certain embodiments, the helper cells comprise mammalian cells.

In certain embodiments, the helper cells provide helper functions that package said vector into a viral particle.

In certain embodiments, the helper cells provide AAV helper functions.

In certain embodiments, the helper cells provide AAV Rep and/or Cap proteins.

In certain embodiments, the helper cell is stably or transiently transfected with nucleic acid sequence(s) encoding Rep and/or Cap protein sequence(s).

In certain embodiments, the helper cells provide Rep78 or/and Rep68 proteins.

In certain embodiments, the AAV particles comprise an AAV1, AAV2, AAV3, AAV4, AAV5, AAV6, AAV7, AAV8, AAV9, AAV10, AAV11, Rh74, Rh10 serotype, or a hybrid or chimera of any of the foregoing AAV serotypes.

In certain embodiments, the AAV particles comprise a VP1, VP2 or VP3 capsid protein of AAV1, AAV2, AAV3, AAV4, AAV5, AAV6, AAV7, AAV8, AAV9, AAV10, AAV11, Rh74, Rh10 serotype, or a hybrid or chimera of any of the foregoing AAV serotypes.

In certain embodiments, the AAV capsid and/or ITR sequence(s), Cap, and/or Rep, are derived from AAV1, AAV2, AAV3, AAV4, AAV5, AAV6, AAV7, AAV8, AAV9, AAV10, AAV11, Rh74, Rh10 serotype, or a hybrid or chimera of any of the foregoing AAV serotypes.

BRIEF DESCRIPTION OF THE DRAWINGS

FIG. 3A-3F show cerebellar pathology.

FIG. 6A-6F show cerebellar pathology in mice treated after disease onset.

DETAILED DESCRIPTION

Figure 1A:
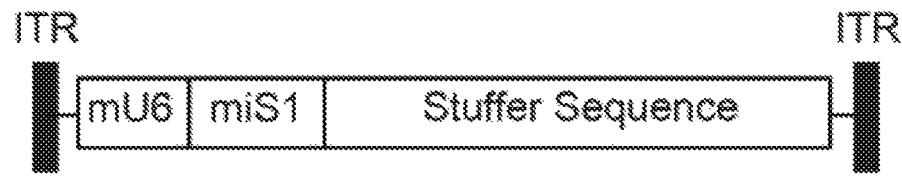
FIG. 1A-1D show experimental design and rotarod analysis.

Levels of residual plasmid DNA impurities can be elevated in preparations of recombinant adeno-associated virus (rAAV) vector with expression cassettes shorter than the natural rAAV packaging limit (approximately 4.7 kb). Shorter sequences than the natural rAAV packaging can increase the level of impurities. Adjusting the size of a vector genome sequence will mitigate potential risks associated with vector mediated transfer of undesirable nucleic acid sequences, such as bacterial genes causing antibiotic resistance.

Accordingly, adjusting the length of nucleic acid during vector design so length of the packaged vector genome is at, or close to or slightly greater than the (natural) packaging limit of viral (AAV) capsid will reduce or prevent encapsidation of contaminating nucleic acid, which in turn reduces viral (AAV) particles with encapsidated nucleic acid impurities. Such sequences used to adjust the length can be referred to as filler or stuffer sequences.

In addition to adjusting the length of the vector genome to be at or close to the (natural) packaging limit of AAV capsid, filler or stuffer sequences can be designed so they exhibit reduced adverse effects in the context of in vivo gene therapy. For example, filler or stuffer sequences can be designed to have reduced, minimized or lack one or more elements. In one embodiment, CpG residues are reduced or eliminated so the DNA elements retained in transduced cells for expression of a transgene shorter in length than full length packaged size in vivo leads to a reduced or decreased immune response, or optimally does not stimulate, promote or induce an immune response. In another embodiment, a filler or stuffer sequence can be designed to reduce or minimize the frequency of ATG codons or delete them entirely, in order to reduce or eliminate the possibility of peptides being generated from the filler or stuffer sequence due to latent start codons. In a further embodiment, a filler or stuffer can be designed to reduce, minimize or eliminate known active cis acting elements. For example, a filler or stuffer with no known promoter sequences, enhancer sequences, repressor sequences, splicing doors or acceptors, or other cis-acting elements found in the human genome that could potentially affect transcription of the transgene. Hence, the term "safe" filler or stuffer sequence.

The invention therefore provides filler or stuffer sequences having one or more of the foregoing attributes. The invention also provides a filler or stuffer sequence comprising a nucleic acid between about 500 and 5000 nucleotides in length and having at least 75% identity to SEQ ID NO:1. The invention further provides a filler an AAV vector including a filler or stuffer sequence that comprises a nucleic acid of about 500 to 5000 nucleotides in length and having at least 75% identity to SEQ ID NO:1.

The filler or stuffer can comprise additional elements, such as an exogenous nucleic acid. As used herein, "exogenous nucleic acid" refers to a nucleic acid or an oligonucleotide, either natural or synthetic, which may or may not be naturally found in cells or in a subject/mammal. Typically, an exogenous nucleic acid is a nucleic acid having a sequence or function distinct from the filler or stuffer sequence. To illustrate, an example of "exogenous nucleic acid" is the introduction of all or only part of a gene to create a recombinant gene, such as combining a promoter with a coding sequence via recombinant cloning techniques.

An "exogenous nucleic acid" includes heterologous nucleic acids. A "heterologous nucleic acid" is a nucleic acid that can be inserted into a vector for purposes of vector (e.g., AAV) mediated transfer/delivery of the nucleic acid sequence into a cell, tissue or organism such as a mammal. Once transferred/delivered into the cell, a heterologous nucleic acid, contained within the virion (e.g., AAV), can be expressed (e.g., transcribed, and translated if appropriate). Alternatively, a transferred/delivered heterologous nucleic acid in a cell, contained within the virion, need not be expressed.

The heterologous nucleic acid can encode a polypeptide or protein or an antisense RNA, for example. The heterologous nucleic acid can be of natural origin, such as a nucleic acid that encodes a naturally occurring protein, or a derivative or variant that differs from the naturally occurring counterpart and/or that encodes a protein distinct from a naturally occurring protein. Although the term "heterologous" is not always used herein in reference to nucleic acids and polynucleotides, reference to a nucleic acids and polynucleotide even in the absence of the modifier "heterologous" is intended to include heterologous nucleic acids and polynucleotides in spite of the omission.

The filler or stuffer can therefore further comprise a heterologous nucleic acid.

When a heterologous nucleic acid sequence is present in a vector, the sequence is distinct from the vector, such as a viral (e.g., AAV) vector. Thus, in the example of AAV, a heterologous nucleic acid sequence means a sequence not naturally found in AAV, i.e., is "non-native" with respect to viral (e.g., AAV) nucleic acid. Accordingly, a heterologous nucleic acid sequence need not be heterologous with respect to the subject or mammal to which it is administered, or the transduced or transfected cell.

A heterologous nucleic acid can be a "transgene," which refers to a gene that has been introduced into the genome of a cell by transfection or transduction. Transgenes include, for example, DNA that is either heterologous or homologous to the DNA of a particular cell to be transformed. Additionally, transgenes may include native genes inserted into a non-native organism, or chimeric genes. An "endogenous gene" refers to a native gene in its natural location in the genome of an organism.

The terms "nucleic acid" and "polynucleotide" are used interchangeably herein to refer to all forms of nucleic acid, polynucleotides, oligonucleotides, primers which are polymers of deoxyribonucleic acid (DNA) and ribonucleic acid (RNA). The term "nucleic acid" and "polynucleotide" include genomic DNA, cDNA and antisense DNA, and spliced or unspliced mRNA, rRNA tRNA and inhibitory DNA or RNA (RNAi, e.g., small or short hairpin (sh)RNA, microRNA (miRNA), small or short interfering (si)RNA, trans-splicing RNA, or antisense RNA). Nucleic acids and polynucleotides include naturally occurring, synthetic, and intentionally altered or modified nucleic acid sequences as well as analogues and derivatives. Nucleic acids and polynucleotides can be single, double, or triplex, linear or circular, and can be of any length. In discussing nucleic acids and polynucleotides, a sequence or structure of a particular nucleic acid sequence may be described herein according to the convention of providing the sequence in the 5' to 3' direction.

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

The term "gene" is used broadly to refer to any segment of nucleic acid associated with a biological function. Thus, genes include coding sequences and/or the regulatory sequences required for their expression. For example, "gene" refers to a nucleic acid fragment that expresses mRNA, functional RNA, or specific protein. "Genes" also include nonexpressed DNA segments that, for example, form recognition sequences for other proteins. "Genes" can be obtained from a variety of sources, including cloning from a source of interest or synthesizing from known or predicted sequence information, and may include sequences designed to have desired parameters. An "allele" is one of several alternative forms of a gene occupying a given locus on a chromosome.

The terms "nucleic acid," "nucleic acid sequence or segment," or "polynucleotide" are used interchangeably and may also be used interchangeably with gene, cDNA, DNA and RNA encoded by a gene.

The filler or stuffer can therefore further comprise a transgene.

The invention filler/stuffer sequences alone, or in combination with heterologous nucleic acid sequences and other elements as set forth herein, such as vectors, expression control elements and additional elements, can be isolated or substantially purified. In the context of the invention, an "isolated" or "purified" molecule is made by the hand of man or exists apart from its native environment and is therefore not a product of nature. Generally, isolated molecules may exist in a purified form or in a non-native environment such as, for example, a transgenic host cell. For example, an "isolated" or "purified" filler/stuffer sequence is substantially free of other cellular material, or culture medium when produced by recombinant techniques, or substantially free of chemical precursors or other chemicals when chemically synthesized, or substantially free of one or more materials with which they normally associate with in nature, for example, one or more protein, nucleic acid, lipid, carbohydrate, cell membrane.

The term "isolated" does not exclude combinations produced by the hand of man, for example, a recombinant vector (e.g., rAAV), or virus particle that packages a vector genome and a pharmaceutical formulation. The term "isolated" also does not exclude alternative physical forms of the composition, such as hybrids/chimeras, multimers/oligomers, modifications (e.g., phosphorylation, glycosylation, lipidation) or derivatized forms, or forms expressed in host cells produced by the hand of man.

Heterologous nucleic acids also include, for example, a non-naturally occurring nucleic acid that can be transcribed into inhibitory (e.g., anti-sense) nucleic acid that reduces or inhibits expression of an undesirable or defective (e.g., pathologic) gene.

The filler or stuffer can further comprise a vector, such as a viral, e.g., AAV vector.

The term "vector" includes, inter alia, a plasmid, virus (e.g., AAV vector), cosmid, or other vehicle in double or single stranded linear or circular form that can be manipulated by insertion or incorporation of a nucleic acid. A "vector" can introduce/transfer nucleic acid sequences into a prokaryotic or eukaryotic host, such as cells of a mammal, either by integration into the cellular genome or extrachromosomally (e.g., autonomous replicating plasmid with an origin of replication). Vectors can be used to transcribe or translate the introduced/transferred nucleic acid in cells. Vectors can also be used for genetic manipulation (i.e., "cloning vectors"). A vector or plasmid generally contains at least an origin of replication for propagation in a cell and optionally additional elements. Optional elements include but are not limited to a heterologous nucleic acid sequence, expression control element (e.g., a promoter, enhancer), selectable marker (e.g., antibiotic resistance), transcription termination signals (poly-adenylation sequence), translation stop signals (stop codons).

As used herein, the term "recombinant," as a modifier of a vector such as a viral (e.g., AAV) vector, as well as a modifier of sequences such as "recombinant" nucleic acid sequences and polypeptides, means that the compositions have been manipulated (i.e., engineered) in a fashion that generally does not occur in nature. A nucleic acid sequence example of a recombinant vector, such as AAV vector would be where a nucleic acid sequence that is not normally present in the wild-type viral (e.g., AAV) genome is within the viral (e.g., AAV) particle and/or viral (e.g., AAV) genome. Although the term "recombinant" is not always used herein in reference to vectors such as viral (e.g., AAV) vectors, as well as sequences such as nucleic acid sequences and polypeptides, hybrids and chimeras, recombinant forms of vectors (e.g., AAV), and sequences including nucleic acids, nucleic acid sequences and polypeptides, hybrids and chimeras, are expressly included in spite of any such omission.

In particular embodiments, a recombinant vector (e.g., AAV) is a parvovirus vector. Parvoviruses are small viruses with a single-stranded DNA genome. "Adeno-associated viruses" (AAV) are in the parvovirus family.

Parvoviruses including AAV are viruses useful as gene therapy vectors as they can penetrate cells and introduce nucleic acid/genetic material. AAV can penetrate cells and introduce nucleic acid/genetic material so that the nucleic acid/genetic material is stably maintained in cells. In addition, these viruses can introduce nucleic acid/genetic material into specific sites, for example, such as a specific site on chromosome 19. Because AAV are not associated with pathogenic disease in humans, AAV vectors are able to deliver heterologous nucleic acid sequences (e.g., therapeutic proteins and agents) to human patients without causing substantial AAV pathogenesis or disease.

An "AAV virus" or "AAV viral particle" refers to a viral particle composed of at least one AAV capsid protein (or optionally all of the three AAV capsid proteins, VP1, VP2 and VP3) and an encapsidated nucleic acid. If the particle encapsidates a heterologous nucleic acid (i.e., a non-native sequence other than a wild-type AAV genome such as a transgene to be delivered to a cell), it is typically referred to as "rAAV." Incorporation of a heterologous nucleic acid sequence therefore defines the viral vector (e.g., AAV) as a "recombinant" vector, which in the case of AAV the particle can be referred to as a "rAAV." Or as an "rAAV vector."

A recombinant viral vector, such as "AAV vector" is derived from the wild type genome of a virus, such as AAV by using molecular methods to remove the wild type genome from the virus (e.g., AAV), and replacing with a non-native nucleic acid, such as a heterologous nucleic acid sequence (e.g., a therapeutic gene). Typically, for AAV one or both inverted terminal repeat (ITR) sequences of the wild type AAV genome are retained in the AAV vector. A viral vector (e.g., AAV) is distinguished from a viral (e.g., AAV) genome, since all or a part of the viral genome has been replaced with a heterologous nucleic acid sequence, which heterologous sequence is typically a non-native nucleic acid with respect to the viral (e.g., AAV) genomic nucleic acid.

An "AAV ITR" is a region found at each end of the AAV genome which functions together in cis as origins of DNA replication and as packaging signals for the virus. AAV ITRs, together with AAV rep coding region, provide for the efficient excision and rescue from, and integration of a nucleic acid sequence positioned between two flanking ITRs into a mammalian cell genome.

Such recombinant vectors include vectors (e.g., rAAV) with a filler or stuffer sequence having a size at, approaching or slightly greater in length than the natural packaging capacity of the virus (AAV), and methods of using such recombinant vectors (e.g., rAAV), for example, to produce recombinant virus particles having reduced or eliminated residual DNA impurities.

For a recombinant vector, a vector genome refers to the portion of the vector plasmid that is packaged or encapsidated by virus (e.g., AAV), which contains the heterologous nucleic acid sequence. The plasmid portion of the recombinant vector includes the backbone used for helper cell transfection and cell production of virus that packages/encapsidates the vector genome, but is not itself packaged or encapsidated by virus (e.g., AAV).

Recombinant vectors as set forth herein include an additional filler or stuffer nucleic acid sequence that resizes or adjusts the length to near or at the normal size of the virus genomic sequence that is packaged or encapsidated to form infectious virus particles. In various embodiments, a filler or stuffer nucleic acid sequence is an untranslated (non-protein encoding) segment of nucleic acid. In particular embodiments of an AAV vector, a vector sequence has a length less than 4.7 Kb and the filler or stuffer sequence has a length that when combined (e.g., inserted into a vector) with the vector sequence has a total length ranging from about 3.0-5.5 Kb, or ranging from about 4.0-5.0 Kb, or ranging from about 4.3-4.8 Kb. For example, length of a vector for AAV particle packaging can be up to about 5.2 kb.

In various embodiments, in the context of an AAV vector a filler or stuffer nucleic acid sequence has a sequence length in a range of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, or 5,500-6,000 contiguous nucleotides in length.

In additional embodiments, a filler or stuffer nucleic acid sequence has a length which corresponds to a contiguous portion of a reference sequence e.g., SEQ ID NO:1. In particular aspects, a filler or stuffer nucleic acid has from 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-4,600 nucleotides that correspond to a sequence of or having SEQ ID NO:1.

As set forth herein, a "variant" filler or stuffer sequence is a sequence that is distinct from but substantially similar to the sequence of SEQ ID NO:1. Generally, filler or stuffer sequence variants of the invention will have at least 40%, 50%, 60% to 70%, e.g., 71%, 72%, 73%, 74%, 75%, 76%, 77%, 78%, to 79%, or at least 80%, e.g., 81%-84%, at least 85%, e.g., 85%, 86%, 87%, 88%, 89%, 90%, 91%, 92%, 93%, 94%, 95%, 96%, 97%, 98% or 99% sequence identity to SEQ ID NO:1. In various embodiments, a filler or stuffer sequence will be at least about 50% identical, more typically about 70% identical, even more typically about 80% identical (90% or more identity) to the reference sequence e.g., SEQ ID NO:1. In other embodiments, filler or stuffer sequences have at least 60%, 70%, 75% or more identity (e.g., 80%, 85% 90%, 95%, 96%, 97%, 98%, 99% or more identity) to a reference sequence e.g., SEQ ID NO:1.

As disclosed herein, the filler or stuffer nucleic acid sequence can be located within the recombinant vector, relative to other sequences, such as the heterologous nucleic acid sequence, control element(s), ITR(s), origin of replication, selectable marker, etc., compatible with vector function. In a particular aspect, a filler or stuffer nucleic acid sequence is positioned between a 5' and a 3' ITR that flanks the respective 5' or 3' termini of the heterologous nucleic acid sequence, e.g., in the context of AAV vector the filler or stuffer nucleic acid sequence is present in the vector genome portion and is therefore available for virus packaging/encapsidation. In another particular aspect, a filler or stuffer nucleic acid sequence is positioned at either the 5' or 3' termini, or positioned within the heterologous nucleic acid sequence, e.g., in the context of AAV vector the filler or stuffer nucleic acid sequence positioned at either the 5' or 3' termini, or positioned within the heterologous nucleic acid sequence is present in the vector genome portion and is therefore available for virus packaging/encapsidation.

Filler or stuffer nucleic acid sequences of the invention can include still additional nucleic acid elements. These elements include, without limitation one or more copies of an AAV ITR sequence, an expression control elements such as a promoter and/or enhancer element, a transcription termination signal, 5' or 3' untranslated regions (e.g., poly-adenylation sequences) which flank a heterologous nucleic acid sequence, or all or a portion of an intron. Such elements also optionally include a transcription termination signal, such as a poly-adenylation sequence. Filler or stuffer nucleic acid sequences of the invention including one or more of the foregoing additional nucleic acid elements can be included in recombinant AAV vectors.

The filler or stuffer can further comprise an exogenous (heterologous) nucleic acid operably linked to an expression control element.

Expression control elements are regulatory sequences that may be present within a vector to facilitate proper heterologous nucleic acid transcription and if appropriate translation (e.g., splicing signal for introns, maintenance of the correct reading frame of the gene to permit in-frame translation of mRNA and, stop codons etc.). Typically, expression control elements are nucleic acid sequence(s), such as promoters and enhancers that influence transcription, RNA processing or stability, or translation of the associated coding sequence and therefore expression of an operably linked heterologous nucleic acid. Such elements typically act in cis but may also act in trans. Such elements, where known, are typically absent from the stuffer or filler sequence.

Expression control can be effected at the level of transcription, translation, splicing, message stability, etc. Typically, an expression control element that modulates transcription is juxtaposed near the 5' end of the transcribed nucleic acid (i.e., "upstream"). Expression control elements can also be located at the 3' end of the transcribed sequence (i.e., "downstream") or within the transcript (e.g., in an intron). Expression control elements can be located at a distance away from the transcribed sequence (e.g., 100 to 500, 500 to 1000, 2000 to 5000, or more nucleotides from the nucleic acid sequence), even at considerable distances. Nevertheless, owing to the length limitations for viral vectors, such as AAV vectors, such expression control elements will typically be within 1 to 1000 nucleotides from the nucleic acid.

Functionally, expression of operably linked heterologous nucleic acid is at least in part controllable by the element (e.g., promoter) such that the element modulates transcription of the heterologous nucleic acid sequence and, as appropriate, translation of the transcript. A specific example of an expression control element is a promoter, which is usually located 5' of the transcribed sequence. Another example of an expression control element is an enhancer, which can be located 5', 3' of the transcribed sequence, or within the transcribed sequence.

Expression control elements include natural and synthetic sequences as well as sequences that may be a combination of synthetic and natural sequences. The term is not exclusive to promoters.

The term "promoter" as used herein refers to a nucleotide sequence, such as a DNA sequence that is typically located adjacent to a heterologous nucleic acid sequence, usually upstream (5') to the sequence. A promoter is operatively linked to the adjacent sequence, e.g., heterologous nucleic acid. A promoter typically increases an amount expressed from a heterologous nucleic acid as compared to an amount expressed when no promoter exists.

A "promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of the heterologous nucleic acid. This type of promoter sequence may include proximal and more distal upstream elements.

The term "enhancer" as used herein can refer to a sequence that is located adjacent to the heterologous nucleic acid. Enhancer elements are typically located upstream of a promoter element but also function and can be located downstream of or within a DNA sequence (e.g., a heterologous nucleic acid). Hence, an enhancer element can be located 100 base pairs, 200 base pairs, or 300 or more base pairs upstream or downstream of a heterologous nucleic acid. An enhancer may also be an innate element of a promoter. Enhancers are often capable of operating in both orientations, either upstream or downstream from the promoter. Enhancers typically increase expression of a heterologous nucleic acid above increased expression afforded by a promoter element.

Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

Expression control elements (e.g., promoters) include those active in a particular tissue or cell type, referred to herein as a "tissue-specific expression control elements/promoters." Tissue-specific expression control elements are typically active in specific cell or tissue (e.g., active in brain, central nervous system, spinal cord, liver, eye, retina, bone, muscle, lung, pancreas, heart, kidney cell, etc.). Expression control elements are typically active in these cells, tissues or organs because they are recognized by transcriptional activator proteins, or other regulators of transcription, that are unique to a specific cell, tissue or organ type. Examples of CNS-specific promoters include those isolated from the genes myelin basic protein (MBP), glial fibrillary acid protein (GFAP), and neuron specific enolase (NSE).

Expression control elements also include ubiquitous or promiscuous promoters/enhancers which are capable of driving expression of a nucleic acid sequence in many different cell types. Such elements include, but are not limited to the cytomegalovirus (CMV) immediate early promoter/enhancer sequences, the Rous sarcoma virus (RSV) promoter/enhancer sequences and the other viral promoters/enhancers active in a variety of mammalian cell types, or synthetic elements that are not present in nature (see, e.g., Boshart et al, Cell, 41:521-530 (1985)), the SV40 promoter, the dihydrofolate reductase promoter, the cytoplasmic β-actin promoter and the phosphoglycerol kinase (PGK) promoter. Further non-limiting examples of promoters useful in the invention include mouse U6 RNA promoters, synthetic human H1RNA promoters, RNA polymerase II and RNA polymerase III promoters.

Expression control elements also can confer expression in a manner that is regulatable, that is, a signal or stimuli increases or decreases expression of the operably linked heterologous nucleic acid. A regulatable element that increases expression of the heterologous nucleic acid in response to a signal or stimuli is also referred to as an "inducible element" (i.e., is induced by a signal).

Expression control elements also include native elements(s) for the heterologous nucleic acid. A native control element (e.g., promoter) may be used when it is desired that expression of the heterologous nucleic acid should mimic the native expression. The native element may be used when expression of the heterologous nucleic acid is to be regulated temporally or developmentally, or in a tissue-specific manner, or in response to specific transcriptional stimuli. Other native expression control elements, such as introns, polyadenylation sites or Kozak consensus sequences may also be used.

The term "operable linkage" or "operably linked" refers to a physical or functional juxtaposition of the components so described as to permit them to function in their intended manner. In the example of an expression control element in operable linkage with a heterologous nucleic acid, the relationship is such that the control element modulates expression of the heterologous nucleic acid. More specifically, for example, two DNA sequences operably linked means that the two DNAs are arranged (cis or trans) in such a relationship that at least one of the DNA sequences is able to exert a physiological effect upon the other sequence.

Filler or stuffer nucleic acid sequences of the invention can include still additional elements such as introns, which introns may be associated with the same gene or a completely different gene or other DNA sequence. Accordingly, other untranslated (non-protein encoding) regions of nucleic acid, such as introns found in genomic sequences from cognate (related) genes (the heterologous nucleic acid sequence encodes all or a portion of same protein encoded by the genomic sequence) and non-cognate (unrelated) genes (the heterologous nucleic acid sequence encodes a protein that is distinct from the protein encoded by the genomic sequence) can be included with filler or stuffer nucleic acid sequences and in turn included in vectors of the invention.

The phrase "specifically hybridize" refers to the association between two single-stranded nucleic acid molecules of sufficiently complementary sequence to permit hybridization under pre-determined conditions generally used in the art (sometimes termed "substantially complementary"). In particular, the term refers to hybridization of two nucleic acid sequences with substantially complementary sequences, to the substantial exclusion of hybridization with other single-stranded non-complementary nucleic acid sequences.

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

As noted herein, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization such as Southern and Northern hybridizations are sequence dependent. Longer sequences hybridize specifically at higher temperatures. The Tm is the temperature (under defined ionic strength and pH) at which 50% of the target sequence hybridizes to a perfectly matched probe. Specificity is typically the function of post-hybridization washes, factors being the ionic strength and temperature of the final wash solution. For DNA-DNA hybrids, the Tm can be approximated from the equation: Tm 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. Tm is reduced by about 1° C. for each 1% of mismatching; thus, Tm, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), the SSC concentration can be increased so that a higher temperature can be used. Generally, highly stringent hybridization and wash conditions are selected to be about 5° C. lower than the thermal melting point (Tm) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook and Russell 2001, for a description of SSC buffer). Often, a high stringency wash is preceded by a low stringency wash to remove background probe signal. For short nucleic acid sequences (e.g., about 10 to 50 nucleotides), stringent conditions typically involve salt concentrations of less than about 1.5 M, or about 0.01 to 1.0 M, Na ion concentration (or other salts) at pH 7.0 to 8.3, and the temperature is typically at least about 30° C. Stringent conditions may also be achieved with the addition of destabilizing agents such as formamide. In general, a signal to noise ratio of 2× (or higher) than that observed for an unrelated probe in the particular hybridization assay indicates detection of a specific hybridization. Very stringent conditions are selected to be equal to the Tm for a particular nucleic acid molecule.

Nucleic acid and polypeptides including modified forms can be made using various standard cloning, recombinant DNA technology, via cell expression or in vitro translation and chemical synthesis techniques. Purity of nucleic acid can be determined through sequencing, gel electrophoresis and the like. For example, nucleic acids can be isolated using hybridization or computer-based database screening techniques. Such techniques include, but are not limited to: (1) hybridization of genomic DNA or cDNA libraries with probes to detect homologous nucleotide sequences; (2) antibody screening to detect polypeptides having shared structural features, for example, using an expression library; (3) polymerase chain reaction (PCR) on genomic DNA or cDNA using primers capable of annealing to a nucleic acid sequence of interest; (4) computer searches of sequence databases for related sequences; and (5) differential screening of a subtracted nucleic acid library.

A "selectable marker" refers to a gene that when expressed confers a selectable phenotype, such as antibiotic resistance (e.g., kanamycin), on a transformed cell. A "reporter" gene is one that provides a detectable signal. A non-limiting example of a reporter gene is the luciferase gene.

As disclosed herein, AAV vectors typically accept inserts of DNA having a defined size range which is generally about 4 kb to about 5.2 kb, or slightly more. When there are shorter heterologous sequences in the vector, inclusion of a stuffer or filler in the insert fragment (e.g., vector genome) will provide a length acceptable for AAV vector packaging.

Thus, in accordance with the invention vectors in which there is included a stuffer or filler in the packaged (encapsidated) portion (vector genome) to provide a size approaching the natural packaging capacity of the virus (e.g., AAV) are provided. Such vectors as set forth herein can further include heterologous nucleic acid sequences encoding peptides and proteins, or heterologous nucleic acid sequences which directly or when transcribed comprise inhibitory nucleic acids that target genes for inhibition of expression or function, are provided. In addition, such vector genomes can be included (packaged) within a virus, such as an adeno-associated virus (e.g., AAV), which is also referred to herein as a "particle" or "virion" for subsequent infection (transformation) of a cell, ex vivo, in vitro or in vivo.

Such particles or virions will typically include proteins that encapsidate or package the vector genome. Particular examples include viral envelope proteins, and capsid proteins in the case of AAV.

Such vectors (e.g., AAV), and particles (e.g., AAV) including such vector genomes, include any virus strain or serotype, and subgroups and variants thereof. As used herein, the term "serotype" is a distinction used to refer to a virus (e.g., AAV) having a capsid that is serologically distinct from other virus (e.g., AAV) serotypes.

A "serotype" is traditionally defined on the basis of a lack of cross-reactivity between antibodies to one virus as compared to another virus. Such cross-reactivity differences are usually due to differences in capsid protein sequences/antigenic determinants (e.g., due to VP1, VP2, and/or VP3 sequence differences of AAV serotypes). Under the traditional definition, a serotype means that the virus of interest has been tested against serum specific for all existing and characterized serotypes for neutralizing activity and no antibodies have been found that neutralize the virus of interest. As more naturally occurring virus isolates of are discovered and/or capsid mutants generated, there may or may not be serological differences with any of the currently existing serotypes. Thus, in cases where the new virus (e.g., AAV) has no serological difference, this new virus (e.g., AAV) would be a subgroup or variant of the corresponding serotype. In many cases, serology testing for neutralizing activity has yet to be performed on mutant viruses with capsid sequence modifications to determine if they are of another serotype according to the traditional definition of serotype. Accordingly, for the sake of convenience and to avoid repetition, the term "serotype" broadly refers to both serologically distinct viruses (e.g., AAV) as well as viruses (e.g., AAV) that are not serologically distinct that may be within a subgroup or a variant of a given serotype.

By way of a non-limiting example, AAV include various naturally and non-naturally occurring serotypes. Such non-limiting serotypes include, for example, AAV-1, -2, -3, -4, -5, -6, -7, -8, -9, -10, -11, -rh74, -rh10 and AAV-2i8. Again, for the sake of convenience serotypes include AAV with capsid sequence modifications that have not been fully characterized as being a distinct serotype, and may in fact actually constitute a subgroup or variant of a known serotype.

Accordingly, invention recombinant vector (e.g., AAV), and particles that include packaged or encapsidated vector genomes, as well as methods and uses thereof, include any viral strain or serotype. As a non-limiting example, a recombinant vector (e.g., AAV) can be based upon any AAV genome, such as AAV-1, -2, -3, -4, -5, -6, -7, -8, -9, -10, -11, -rh74, -rh10 or AAV-2i8, for example. A particle (virus) that packages (also referred to as encapsidates) a recombinant vector (e.g., AAV) genome can be based upon any AAV serotype such as AAV-1, -2, -3, -4, -5, -6, -7, -8, -9, -10, -11, -rh74, -rh10 or AAV-2i8, for example.

Such vectors and particles can be based on the same of strain or serotype (or subgroup or variant), or be different from each other. As a non-limiting example, a recombinant vector (e.g., AAV) plasmid based upon AAV2 serotype genome (e.g., AAV2 ITRs) can be identical to one or more of the capsid proteins that package the vector, in which case at least one of the three VP1, VP2 and VP3 capsid proteins would also be AAV2. In addition, a recombinant vector (e.g., AAV) plasmid based upon AAV2 serotype genome (e.g., AAV2 ITRs) can be distinct serotype from one or more of the capsid proteins that package the vector, in which case at least one of the three capsid proteins could be a non-AAV2 capsid, such as AAV-1, -3, -4, -5, -6, -7, -8, -9, -10, -11, -rh74, -rh10 or AAV-2i8 capsid, for example.

An AAV serotype may be selected/designed according to a desired route of administration, for example, and without limitation, for systemic administration, an AAV vector capable of crossing the blood-brain barrier may be used (e.g., AAV9, or a chimeric AAV vector having AAV9 capsid proteins). The invention also includes compositions, methods and uses in which AAV vector is administered to the bloodstream using serotypes capable of incapable of traversing the blood-brain barrier.

In certain embodiments, recombinant vector (e.g., AAV), and particles with the packaged (encapsidated) portion (vector genome) include hybrids or chimeras. As a non-limiting example, a hybrid vector genome can be a mixed serotype, e.g., one virus genome serotype, such as an AAV2 serotype and a non-AAV2 serotype, for example, an AAV2 flanking (5' or 3') ITR, and a non-AAV2 flanking (5' or 3') ITR. More particularly, as an example, a vector genome that is hybrid AAV serotype, could be an AAV2 flanking (5' or 3') ITR and an AAV-1, -3, -4, -5, -6, -7, -8, -9, -10, -11, -rh74, -rh10 or AAV-2i8 flanking (5' or 3') ITR. As another non-limiting example, a vector can be a hybrid AAV serotype, such as an AAV2 capsid and a non-AAV2 capsid, for example, an AAV2 VP1, VP2 or VP3, and a non-AAV2 VP1, VP2 or VP3. More particularly, a hybrid or chimeric vector genome or virus that is an AAV serotype, could be an AAV2 VP1, VP2 or VP3 and a AAV-1, -3, -4, -5, -6, -7, -8, -9, -10, -11, -rh74, -rh10 or AAV-2i8 VP1, VP2 or VP3.

Recombinant vector (e.g., AAV) (e.g., AAV includes one or more AAV ITRs) and particles (e.g., that include AAV capsid proteins) as set forth herein include those having a filler or stuffer sequence, nucleic acid sequence, polypeptide or subsequence thereof that has less than 100% sequence identity to a reference sequence. In various embodiments, a sequence that has less than 100% sequence identity to a reference sequence is at least 70% or more (e.g., 70-75%, 75-80%, 80-85%, 85-90%, 90-95%, 96%, 97%, 98%, 99%, 99.5%, etc.) identical to a reference sequence, for example, 80% or more (e.g., 80-85%, 85-90%, 90-95%, 96%, 97%, 98%, 99%, 99.5%, etc.) identical to a reference sequence. Reference sequences include the filler or stuffer sequences set forth herein, heterologous nucleic acid sequences, vector sequences, expression control elements, the additional elements that can be included or combined with a vector as set forth herein. Reference sequences include any of AAV1, AAV2, AAV3, AAV4, AAV5, AAV6, AAV7, AAV8, AAV9, AAV10, AAV11, Rh10, Rh74, or AAV-2i8 VP1, VP2, and/or VP3 capsid sequence, or 5' or 3' ITR of AAV1, AAV2, AAV3, AAV4, AAV5, AAV6, AAV7, AAV8, AAV9, AAV10, AAV11, Rh10, Rh74, or AAV-2i8. Such capsid sequences and 5' and 3' ITR for AAV1, AAV2, AAV3, AAV4, AAV5, AAV6, AAV7, AAV8, AAV9, AAV10, AAV11, Rh10, Rh74 and AAV-2i8 are known in the art.

Recombinant vector (e.g., AAV), including AAV1, AAV2, AAV3, AAV4, AAV5, AAV6, AAV7, AAV8, AAV9, AAV10, AAV11, Rh10, Rh74 or AAV-2i8 and related, hybrid and chimeric sequences, can be constructed using recombinant techniques that are known to the skilled artisan, to include a filler or stuffer sequence, one or more heterologous nucleic acid sequences (transgenes) flanked with one or more functional AAV ITR sequences.

Such vector can have one or more of the wild type AAV genes deleted in whole or in part, for example, a rep and/or cap gene, but retain at least one functional flanking ITR sequence, as necessary for the rescue, replication, and packaging of the AAV vector particle. Thus, an AAV vector genome includes sequences required in cis for replication and packaging (e.g., functional ITR sequences).

Recombinant vectors (e.g., AAV) in which the packaged (encapsidated) portion (referred to as the "vector genome" or simply "vector") has a size approaching the natural packaging capacity of the virus (e.g., AAV) can be used to transfer/deliver heterologous nucleic acid sequences, such as coding sequences (genes) for proteins that provide a desirable or therapeutic benefit, as well as inhibitory (e.g., anti-sense) nucleic acid that reduce or inhibit expression of an undesirable or defective (e.g., pathologic) gene, thereby treating a variety of diseases. For example, a recombinant vector (e.g., AAV) in which the packaged (encapsidated) portion (vector genome) has a size approaching the natural packaging capacity of the virus (AAV) can be used to transfer/deliver therapeutic genes to treat a genetic deficiency disease, such as diseases of the central nervous system such as neurodegenerative diseases, including spinocerebellar ataxia and Huntington's disease; metabolic or plasma protein deficiencies; and for other therapeutic purposes.

As set forth herein, recombinant vector (e.g., AAV) can be used to deliver exogenous nucleic acid sequences (e.g., heterologous nucleic acid sequences) to cells ex vivo, in vitro and in vivo. Such heterologous nucleic acid sequences can encode proteins such that the cells into which the nucleic acid is delivered express the encoded proteins. For example, a recombinant vector (e.g., AAV) can include a heterologous nucleic acid sequence encoding a desired (e.g., therapeutic) protein or peptide.

The "polypeptides," "proteins" and "peptides" encoded by "nucleic acid" and "polynucleotide" sequences include full-length native sequences, as with naturally occurring proteins, as well as functional subsequences, modified forms or sequence variants so long as the subsequence, modified form or variant retains some degree of functionality of the native full-length protein. In various embodiments of the invention, such polypeptides, proteins and peptides encoded by the nucleic acid sequences can be but are not required to be identical to the endogenous protein that is defective, or whose expression is insufficient, or deficient in the treated mammal.

In addition, a recombinant vector (e.g., AAV) can include a heterologous nucleic acid sequence that when transcribed comprises an inhibitory sequence (e.g., RNA), for example, a sequence that targets a gene (or gene transcript) for inhibition of expression. Vector delivery or administration to a subject (e.g., mammal) therefore provides not only nucleic acid sequences encoding proteins and peptides to the subject, but also inhibitory nucleic acids that target genes for inhibition of expression or function in the subject.

Invention recombinant vector (e.g., AAV) can be used to introduce/deliver nucleic acid sequences stably or transiently into cells and progeny thereof. As set forth herein, a "transgene" refers to a heterologous nucleic acid sequence that has been introduced into a cell or organism.

For example, in a cell having a transgene, the transgene has been introduced/transferred by way of vector (e.g., AAV) "transduced" into the cell. The terms "transduce" and "transfect" refer to introduction of a molecule such as a filler or stuffer sequence alone or in combination with other elements, such as a heterologous nucleic acid, vector, etc., into a cell or host organism. The term "transduction" is generally used to refer to infecting cells with viral particles. The term "transfection" is generally used to refer to the delivery of DNA into eukaryotic (e.g., mammalian) cells. Accordingly, a "transduced" or "transfected" cell (e.g., in a mammal, or a cell or tissue or organ), means a genetic change in a cell following incorporation of an exogenous molecule, for example, a heterologous nucleic acid sequence (e.g., a transgene) or protein into the cell. A "transduced" or "transfected" cell can be a cell into which, or a progeny thereof, in which an exogenous molecule has been introduced, for example. The cell(s) can be propagated and the introduced protein expressed, or heterologous nucleic acid transcribed. For gene therapy uses and methods, a transduced or transfected cell can be in a subject such as a mammal. Typically, introduction into host cells is by way of a vector.

Filler or stuffer sequences, heterologous nucleic acids, polypeptides and subsequences thereof include modified and variant forms. The terms "modify" or "variant" and grammatical variations thereof used in such a context, mean that a nucleic acid, polypeptide or subsequence thereof deviates from a reference sequence. Modified and variant sequences may therefore have substantially the same, greater or less activity or function than a reference sequence, but at least retain partial activity or function of the reference sequence. Naturally occurring polymorphic sequences that retain at least partial function are typically not considered modified or variant since they occur in nature.

The invention therefore also includes naturally occurring and non-naturally occurring variants. Such variants include gain and loss of activity and/or function variants.

Non-limiting examples of modifications include one or more nucleotide or amino acid substitutions (e.g., 1-3, 3-5, 5-10, 10-15, 15-20, 20-25, 25-30, 30-40, 40-50, 50-100, or more nucleotides or residues), additions (e.g., insertions or 1-3, 3-5, 5-10, 10-15, 15-20, 20-25, 25-30, 30-40, 40-50, 50-100, or more nucleotides or residues) and deletions (e.g., subsequences or fragments) of a reference sequence. In particular embodiments, a modified or variant sequence retains at least part of a function or an activity of unmodified sequence. Such modified forms and variants can have less than, the same, or greater, but at least a part of, a function or activity of a reference sequence, for example, as described herein.

A variant can have one or more non-conservative or a conservative amino acid sequence differences or modifications, or both. A "conservative substitution" is the replacement of one amino acid by a biologically, chemically or structurally similar residue. Biologically similar means that the substitution does not destroy a biological activity. Structurally similar means that the amino acids have side chains with similar length, such as alanine, glycine and serine, or a similar size. Chemical similarity means that the residues either have the same charge or are both hydrophilic or are both hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like. Particular examples of conservative substitutions include the substitution of a hydrophobic residue such as isoleucine, valine, leucine or methionine for another, the substitution of a polar residue for another, such as the substitution of arginine for lysine, glutamic for aspartic acids, or glutamine for asparagine, and the like. For example, conservative amino acid substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. A "conservative substitution" also includes the use of a substituted amino acid in place of an unsubstituted parent amino acid.

Such variants may be modified using recombinant DNA technology such that the nucleic acid, protein or polypeptide possesses altered or additional properties, for example, variants conferring enhanced protein stability or enhanced activity of the protein. Variants can differ from a reference sequence, such as naturally occurring nucleic acid sequences, proteins or peptides.

At the nucleotide sequence level, a variant will typically be at least about 50% identical, more typically about 70% identical, even more typically about 80% identical (90% or more identity) to the reference sequence. At the amino acid sequence level, a naturally and non-naturally occurring variant protein will typically be at least about 70% identical, more typically about 80% identical, even more typically about 90% or more identity to the reference protein, although substantial regions of non-identity are permitted in non-conserved regions (e.g., less, than 70% identical, such as less than 60%, 50% or even 40%). In other embodiments, the sequences have at least 60%, 70%, 75% or more identity (e.g., 80%, 85% 90%, 95%, 96%, 97%, 98%, 99% or more identity) to a reference sequence. Procedures for introduction of nucleotide and amino acid changes in a nucleic acid, protein or polypeptide are known to the skilled artisan (see, e.g., Sambrook et al., *Molecular Cloning: A Laboratory Manual* (2007)).

The term "identity," "homology" and grammatical variations thereof, mean that two or more referenced entities are the same, when they are "aligned" sequences. Thus, by way of example, when two polypeptide sequences are identical, they have the same amino acid sequence, at least within the referenced region or portion. Where two nucleic acid sequences are identical, they have the same nucleic acid sequence, at least within the referenced region or portion. The identity can be over a defined area (region or domain) of the sequence. An "area" or "region" of identity refers to a portion of two or more referenced entities that are the same. Thus, where two protein or nucleic acid sequences are identical over one or more sequence areas or regions they share identity within that region. An "aligned" sequence refers to multiple nucleic acid or protein (amino acid) sequences, often containing corrections for missing or additional bases or amino acids (gaps) as compared to a reference sequence.

The identity can extend over the entire sequence length or a portion of the sequence. In particular aspects, the length of the sequence sharing the percent (%) identity is, e.g., 5, 6, 7, 8, 9, 10, 11, 12, 13, 14, 15, 16, 17, 18, 19, 20, etc. contiguous amino acids. In additional particular aspects, the length of the sequence sharing identity is 20 or more contiguous nucleic acids or amino acids, e.g., 20, 21, 22, 23, 24, 25, 26, 27, 28, 29, 30, 31, 32, 33, 34, 35, etc. contiguous nucleic acids or amino acids. In further particular aspects, the length of the sequence sharing identity is 35 or more contiguous nucleic acids or amino acids, e.g., 35, 36, 37, 38, 39, 40, 41, 42, 43, 44, 45, 45, 47, 48, 49, 50, etc., contiguous nucleic acids or amino acids. In yet further particular aspects, the length of the sequence sharing identity is 50 or more contiguous nucleic acids or amino acids, e.g., 50-55, 55-60, 60-65, 65-70, 70-75, 75-80, 80-85, 85-90, 90-95, 95-100, 100-110, etc. contiguous nucleic acids or amino acids.

The terms "homologous" or "homology" mean that two or more referenced entities share at least partial identity over a given region or portion. "Areas, regions or domains" of homology or identity mean that a portion of two or more referenced entities share homology or are the same. Thus, where two sequences are identical over one or more sequence regions they share identity in these regions. "Substantial homology" means that a molecule is structurally or functionally conserved such that it has or is predicted to have at least partial structure or function of one or more of the structures or functions (e.g., a biological function or activity) of the reference molecule, or relevant/corresponding region or portion of the reference molecule to which it shares homology.

The extent of identity (homology) between two sequences can be ascertained using a computer program and mathematical algorithm. Such algorithms that calculate percent (%) sequence identity (homology) generally account for sequence gaps and mismatches over the comparison region or area. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch—2; gap open 5; gap extension 2. For polypeptide sequence comparisons, a BLASTP algorithm is typically used in combination with a scoring matrix, such as PAM100, PAM 250, BLOSUM 62 or BLOSUM 50. Additional implementations include, but are not limited to: CLUSTAL in the PC/Gene program (available from Intelligenetics, Mountain View, Calif.); the ALIGN program (Version 2.0) and GAP, BESTFIT, FASTA (e.g., FASTA2 and FASTA3), and TFASTA in the Wisconsin Genetics Software Package, Version 8 (available from Genetics Computer Group (GCG), 575 Science Drive, Madison, Wis., USA). SSEARCH sequence comparison programs are also used to quantitate extent of identity (Pearson et al., *Proc. Natl. Acad. Sci.* USA 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)). Alignments using these programs can be performed using the default parameters.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g. BLASTN for nucleotide sequences) can be used. The BLASTN program (for nucleotide sequences) uses as defaults a wordlength (W) of 11, an expectation (E) of 10, a cutoff of 100, M=5, N=−4, and a comparison of both strands. Alignment may also be performed manually by inspection.

Nucleic acids and polypeptides including modified forms can also be produced by chemical synthesis using methods known to the skilled artisan, for example, an automated synthesis apparatus (see, e.g., Applied Biosystems, Foster City, Calif.). Peptides can be synthesized, whole or in part, using chemical methods (see, e.g., Caruthers (1980). *Nucleic Acids Res. Symp. Ser.* 215; Horn (1980); and Banga, A. K., *Therapeutic Peptides and Proteins, Formulation, Processing and Delivery Systems* (1995) Technomic Publishing Co., Lancaster, Pa.). Peptide synthesis can be performed using various solid phase techniques (see, e.g., Roberge *Science* 269:202 (1995); Merrifield, *Methods Enzymol.* 289:3

(1997)) and automated synthesis may be achieved, e.g., using the ABI 431A Peptide Synthesizer (Perkin Elmer) in accordance with the manufacturer's instructions.

The term "consists essentially of" or "consisting essentially of" when referring to a particular nucleic acid sequence or amino acid sequence means a sequence having the properties of a given sequence, e.g., a stuffer or filler as set forth herein. For example, when used in reference to an nucleic acid sequence, the phrase includes the sequence per se and molecular modifications that would not affect the basic and novel characteristics of the sequence.

The invention provides methods of delivering a heterologous nucleic acid to a cell. In one embodiment, a method includes administering to the cell an AAV particle containing a vector comprising a filler or stuffer sequence and a heterologous nucleic acid inserted between a pair of AAV inverted terminal repeats, thereby delivering the nucleic acid to the cell. Administration to the cell can be accomplished by any means. The particle can be allowed to remain in contact with the cells for any desired length of time. For in vitro methods, the AAV vector can be administered to the cell by standard viral transduction methods. For example, cells can be transduced in vitro by combining recombinant AAV vector with CNS cells e.g., in appropriate media, and screening for those cells harboring the DNA of interest using conventional techniques. Transduced cells can then be formulated into pharmaceutical compositions, described more fully below, and the composition introduced into the subject by various techniques.

Titers of AAV vector to administer can vary, particularly depending upon the cell type, but will be typical of that used for AAV transduction in general. The cells can include any desired cell in humans as well as other large (e.g., non-rodent) mammals, such as primates, horse, sheep, goat, pig, and dog.

Transduced and transfected cells may be produced using a variety of methods. Physical methods include calcium phosphate precipitation, lipofection, particle bombardment, microinjection, electroporation, and the like. Biological methods include the use of DNA (e.g., AAV) and RNA viral vectors. For mammalian gene therapy, as described herein, it is desirable to use an efficient means of inserting a transgene into the host genome. Viral vectors, and especially AAV and lentiviral vectors, have become the most widely used method for inserting genes into mammalian, e.g., human cells.

To confirm the presence of the transgene in the host cell, a variety of assays may be performed. Such assays include, for example, "molecular biological" assays such as Southern and Northern blotting, RT-PCR and PCR; "biochemical" assays, such as detecting the presence or absence of a particular peptide, e.g., by immunological means (ELISAs and Western blots). To detect and quantitate RNA, RT-PCR may be employed. Further information about the RNA product may be obtained by Northern blotting. Expression may also be confirmed by specifically identifying the peptide encoded by the transgene or evaluating the phenotypic changes brought about by the expression of the transgene.

Such transduced or transfected cells are suitable for administration to a mammalian subject, for example, to provide cells that express the transgene. Thus, in one embodiment, cells are transfected ex vivo. The cells, prior to transfection or transduction, may be isolated from a mammal (such as a human), nucleic acid introduced (i.e., transduced or transfected in vitro) with a vector for expressing a heterologous nucleic acid encoding a therapeutic agent, and then administered to a mammalian subject for delivery of the therapeutic agent. The mammalian recipient may be a human and the cells to be modified are autologous cells, i.e., the cells are isolated from the mammalian subject to whom the cells will be administered.

In another embodiment, the cells are transfected or transduced in vivo. The cells from the mammalian subject are transduced or transfected in vivo with a vector containing a heterologous nucleic acid for expressing a therapeutic agent thereby delivering the therapeutic agent in situ.

Cells that may be transformed, in vitro or in vivo, include a cell of any tissue or organ type, of any origin (e.g., mesoderm, ectoderm or endoderm). Non-limiting examples of cells include central or peripheral nervous system, such as brain (e.g., neural, glial or ependymal cells) or spine, liver (e.g., hepatocytes, sinusoidal endothelial cells), pancreas (e.g., beta islet cells), lung, kidney, eye (e.g., retinal, cell components), spleen, skin, thymus, testes, lung, diaphragm, heart (cardiac), muscle or psoas, gut (e.g., endocrine), adipose tissue (white, brown or beige), muscle (e.g., fibroblasts), synoviocytes, chondrocytes, osteoclasts, epithelial cells, endothelial cells, salivary gland cells, inner ear nervous cells or hematopoietic (e.g., blood or lymph) cells. Additional examples include stem cells, such as pluripotent or multipotent progenitor cells that develop or differentiate into central or peripheral nervous system, such as brain (e.g., neural, glial or ependymal cells) or spine, liver (e.g., hepatocytes, sinusoidal endothelial cells), pancreas (e.g., beta islet cells), lung, kidney, eye (retinal, cell components), spleen, skin, thymus, testes, lung, diaphragm, heart (cardiac), muscle or psoas, or gut (e.g., endocrine), adipose tissue (white, brown or beige), muscle (e.g., fibroblasts), synoviocytes, chondrocytes, osteoclasts, epithelial cells, endothelial cells, salivary gland cells, inner ear nervous cells or hematopoietic (e.g., blood or lymph) cells.

A "therapeutic agent" in one embodiment is a peptide or protein that may alleviate or reduce symptoms that result from an absence or defect in a protein in a cell or subject. Alternatively, a "therapeutic agent" can be a peptide or protein encoded by a transgene that confers a benefit to a subject, e.g., to correct a genetic defect, or to correct a gene (expression or functional) deficiency. Accordingly, non-limiting examples of heterologous nucleic acids encode gene products (e.g., therapeutic agents/proteins) which are useful in accordance with the invention.

The invention provides methods of increasing the amount of a target protein in a subject by introducing a heterologous nucleic acid (e.g., by way of an rAAV) encoding the protein in an amount sufficient to increase the level of the target protein in the subject. In certain embodiments, the amount or accumulation of target protein is increased by 10% or more, e.g., 10%-20%, 20%-30%, 30%, 40%, 50%, 60%, 70%, 80%, 90% 95%, or 99%.

As set forth herein, heterologous nucleic acid sequences (transgenes) include inhibitory and antisense nucleic acid sequences. Inhibitory, antisense, siRNA, miRNA, shRNA, RNAi and antisense oligonucleotides can modulate, typically, reduce, inhibit, suppress or decrease expression of a target gene. Such molecules include those able to inhibit expression of a target gene involved in mediation of a disease process, thereby reducing, inhibiting or alleviating one or more symptoms of a disease.

The invention provides methods of reducing the amount of a target protein in a subject by introducing a heterologous nucleic acid (e.g., by way of an rAAV) that encodes or is transcribed into an inhibitory and antisense nucleic acid sequence in an amount sufficient to reduce, inhibit, suppress or decrease the level of the target protein in the subject. In certain embodiments, the amount or accumulation of target protein is reduced by 10% or more, e.g., 10%-20%, 20%-30%, 30%, 40%, 50%, 60%, 70%, 80%, 90% 95%, or 99%.

Antisense includes single, double or triple stranded nucleic acid sequences and peptide nucleic acids (PNAs) that bind RNA transcript or DNA (e.g., genomic DNA). Oligonucleotides derived from the transcription initiation site of a target gene, e.g., between positions −10 and +10 from the start site, are another particular example. Triplex forming antisense can bind to double strand DNA thereby inhibiting transcription of the gene.

"RNA interference," "RNAi," "small interfering RNA" or "short interfering RNA" or "siRNA" or "short hairpin RNA" or "shRNA" molecule, or "miRNA" is a use of single or double stranded RNA sequences for inhibiting gene expression (see, e.g., Kennerdell et al., Cell 95:1017 (1998); and Fire et al., Nature, 391:806 (1998)). During RNAi, siRNA induces degradation of target mRNA with consequent sequence-specific inhibition of gene expression.

An "RNA duplex" refers to the structure formed by the complementary pairing between two regions of a RNA molecule. Double stranded RNA sequences from a target gene coding region may therefore be used to inhibit or prevent gene expression/transcription in accordance with the methods and uses of the invention.

Antisense and RNAi can be produced based upon nucleic acids encoding target gene sequences (e.g., Ataxin-1, huntingtin, or HTT), such as nucleic acid encoding mammalian or human ataxin-1 or HTT. For example, a single or double stranded nucleic acid (e.g., RNA) can target ataxin-1 or HTT transcript (e.g., mRNA) to reduce, inhibit, suppress or decrease, expression.

The term "siRNA" is a generic term that encompasses the subset of shRNAs and miRNAs. Reference to siRNA is includes shRNAs and other small RNAs that can or are capable of modulating the expression of a targeted gene, via RNA interference. Such small RNAs include without limitation, shRNAs and miroRNAs (miRNAs).

siRNA is a nucleic acid involved in the RNA interference process for a sequence-specific post-transcriptional gene silencing or gene knockdown. siRNAs have homology with the sequence of the cognate mRNA of the targeted gene. siRNA is therefore "targeted" to a gene in that the nucleotide sequence of the duplex portion of the siRNA is complementary to a nucleotide sequence of the targeted gene. In certain embodiments, the siRNAs are targeted to the sequence encoding ataxin-1.

In some embodiments, the length of the duplex of siRNAs is less than 30 base pairs. In some embodiments, the duplex can be 29, 28, 27, 26, 25, 24, 23, 22, 21, 20, 19, 18, 17, 16, 15, 14, 13, 12, 11 or 10 base pairs in length. In some embodiments, the length of the duplex is 19 to 25 base pairs in length. In a certain embodiment, the length of the duplex is 19 or 21 base pairs in length.

The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24 or 25 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length.

The siRNA can be encoded by a heterologous nucleic acid sequence, and the heterologous nucleic acid sequence can also include a filler or stuffer sequence and additional element as set forth herein, such as an expression control element and/or a polyadenylation signal.

Small interfering RNAs (siRNAs) can also be synthesized in vitro or generated by ribonuclease III cleavage from longer dsRNA and are the mediators of sequence-specific mRNA degradation. siRNA or other such heterologous nucleic acids can be chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs for inhibiting mRNA of a target gene may be between 15-50 nucleotides in length, and more typically about 20-30 nucleotides in length. Such heterologous nucleic acids can be readily incorporated with a filler or stuffer sequence into the vectors (e.g., viral such as AAV) disclosed herein using conventional methods known to one of skill in the art.

The transcriptional unit of a "shRNA" is comprised of sense and antisense sequences connected by a loop of unpaired nucleotides. shRNAs are exported from the nucleus by Exportin-5, and once in the cytoplasm, are processed by Dicer to generate functional siRNAs.

A "miRNA" is a nucleic acid molecule involved in the RNA interference process. miRNAs are small cellular RNAs (~22nt) that are processed from precursor stem loop transcripts. Known miRNA stem loops can be modified to contain RNAi sequences specific for genes of interest. miRNAs are endogenously expressed. Therefore, miRNA molecules are unlikely to induce dsRNA-responsive interferon pathways, they are processed more efficiently than shRNAs, and they have been shown to silence more effectively than shRNAs.

The promoter roles are different for miRNA molecules compared to shRNA molecules. Tissue-specific, inducible expression of shRNAs involves truncation of polIII promoters to the transcription start site. In contrast, miRNAs can be expressed from any polII promoter because the transcription start and stop sites can be relatively arbitrary.

For production of miRNA in a cell or organism, a vector containing a U6 promoter operably linked to a nucleic acid encoding a miRNA can be used. In certain embodiments, the U6miRNA has an extended 5' end. If the 5' end is truncated to resemble the previous CMV-based strategy, silencing efficacy is severely reduced. The improved flanking sequences show improved efficacy over natural miR-30 flanking sequences. The miRNA strategy does not generally generate excessive amounts of RNAi as do U6shRNA approaches.

In particular embodiments, miRNA comprises or consists of: GGUCGAUCUUCAGGUCGUUGCUU-'3 (SEQ ID NO:3), or a subsequence thereof. In the DNA, replacing the Us with Ts, results in the sequence GGTCGATCTTCAGGTCGTTGCTT (SEQ ID NO:4).

In other embodiments, the RNAi molecule is one disclosed in U.S. Pat. Nos. 8,329,890; 8,779,116; 8,481,710; 8,524,879; 8,487,088; 8,258,286; 8,524,881; 8,299,215; 8,691,948; WO 2012/109667; and WO 2013/172964, which are incorporated by reference herein.

In certain embodiments, RNAi molecules are employed to inhibit expression of a target gene. By "inhibit expression" is meant to reduce, decrease, diminish or suppress expression of a target gene. Expression of a target gene may be inhibited via "gene silencing." Gene silencing refers to the suppression of gene expression, e.g., endogenous gene expression, which may be mediated through processes that affects transcription and/or that affects post-transcriptional mechanisms. In some embodiments, gene silencing occurs when an RNAi molecule initiates the inhibition or degradation of the mRNA transcribed from a gene of interest in a sequence-specific manner via RNA interference, thereby preventing translation of the gene's product.

Invention vectors can be used to provide silencing of targeted genes via RNAi. This strategy results in markedly diminished in vitro and in vivo expression of targeted genes in order to model biological processes or to provide therapy for human diseases.

The term "substantial silencing" means that the mRNA of the targeted gene is inhibited and/or degraded by the presence of the introduced siRNA, such that expression of the targeted gene is reduced by about 10% to 100% as compared to the level of expression seen when the RNAi is not present. Generally, when a gene is substantially silenced, it will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, 98%, 99% or even 100% reduction expression as compared to when the RNAi is not present.

"Expression" refers to the transcription and/or translation of a heterologous nucleic acid, polynucleotide, a transgene or an endogenous gene in cells. For example, in the case of an endogenous gene expression may refer to the expression of the target endogenous gene sought to be silenced. In the case of siRNA constructs, expression may refer to the transcription of the siRNA only. In addition, expression refers to the transcription and stable accumulation of sense (mRNA) or functional RNA. Expression may also refer to the production of a protein.

Particular non-limiting examples of genes (e.g., genomic DNA) or transcript of a pathogenic gene (e.g., RNA or mRNA) that may be targeted with inhibitory nucleic acid sequences in accordance with the invention include, but are not limited to: genes associated with polynucleotide repeat diseases such as huntingtin (HTT) gene, a gene associated with dentatorubropallidolusyan atropy (e.g., atrophin 1, ATN1); androgen receptor on the X chromosome in spinobulbar muscular atrophy, human Ataxin-1, -2, -3, and -7, $Ca_v2.1$ P/Q voltage-dependent calcium channel is encoded by the (CACNA1A), TATA-binding protein, Ataxin 8 opposite strand, also known as ATXN8OS, Serine/threonine-protein phosphatase 2A 55 kDa regulatory subunit B beta isoform in spinocerebellar ataxia (types 1, 2, 3, 6, 7, 8, and 17), FMR1 (fragile X mental retardation 1) in fragile X syndrome, FMR1 (fragile X mental retardation 1) in fragile X-associated tremor/ataxia syndrome, FMR1 (fragile X mental retardation 2) or AF4/FMR2 family member 2 in fragile XE mental retardation; Myotonin-protein kinase (MT-PK) in myotonic dystrophy; Frataxin in Friedreich's ataxia; a mutant of superoxide dismutase 1 (SOD1) gene in amyotrophic lateral sclerosis; a gene involved in pathogenesis of Parkinson's disease and/or Alzheimer's disease; apolipoprotein B (APOB) and proprotein convertase subtilisin/kexin type 9 (PCSK9).

Methods and uses of the invention provide a means for delivering (transducing) nucleic acid sequences as set forth herein, such as stuffer or filler sequences alone, and in combination with heterologous nucleic acid sequences (transgenes) into a broad range of host cells, including both dividing and non-dividing cells. The recombinant vector (e.g., AAV), vector genomes, methods, uses and pharmaceutical formulations of the invention are additionally useful in a method of administering or delivering a nucleic acid encoding an inhibitory nucleic acid, or a nucleic acid encoding a protein, peptide or to a subject in need thereof, as a method of treatment. In this manner, the inhibitory nucleic acid, or the protein, or peptide may thus be produced in vivo in a subject. The subject may benefit from or be in need of the treatment because the subject has expression or production of a target gene or sequence involved in a disease process, e.g., for the treatment of a neurodegenerative disease, for example to achieve a therapeutic effect, or because the subject has a deficiency of the protein, peptide or nucleic acid, or because production of the protein, peptide or nucleic acid in the subject may impart some therapeutic effect, as a method of treatment or otherwise.

Accordingly, invention compositions (e.g., stuffer or filler sequences alone, and in combination with heterologous nucleic acid sequences), methods and uses permit the treatment of genetic diseases.

In general, invention recombinant vector (e.g., AAV), vector genomes, methods and uses may be used to deliver any heterologous nucleic acid (transgene) with a biological effect to treat or ameliorate one or more symptoms associated with any disorder related to insufficient or undesirable gene expression. Invention recombinant vector (e.g., AAV) vector genomes, methods and uses may be used to provide therapy for various disease states.

There are a number of inherited diseases in which defective genes are known and have been cloned. In general, the above disease states fall into two classes: deficiency states, usually of enzymes, which are generally inherited in a recessive manner, and unbalanced states, at least sometimes involving regulatory or structural proteins, which are inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus, invention recombinant vector (e.g., AAV), vector genomes, methods and uses permit the treatment of genetic diseases. As used herein, a disease state is treated by partially or wholly remedying the deficiency or imbalance that causes the disease or makes it more severe. The use of site-specific integration of nucleic acid sequences to cause mutations or to correct defects is also possible.

In accordance with the invention, in vivo administration and treatment methods and uses are provided that include invention recombinant vector (e.g., AAV), vector genomes, and recombinant virus particles including vector genomes. Methods and uses of the invention are broadly applicable to diseases amenable to treatment by introducing a gene encoding a protein, or increasing or stimulating gene expression or function, e.g., gene addition or replacement. Methods and uses of the invention are also broadly applicable to diseases amenable to treatment by reducing or decreasing gene expression or function, e.g., gene silencing, knockout or reduction of gene expression (gene knockdown).

Invention methods also include delivering a nucleic acid to the brain by administering a vector with a heterologous nucleic acid inserted between a pair of AAV inverted terminal repeats. Such target cells include medium spiny neurons.

Also provided are methods of delivering a nucleic acid to a brain cell. Such target cells include neurons in the striatum or cortex in a subject. In one embodiment, a method includes administering to the subject an AAV particle comprising heterologous nucleic acid inserted between a pair of AAV inverted terminal repeats, thereby delivering the nucleic acid to the neuron or other brain cell in the subject.

According to a method of the invention, expression of mRNA encoding SCA1 can be modified via RNAi. For example, the production or accumulation of mRNA encoding SCA1 can be suppressed in a cell. The term "suppressing" refers to the diminution, reduction or elimination in the number or amount of mRNA molecules present in a particular cell. For example, the accumulation of mRNA can be suppressed in a cell by RNA interference (RNAi), e.g., the gene is silenced (i.e., expression is reduced as set forth herein) by sequence-specific double-stranded RNA (dsRNA), which is also called short interfering RNA (siRNA). These siRNAs can be two separate RNA molecules that have hybridized together, or they may be a single hairpin wherein two portions of a RNA molecule have hybridized together to form a duplex.

"Treating" as used herein refers to ameliorating at least one symptom of, curing and/or preventing the development of a disease or a condition, such as after development of a pathology or symptom of a CNS disease. The term "ameliorate" means a detectable or measurable improvement in a subject's disease, pathology or symptom thereof, or an underlying cellular response. A detectable or measurable improvement includes a subjective or objective decrease, reduction, inhibition, suppression, limit or control in the occurrence, frequency, severity, progression, or duration of the disease, pathology or complication caused by or associated with the disease, or an improvement in a symptom or an underlying cause or a consequence of the disease (pathology), or a reversal of the disease. Treating can include stabilizing the disease, pathology or symptom thereof, or preventing progression, worsening or halting a disease, pathology or symptom, as well as reversing severity of a disease, pathology or symptom or providing an improvement in the disease, pathology or symptom.

SCA1 is a strong candidate for siRNA-based therapy. SCA1 is progressive, ultimately fatal disorders that typically begin in adulthood. As a therapeutic strategy, efforts to lower expression of the mutant gene product prior to cell death should be highly beneficial to patients. The invention provides compositions, methods and uses of treating SCA1. In one embodiment, a method includes administration of a mammal with a therapeutic acid agent, e.g., a nucleic acid sequence encoded by or transcribed from an expression vector, or a vector particle (e.g. rAAV) that binds to SCA1 mRNA.

Methods of delivery of viral vectors include injecting the AAV into the subject. Generally, rAAV virions may be introduced into cells of the CNS using either in vivo or in vitro transduction techniques. Suitable methods for the delivery and introduction of transduced cells into a subject are disclosed herein and known to the skilled artisan.

Suitable subjects include mammals, such as humans, as well as non-human mammals. The term "subject" refers to an animal, typically a mammal, such as humans, non-human primates (apes, gibbons, gorillas, chimpanzees, orangutans, macaques), a domestic animal (dogs and cats), a farm animal (poultry such as chickens and ducks, horses, cows, goats, sheep, pigs), and experimental animals (mouse, rat, rabbit, guinea pig). Human subjects include fetal, neonatal, infant, juvenile and adult subjects. Subjects include animal disease models, such as dog and non-human primate models of CNS diseases.

To produce rAAV virions, an AAV expression vector is introduced into a suitable host cell using known techniques, such as by transfection. A number of transfection techniques are can be used. See, e.g., Sambrook et al. (1989) Molecular Cloning, a laboratory manual, Cold Spring Harbor Laboratories, New York. Suitable transfection methods include calcium phosphate co-precipitation, direct micro-injection into cultured cells, electroporation, liposome mediated gene transfer, lipid-mediated transduction, and nucleic acid delivery using high-velocity microprojectiles.

Suitable host cells for producing rAAV virions include microorganisms, yeast cells, insect cells, and mammalian cells, that can be, or have been, used as recipients of a heterologous nucleic acid. Host cells includes progeny of the original cell which was transfected. Particular examples of suitable cells are stable human cell lines, such as 293 (American Type Culture Collection under Accession Number ATCC CRL1573). The human cell line 293 is a human embryonic kidney cell line that has been transformed with adenovirus type-5 DNA fragments, and expresses the adenoviral E1a and E1b genes. The 293 cell line is readily transfected, and provides a convenient platform in which to produce rAAV virions.

An "AAV rep coding region" is the region of the AAV genome which encodes the replication proteins Rep 78, Rep 68, Rep 52 and Rep 40. These Rep proteins have been shown to possess many functions, including recognition, binding and nicking of the AAV origin of DNA replication, DNA helicase activity and modulation of transcription from AAV (or other heterologous) promoters. The Rep proteins are collectively required for replicating the AAV genome. Homologs of the AAV rep coding region include human herpesvirus 6 (HHV-6) rep gene.

The "AAV cap coding region" is the region of the AAV genome which encodes the capsid proteins VP1, VP2, and VP3. These capsid proteins supply the packaging functions that are collectively required for packaging the viral genome.

AAV helper functions can be introduced into the host cell by transfecting the host cell with an AAV helper construct either prior to, or concurrently with, transfection of the AAV vector. AAV helper constructs thus provide at least transient expression of AAV rep and/or cap genes to complement missing AAV functions that are necessary for productive AAV infection. AAV helper constructs lack AAV ITRs and can neither replicate nor package themselves. A number of AAV helper constructs have been described, such as plasmids pAAV/Ad and pIM29+45 which encode both Rep and Cap expression products. A number of other vectors have been described which encode Rep and/or Cap expression products.

The vectors can be included in pharmaceutical compositions. Such compositions can optionally include sufficient vector to produce an effective amount of the heterologous nucleic acid, i.e., an amount sufficient to reduce or ameliorate symptoms of a disease state in question or an amount sufficient to confer the desired benefit.

Pharmaceutical compositions include solvents (aqueous such as saline, water, artificial CSF, or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Supplementary active compounds (e.g., surfactants, preservatives, antibacterial, antiviral and antifungal agents) can also be incorporated into the compositions.

The pharmaceutical compositions typically will contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles.

To prepare a formulation, the purified composition can be manufactured, prepared and/or isolated. The composition may then be adjusted to an appropriate concentration.

Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

Pharmaceutical compositions can be administered by a variety of routes including parenteral, including by intravenous and intramuscular routes, as well as by direct injection into the diseased tissue. For example, therapeutic agent (e.g., rAAV) may be directly injected into the brain. Alternatively the therapeutic agent (e.g., rAAV) may be introduced intrathecally for brain and spinal cord conditions. In another example, the therapeutic agent (e.g., rAAV) may be introduced intramuscularly for vectors that traffic to affected neurons from muscle, such as AAV, lentivirus and adenovirus.

Compositions suitable for parenteral administration comprise aqueous and non-aqueous solutions, suspensions or emulsions of the active compound, which preparations are typically sterile and can be isotonic with the blood of the intended recipient. Non-limiting illustrative examples include water, buffered saline, Hanks' solution, Ringer's solution, dextrose, fructose, ethanol, animal, vegetable or synthetic oils. Aqueous injection suspensions may contain substances which increase the viscosity of the suspension, such as sodium carboxymethyl cellulose, sorbitol, or dextran.

Co-solvents and adjuvants may be added to the formulation. Non-limiting examples of co-solvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

After pharmaceutical compositions have been prepared, they may be placed in an appropriate container and labeled for treatment. For administration of vectors (e.g., rAAV) as set forth herein, such labeling can include amount, frequency, and method of administration.

Pharmaceutical compositions and delivery systems appropriate for the compositions, methods and uses of the invention are known in the art (see, e.g., *Remington: The Science and Practice of Pharmacy* (2003) 20th ed., Mack Publishing Co., Easton, Pa.; *Remington's Pharmaceutical Sciences* (1990) 18th ed., Mack Publishing Co., Easton, Pa.; *The Merck Index* (1996) 12th ed., Merck Publishing Group, Whitehouse, N.J.; *Pharmaceutical Principles of Solid Dosage Forms* (1993), Technonic Publishing Co., Inc., Lancaster, Pa.; Ansel and Stoklosa, *Pharmaceutical Calculations* (2001) 11th ed., Lippincott Williams & Wilkins, Baltimore, Md.; and Poznansky et al., *Drug Delivery Systems* (1980), R. L. Juliano, ed., Oxford, N.Y., pp. 253-315).

The vectors of the invention can be administered to provide a reduction in at least one symptom associated with a disease. Accordingly, pharmaceutical compositions of the invention include compositions in which a therapeutic agent (e.g., rAAV) is in an amount effective to achieve the intended therapeutic purpose. An "effective amount" or "sufficient amount" refers to an amount that provides, in single or multiple doses, alone or in combination, with one or more other compositions (therapeutic agents such as a drug), treatments, protocols, or therapeutic regimens agents, a detectable response of any duration of time (long or short term), an expected or desired outcome in or a benefit to a subject of any measurable or detectable degree or for any duration of time (e.g., for minutes, hours, days, months, years, or cured). The doses of an "effective amount" or "sufficient amount" for treatment (e.g., to ameliorate or to provide a therapeutic benefit or improvement) typically are effective to provide a response to one, multiple or all adverse symptoms, consequences or complications of the disease, one or more adverse symptoms, disorders, illnesses, pathologies, or complications, for example, caused by or associated with the disease, to a measurable extent, although decreasing, reducing, inhibiting, suppressing, limiting or controlling progression or worsening of the disease is a satisfactory outcome.

For a CNS disease, an effective amount would be an amount that improves motor or cognitive function, or reduces, decreases, suppresses or inhibits motor or cognitive impairment or further impairment, deterioration or worsening in motor or cognitive function. In certain embodiments, an effective amount would be an amount that improves wide-based gait, difficulties with balance, speech, swallowing, coordination and/or spasticity; reduces, decreases, suppresses or inhibits wide-based gait, difficulties with balance, speech, swallowing, coordination and/or spasticity; or further impairment, deterioration or worsening of wide-based gait, difficulties with balance, speech, swallowing, coordination and/or spasticity. In certain embodiments, an effective amount would be an amount that improves extracerebellar function, for example, reduces, decreases, suppresses or inhibits deep tendon reflexes and oculomotor abnormalities; or reduces, decreases, suppresses or inhibits further impairment, deterioration or worsening of extracerebellar function, for example, deep tendon reflexes and oculomotor abnormalities.

CNS disease status, progression, etc. can be reflected by the foregoing criteria as well as cerebellar pathology, such as thinning in cerebellas lobules, and cell morphology such as Purkinje cell dendrite retraction. CNS disease status, progression, etc. also can be reflected by prevalence/distribution of mutant Ataxin-1 and prevalence/distribution other molecular biomarkers, etc., as set forth herein. A reduction, decrease, inhibition or suppression, stabilization or preventing worsening, or normalization or a reversal of any of the foregoing, and the other criteria set forth herein for treating and improvement, as well as the specific criteria set forth in the examples herein, can be indicative of an effective amount (e.g., dose).

Formulations containing vector (e.g., rAAV) particles will contain an effective amount of the rAAV, the effective amount determined by one skilled in the art. The rAAV particles may typically range from about 1% to about 95% (w/w) of the composition, or even higher or lower if appropriate.

An effective amount or a sufficient amount (e.g., dose). can but need not be provided in a single administration, may require multiple administrations, and, can but need not be, administered alone or in combination with another composition (e.g., agent), treatment, protocol or therapeutic regimen. For example, the amount may be proportionally increased as indicated by the need of the subject, type, status and severity of the disease treated or side effects (if any) of treatment. In addition, an effective amount or a sufficient amount need not be effective or sufficient if given in single or multiple doses without a second composition (e.g., another drug or agent), treatment, protocol or therapeutic regimen, since additional doses, amounts or duration above and beyond such doses, or additional compositions (e.g., drugs or agents), treatments, protocols or therapeutic regimens may be included in order to be considered effective or sufficient in a given subject. Amounts considered effective also include amounts that result in a reduction of the use of another treatment, therapeutic regimen or protocol.

Accordingly, methods and uses include, among other things, methods and uses that result in a reduced need or use of another compound, agent, drug, therapeutic regimen, treatment protocol, process, or remedy. Thus, in accordance with the invention, methods and uses of reducing need or use of another treatment or therapy are provided.

An effective amount or a sufficient amount need not be effective in each and every subject treated, nor a majority of treated subjects in a given group or population. As is typical for such methods, some subjects will exhibit a greater response, or less or no response to a given treatment method or use.

The amount administered will vary depending on various factors. Doses can vary and depend upon the type of disease, onset, progression, severity, frequency, duration, or probability of the disease to which treatment is directed, the clinical endpoint desired, previous or simultaneous treatments, the general health, physical condition, age, gender, race or immunological competency of the subject and other factors that will be appreciated by the skilled artisan. The dose amount, number, frequency or duration may be proportionally increased or reduced, as indicated by any adverse side effects, complications or other risk factors of the treatment or therapy and the status of the subject. The factors that may influence the dosage and timing required to provide an amount effective or sufficient for providing a therapeutic or prophylactic benefit can be readily determined by the skilled artisan.

The dose to achieve a therapeutic effect, e.g., the dose in vector genomes/per kilogram of body weight (vg/kg), will vary based on several factors including, but not limited to: route of administration, the level of heterologous nucleic acid sequence expression required to achieve a therapeutic effect, the specific disease treated, any host immune response to the viral vector, a host immune response to the heterologous nucleic acid sequence or expression product (protein), and the stability of the protein expressed. One skilled in the art can determine rAAV/vector genome dose range to treat a patient having a particular disease or disorder based on the aforementioned factors, as well as other factors.

Methods of determining the most effective means and doses of administration are known to those of skill in the art and will vary with the viral vector, the composition of the therapy, the target cells, and the subject being treated. For example, an effective amount of vector to be administered can be based upon non-human primate or other mammalian studies, or empirically determined.

Single and multiple administrations can be carried out with the dose level and pattern being selected by the treating physician. Both local and systemic administration is contemplated. Administration may be continuous or intermittent. Administration can be effected in one dose, continuously or intermittently throughout the course of treatment.

Administration or in vivo delivery to a subject can be performed prior to or after development of an adverse symptom, condition, complication, etc. caused by or associated with the disease, such as a pathology or symptom of a CNS disease. For example, a screen (e.g., genetic) can be used to identify such subjects as candidates for invention compositions, methods and uses. A screen such as mere observation can also be used to identify subjects having an adverse symptom, condition, complication, etc. caused by or associated with the disease, such as a pathology or symptom of a CNS disease, as subjects appropriate for invention compositions, methods and uses. Such subjects therefore include those screened positive for an insufficient amount or a deficiency in a functional gene product or production of a harmful, deleterious, aberrant, partially functional or non-functional gene product.

Administration or in vivo delivery to a subject in accordance with the methods and uses of the invention as disclosed herein can be practiced within 1-2, 2-4, 4-12, 12-24 or 24-72 hours after a subject has been identified as having the disease targeted for treatment, has one or more symptoms of the disease, or has been screened and is identified as positive as set forth herein even though the subject does not have one or more symptoms of the disease. Of course, methods and uses of the invention can be practiced 1-7, 7-14, 14-21, 21-48 or more days, months or years after a subject has been identified as having the disease targeted for treatment, has one or more symptoms of the disease, or has been screened and is identified as positive as set forth herein.

In certain embodiments, rAAV is administered at a dose of about 0.3-2 ml of $1\times10^5$-$1\times10^{16}$ vg/ml. In certain embodiments, the rAAV is administered at a dose of about 1-3 ml of $1\times10^7$-$1\times10^{14}$ vg/ml. In certain embodiments, the rAAV is administered at a dose of about 1-2 ml of $1\times10^8$-$1\times10^{13}$ vg/ml.

With respect to a deficiency state in a subject, a typical dose of rAAV is at least $1\times10^9$ vector genomes (vg) per kilogram (vg/kg) of the weight of the subject, $1\times10^{10}$ vector genomes (vg) per kilogram (vg/kg) of the weight of the subject, or between about $1\times10^{10}$ to $1\times10^{11}$ vg/kg of the weight of the subject, or between about $1\times10^{11}$ to $1\times10^{12}$ vg/kg of the weight of the subject, or between about $1\times10^{12}$ to $1\times10^{13}$ vg/kg of the weight of the subject.

The compositions may be conveniently prepared or provided in discrete unit dosage forms and may be prepared by any of methods well known to pharmacy. Such methods may include the step of bringing into association the vector (therapeutic agent) with liquid carriers, solid matrices, semi-solid carriers, finely divided solid carriers or combinations thereof, and then, if necessary, introducing or shaping the product into the desired delivery system.

A "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dosage forms may be within, for example, ampules and vials, which may include a liquid composition, or a composition in a freeze-dried or lyophilized state; a sterile liquid carrier, for example, can be added prior to administration or delivery in vivo. Individual unit dosage forms can be included in multi-dose kits or containers. Recombinant vector (e.g., rAAV), recombinant virus particles, and pharmaceutical compositions thereof can be packaged in single or multiple unit dosage form for ease of administration and uniformity of dosage.

The invention provides kits with packaging material and one or more components therein. A kit typically includes a label or packaging insert including a description of the components or instructions for use in vitro, in vivo, or ex vivo, of the components therein. A kit can contain a collection of such components, e.g., a filler or stuffer alone, or in combination or be a component of, a heterologous nucleic acid sequence, recombinant vector, virus (e.g., AAV) vector, and optionally in combination with a second active, such as another compound, agent, drug or composition.

A kit refers to a physical structure housing one or more components of the kit. Packaging material can maintain the components sterilely, and can be made of material commonly used for such purposes (e.g., paper, corrugated fiber, glass, plastic, foil, ampules, vials, tubes, etc.).

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer, lot numbers, manufacture location and date, expiration dates. Labels or inserts can include information identifying manufacturer information, lot numbers, manufacturer location and date. Labels or inserts can include information on a disease for which a kit component may be used. Labels or inserts can include instructions for the clinician or subject for using one or more of the kit components in a method, use, or treatment protocol or therapeutic regimen. Instructions can include dosage amounts, frequency or duration, and instructions for practicing any of the methods, uses, treatment protocols or prophylactic or therapeutic regimes described herein.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a bar-coded printed label, a disk, optical disk such as CD- or DVD-ROM/RAM, DVD, MP3, magnetic tape, or an electrical storage media such as RAM and ROM or hybrids of these such as magnetic/optical storage media, FLASH media or memory type cards.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All patents, patent applications, publications, and other references, GenBank citations and ATCC citations cited herein are incorporated by reference in their entirety. In case of conflict, the specification, including definitions, will control.

Various terms relating to the biological molecules of the invention are used hereinabove and also throughout the specification and claims.

All of the features disclosed herein may be combined in any combination. Each feature disclosed in the specification may be replaced by an alternative feature serving a same, equivalent, or similar purpose. Thus, unless expressly stated otherwise, disclosed features (e.g., filler or stuffer sequence, heterologous nucleic acid sequence, vector, plasmid, recombinant vector (e.g., rAAV), or recombinant virus particle) are an example of a genus of equivalent or similar features.

As used herein, the singular forms "a", "and," and "the" include plural referents unless the context clearly indicates otherwise. Thus, for example, reference to "filler or stuffer sequence" includes a plurality of such filler or stuffer sequences. Reference to "a nucleic acid" includes a plurality of such nucleic acids, reference to "a vector" includes a plurality of such vectors, and reference to "a virus" or "particle" includes a plurality of such viruses/particles, etc.

As used herein, all numerical values or numerical ranges include integers within such ranges and fractions of the values or the integers within ranges unless the context clearly indicates otherwise. Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to at least 70% or more includes 70, 71, 72, etc. all the way up to the number 100.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-850, includes ranges of 1-20, 1-30, 1-40, 1-50, 1-60, 10-30, 10-40, 10-50, 10-60, 10-70, 10-80, 20-40, 20-50, 20-60, 20-70, 20-80, 20-90, 50-75, 50-100, 50-150, 50-200, 50-250, 100-200, 100-250, 100-300, 100-350, 100-400, 100-500, 150-250, 150-300, 150-350, 150-400, 150-450, 150-500, etc.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions. Accordingly, the following examples are intended to illustrate but not limit the scope of the invention claimed in any way.

Example 1

A highly modified filler or stuffer sequence has been developed for optimizing packaging of short transgenes/therapeutic agents in AAV. Examples of short transgenes that are therapeutic agents include RNA guides for use in CrispR/Cas editing approaches, or RNAi expression cassettes. The latter could be artificial miRNAs or shRNAs.

In particular features, the filler or stuffer sequence had reduced or minimized CpG motifs so the DNA elements retained in transduced cells for sustained expression of a short transgene in vivo leads to a reduced or decreased immune response, or optimally does not stimulate, promote or induce an immune response. The filler or stuffer sequence also had been modified to reduce the frequency of ATG codons, to reduce or eliminate the possibility of peptides being generated from the filler or stuffer sequence. Finally, the filler or stuffer has been carefully modified to contain no known enhancer sequences, repressor sequences, splicing doors or acceptors, or other known active elements found in the human genome that could potentially affect transcription of the transgene. Hence, the term "safe" filler or stuffer sequence.

A representative plasmid sequence having a representative highly modified filler or stuffer sequence is depicted below, denoted "pKFBextmU6miS1newStfr". The various elements comprising the representative plasmid sequence are indicated in the legend below, and the corresponding positions within the plasmid sequence are denoted according to nucleotide residues to the right of the elements.

The highly modified filler or stuffer sequence starts at position 4513 and ends at position 8286, and is SEQ ID NO:1. The vector sequence that is packaged, in an AAV vector, starts at position 3858 and ends at position 8456, and is denoted SEQ ID NO:2.

Representative therapeutic agent miS1 has the sequence 5'-GGUCGAUCUUCAGGUCGUUGCUU-'3 (SEQ ID NO:3). In the map below, replacing the Us with Ts, results in the sequence GGTCGATCTTCAGGTCGTTGCTT (SEQ ID NO:4). The miS1 sequence starts at position 4432 in the map below, and is underlined. The larger hairpin structure comprising miS1 starts at position 4380 and ends at position 4465 and is denoted SEQ ID NO:5 The 5' and 3' flanking ITRs are denoted SEQ ID NOs:6 and 7, respectively.

| | |
|---|---|
| pKFBextmU6miS1newStfr | 11591 bp DNA circular |
| T7n Right | 2466..2690 |
| Gentamicin Resistance | complement 2757..3290 |
| ITR 119 bp (SEQ ID NO: 6) | 3858..3976 |
| ITR 130 bp (SEQ ID NO: 7) | 8327..8456 |
| Z zuvgt phage genes | 8632..9617 |
| H phage gene H | 9618..11058 |
| SV40snip | 11081..11215 |
| Tn7 Left | 11244..11398 |
| KanR (9333-10145) | complement(587..1399) |
| New stuffer sequence (SEQ ID NO: 1) | 4513..8286 |
| SnaBI | 8287..8292 |
| RNAi expression cassette | 4030..4512 |
| mouse U6 promoter | 4036..4346 |
| 5-end Pri-miRNA | 4346..4379 |
| 3-end Pri-miRNA | 4466..4512 |
| miS1 (SEQ ID NO: 4) in (SEQ ID NO: 5) | 4380..4465 |
| pKFBextmU6miS1newStfr (SEQ ID NO: 8) | 1..11591 |

```
   1  GACGCGCCCT GTAGCGGCGC ATTAAGCGCG GCGGGTGTGG TGGTTACGCG CAGCGTGACC
  61  GCTACACTTG CCAGCGCCCT AGCGCCCGCT CCTTTCGCTT TCTTCCCTTC CTTTCTCGCC
 121  ACGTTCGCCG GCTTTCCCCG TCAAGCTCTA AATCGGGGGC TCCCTTTAGG GTTCCGATTT
 181  AGTGCTTTAC GGCACCTCGA CCCCAAAAAA CTTGATTAGG GTGATGGTTC ACGTAGTGGG
 241  CCATCGCCCT GATAGACGGT TTTTCGCCCT TGACGTTGG AGTCCACGTT CTTAATAGTG
 301  GACTCTTGTT CCAAACTGGA ACAACACTCA ACCCTATCTC GGTCTATTCT TTTGATTTAT
 361  AAGGGATTTT GCCGATTTCG GCCTATTGGT TAAAAAATGA GCTGATTTAA CAAAAATTTA
 421  ACGCGAATTT TAACAAAATA TTAACGCTTA CAATTTAGGT GGCACTTTTC GGGGAAATGT
 481  GCGCGGAACC CCTATTTGTT TATTTTTCTA AATACATTCA AATATGTATC CGCTCATGAG
 541  ACAATAACCC TGATAAATGC TTCAATAATA TTGAAAAAGG AAGAGTatga gccatattca
 601  acgggaaacg tcttgctcga agccgcgatt aaattccaac atggatgctg atttatatgg
 661  gtataaatgg ctcgcgata atgtcgggca atcaggtgcg acaatctatc gattgtatgg
 721  gaagcccgat gcgccagagt tgtttctgaa acatggcaaa ggtagcgttg ccaatgatgt
 781  tacagatgag atggtcagac taaactggct gacggaattt atgcctcttc cgaccatcaa
 841  gcattttatc cgtactcctg atgatgcatg gttactcacc actgcgatcc ccgggaaaac
 901  agcattccag gtattagaag aatatcctga ttcaggtgaa atattgttga atgcgctggc
 961  agtgttcctg cgccggttgc attcgattcc tgtttgtaat gtccttttta acagcgatcg
1021  cgtatttcgt ctcgctcagg cgcaatcacg aatgaataac ggtttggttg atgcgagtga
1081  ttttgatgac gagcgtaatg gctggcctgt tgaacaagtc tggaaagaaa tgcataagct
1141  tttgccattc tcaccggatt cagtcgtcac tcatggtgat ttctcacttg ataaccttat
1201  ttttgacgag gggaaattaa taggttgtat tgatgttgga cgagtcggaa tcgcagaccg
1261  ataccaggat cttgccatcc tatggaactg cctcggtgag ttttctcctt cattacagaa
1321  acggcttttt caaaaatatg gtattgataa tcctgatatg aataaattgc agtttcattt
1381  gatgctcgat gagttttttct aaCTGTCAGA CCAAGTTTAC TCATATATAC TTTAGATTGA
1441  TTTAAAACTT CATTTTTAAT TTAAAAGGAT CTAGGTGAAG ATCCTTTTTG ATAATCTCAT
1501  GACCAAAATC CCTTAACGTG AGTTTTCGTT CCACTGAGCG TCAGACCCCG TAGAAAAGAT
1561  CAAAGGATCT TCTTGAGATC CTTTTTTTCT GCGCGTAATC TGCTGCTTGC AAACAAAAAA
1621  ACCACCGCTA CCAGCGGTGG TTTGTTTGCC GGATCAAGAG CTACCAACTC TTTTTCCGAA
1681  GGTAACTGGC TTCAGCAGAG CGCAGATACC AAATACTGTT CTTCTAGTGT AGCCGTAGTT
1741  AGGCCACCAC TTCAAGAACT CTGTAGCACC GCCTACATAC CTCGCTCTGC TAATCCTGTT
1801  ACCAGTGGCT GCTGCCAGTG GCGATAAGTC GTGTCTTACC GGGTTGGACT CAAGACGATA
1861  GTTACCGGAT AAGGCGCAGC GGTCGGGCTG AACGGGGGGT TCGTGCACAC AGCCCAGCTT
1921  GGAGCGAACG ACCTACACCG AACTGAGATA CCTACAGCGT GAGCTATGAG AAAGCGCCAC
1981  GCTTCCCGAA GGGAGAAAGG CGGACAGGTA TCCGGTAAGC GGCAGGGTCG AACAGGAGA
2041  GCGCACGAGG GAGCTTCCAG GGGGAAACGC CTGGTATCTT TATAGTCCTG TCGGGTTTCG
2101  CCACCTCTGA CTTGAGCGTC GATTTTTGTG ATGCTCGTCA GGGGGGCGGA GCCTATGGAA
2161  AAACGCCAGC AACGCGGCCT TTTTACGGTT CCTGGCCTTT TGCTGGCCTT TTGCTCACAT
2221  GTTCTTTCCT GCGTTATCCC CTGATTCTGT GGATAACCGT ATTACCGCCT TTGAGTGAGC
2281  TGATACCGCT CGCCGCAGCC GAACGACCGA GCGCAGCGAG TCAGTGAGCG AGGAAGCGGA
```

-continued

```
2341 AGAGCGCCTG ATGCGGTATT TTCTCCTTAC GCATCTGTGC GGTATTTCAC ACCGCATAGA
2401 CCAGCCGCGT AACCTGGCAA AATCGGTTAC GGTTGAGTAA TAAATGGATG CCCTGCGTAA
2461 GCGGGTGTGG GCGGACAATA AAGTCTTAAA CTGAACAAAA TAGATCTAAA CTATGACAAT
2521 AAAGTCTTAA ACTAGACAGA ATAGTTGTAA ACTGAAATCA GTCCAGTTAT GCTGTGAAAA
2581 AGCATACTGG ACTTTTGTTA TGGCTAAAGC AAACTCTTCA TTTTCTGAAG TGCAAATTGC
2641 CCGTCGTATT AAAGAGGGGC GTGGCCAAGG GCATGGTAAA GACTATATTC GCGGCGTTGT
2701 GACAATTTAC CGAACAACTC CGCGGCCGGG AAGCCGATCT CGGCTTGAAC GAATTGTTAG
2761 GTGGCGGTAC TTGGGTCGAT ATCAAAGTGC ATCACTTCTT CCCGTATGCC AACTTTGTA
2821 TAGAGAGCCA CTGCGGGATC GTCACCGTAA TCTGCTTGCA CGTAGATCAC ATAAGCACCA
2881 AGCGCGTTGG CCTCATGCTT GAGGAGATTG ATGAGCGCGG TGGCAATGCC CTGCCTCCGG
2941 TGCTCGCCGG AGACTGCGAG ATCATAGATA TAGATCTCAC TACGCGGCTG CTCAAACTTG
3001 GGCAGAACGT AAGCCGCGAG AGCGCCAACA ACCGCTTCTT GGTCGAAGGC AGCAAGCGCG
3061 ATGAATGTCT TACTACGGAG CAAGTTCCCG AGGTAATCGG AGTCCGGCTG ATGTTGGGAG
3121 TAGGTGGCTA CGTCTCCGAA CTCACGACCG AAAAGATCAA GAGCAGCCCG CATGGATTTG
3181 ACTTGGTCAG GGCCGAGCCT ACATGTGCGA ATGATGCCCA TACTTGAGCC ACCTAACTTT
3241 GTTTTAGGGC GACTGCCCTG CTGCGTAACA TCGTTGCTGC TGCGTAACAT CGTTGCTGCT
3301 CCATAACATC AAACATCGAC CCACGGCGTA ACGCGCTTGC TGCTTGGATG CCCGAGGCAT
3361 AGACTGTACA AAAAAACAGT CATAACAAGC CATGAAAACC GCCACTGCGC CGTTACCACC
3421 GCTGCGTTCG GTCAAGGTTC TGGACCAGTT GCGTGAGCGC ATACGCTACT GCATTACAG
3481 TTTACGAACC GAACAGGCTT ATGTCAACTG GGTTCGTGCC TTCATCCGTT CCACGGTGT
3541 GCGTCACCCG GCAACCTTGG GCAGCAGCGA AGTCGAGGCA TTTCTGTCCT GGCTGGCGAA
3601 CGAGCGCAAG GTTTCGGTCT CCACGCATCG TCAGGCATTG GCGGCCTTGC TGTTCTTCTA
3661 CGGCAAGGTG CTGTGCACGG ATCTGCCCTG GCTTCAGGAG ATCGGAAGAC CTCGGCCGTC
3721 GCGGCGCTTG CCGGTGGTGC TGACCCCGGA TGAAGTGGTT CGCATCCTCG GTTTTCTGGA
3781 AGGCGAGCAT CGTTTGTTCG CCCAGGACTC TAGCTATAGT TCTAGTGGTT GGCTACAGCT
3841 TGCATGCCTG CAGGCAGCTG CGCGCTCGCT CGCTCACTGA GGCCGCCCGG GCGTCGGGCG
3901 ACCTTTGGTC GCCCGGCCTC AGTGAGCGAG CGAGCGCGCA GAGAGGGAGT GGCCAACTCC
3961 ATCACTAGGG GTTCCTTGTA GTTAATGATT AACCCGCCAT GCTACTTATC TACGTAGCCA
4021 TGCTCTAGTG AATTCGACGC CGCCATCTCT AGGCCCGCGC CGGCCCCCTC GCACAGACTT
4081 GTGGGAGAAG CTCGGCTACT CCCCTGCCCC GGTTAATTTG CATATAATAT TTCCTAGTAA
4141 CTATAGAGGC TTAATGTGCG ATAAAAGACA GATAATCTGT TCTTTTTAAT ACTAGCTACA
4201 TTTTACATGA TAGGCTTGGA TTTCTATAAG AGATACAAAT ACTAAATTAT TATTTAAAA
4261 AACAGCACAA AAGGAAACTC ACCCTAACTG TAAAGTAATT GTGTGTTTTG AGACTATAAA
4321 TATCCCTTGG AGAAAAGCCT TGTTTGCGTT TAGTGAACCG TCAGATGGTA CCGTTTAAAC
4381 TCGAGTGAGC GCAGCAACGA CCTGAAGATC GATCCGTAAA GCCACAGATG GGGTCGATCT
4441 TCAGGTCGTT GCTTCGCCTA CTAGAGCGGC CGCCACAGCG GGAGATCCA GACATGATAA
4501 GATACATTTT TGAATTCAG GCTATCCCAG GTTGCCTTGG TTCTTGGCAA TTGGGAAATT
4561 AAGAGGGCAG AGAGAATTTG AACAGAAACT GTTCTAATAT TGGTCTTTTA TTGTGTAAGT
4621 ATTGTTCTTT ggTAAACCTC CTTCTTTTgg TTTCCAGGAA TTGCTGGACA CAGTGGCTTG
4681 GTGTGTGTCT GAGGACTGTA GGCCTTGGCC CTAGGTTGTG GTTTTAGGTC TCAGGTGCTC
```

```
4741  TTCCTGGCTG TCTCCTTGCT TCTTTCCCTT GTCCTCTTCT TTGTTTCCAG CCTTTTCTCC
4801  CTTTTGCTTA AGTTTGGTGC AGCAGGGTTT GGCTGCTCTC AGATTCCTGC TTCCTCAGTT
4861  GCTGTAGTTG TCAGGCCCAG AAGGCTGGCA GAAGGATCAG GATCTGGCTA GGTTTGCTCT
4921  CACTGTGGCA GAGTAGGGGG AGGAGGAGAG CAAAAGTGAC CCCAGGCCAG CTGTAGGGAG
4981  CTTAGGCTTG GTCAAccAGC CTTCAGGTCC TAGACTTTGT CTTCTCTTGA GTTTGGCTGT
5041  GTGTGTTTGG TGggAACTAG GTTCTACTTA GCCCAAGAAA TTGGGCACTT TTTGCTTGTG
5101  GTTTCTGTAG AGAATTGCAC TGGGTATCTG ACTTAGCCTG GCAGCTTGCC TCCCTCAGGT
5161  AGGTTAGTCT CAGGAAGTGA AGCAAAGTCC AGCAAGAACT TCTTTTGTGG CTTAAAGTCT
5221  CAATTCTGTG AGGTGCTGGC AAATCACCAC CACAATCAAG AGGCTGAAGT GATTTTTGTC
5281  TAGGGAGGCA GGAAAGGCTT CCTGGAGTCA GCAGCCAGTA GGTGAAAGAG TAGATTGGAG
5341  ACCTTCTTAA TCTTCACAAC CTCTTGTCTC AAGGGGTGCC AGGAAGCTGT GGAGGCTGAA
5401  CCCTTCTTTT GCTGCCAGAG AGTGGGACAC CTTGAGGGTC AGGTCAAGGG GTTGTACCTT
5461  GTTTGGTAGA GAATTAGGGG CTCTTGAAGA CTTTGGTTGT GGTCAGGGGA GTGTATCTTT
5521  TAGGAAGAGT GACCAAGTGA GGAAGGGTAG AGGAGGACAG GTGGGAGGGA GTCCAGGTGG
5581  GAGTGAGTAG ACCCAGCAGG AGTGCAGGGC CTAAAGCCAG GTTGGTGGCA GGGCTGTGAG
5641  GAGAGGCAGC CACCTGTGTG TCTGAAGAAG CAGGGGCAAG AGGGAAGAGG CCAGCAGACT
5701  GCCTTCACCC AGAAACTGGA ATAGATTGTG AGAGACCTTT CCCTGCTCTT AGGAGGGGCT
5761  GAGTTccAGT ccTCTCTTGT TATACAAggg GCTTGGTATT TGTTTACAAA AggggTGTAA
5821  AGCTAgggCA AGGTTTGATA AGGCTTCTAG gggTATTTAA GAAGTATTGT TGgggTAATT
5881  GTTTGTCCAA TTAACTTTGC TCTTggAAGG ACTTTCAGTA CAAACTGCAA CAACAGGATT
5941  AGGAAgggAA AATTTCTGAG TTGgggTTAC TCCTCAGAAT TTCCCAGATT GTGATCTGGT
6001  TTTGATTTTC AAGCTTGCTG ACCCAATAGG TTAACCCACA AGTTTTAAcc AGACCTTCTC
6061  AGTCCACTTA CTTCAACTGC CCTTGCCAAA GTccAAGAGA TCTTAAACTG TTGTTTGGCA
6121  CAGCTTCCTC CCTCTTGGGT GGGCAAGCTT TTGGAAGAGA AGGCTCCTTT GGGTGAGAGT
6181  GGGGCACCAA AGTCTTCCCT GTCCCTTCCC CTAGCTTGAG AAGCCCTTCT CTATTGTGGA
6241  CTTTGTGCAA TTAGCTTAAT TACTAGCTTG AAGTTGACCT TCTGGAAATA CTTTCTGGTT
6301  TAGCCTCACA AGTGAGCAAG GAGGGTTGAG AGTTGTGCTG TGAGGATTGT GGGGCCCCAG
6361  CTGGCAGCAG GCTCTGGGTC AGGGGGGCAG GGACCAAAGG CTTACCTGAC AGTGAGGAGG
6421  GGTCTAGTAG GGGATCAGTT CCCCTGTTGT TCTTTAGAAc cTTCTGGATA TTCTTCTTcc
6481  cTGATTggGG GTTGTGAACA ATAGAATCAA CTTCTACTTG TAGATTGATT TAGGGAGAAC
6541  TTATACCTCA GTTGTTAAGT CACCCTGTCC AGATTGTGGG TTGCTTTCCT ATTTGTTCAG
6601  AACTTTcccA ATTACCTCAG AAGCACTTGA AATTTAAAGG ATTTTAAccc cAACTTAggG
6661  ATTATTTCAC TTAGCTCTTG CACTTTTCTT GATAATTGAA TCCTCAGGTA TTCCTCTGTT
6721  TggGTTACTA ATAGTTACTT CTTTTGGGgg ggTTTTCCCC TGAAAATCTT TTATCcccAA
6781  TTTGTGGCTT AcccTCTGAA GGTTGTTTGA TAATTTTGGA AGATTTGAAA GTCTTCTTAT
6841  TTTACAAGGT TTGGGGTCTC TTTAAGCTGC TTGGTTCTCT TGTCAGCTCC CAAAGCAGAA
6901  GAAAGCTAGC TGAAAATTGC AATAGAGAAG ATACTTCTTT TCCACCTGTT TTCAACTCTT
6961  ATCTTCTTGA ATTTCAGGGC ACCTTTCCTT GCTCCAGTG CTTGCTATCT GTTTATTATT
7021  TTCCTTCCTG AATACCCTGA ACTCCAGCTT GTTCTGCTGT AATTCTGGCC TCCCTGGCTT
```

-continued

```
7081  CTTGGACTCC TGTTTCCTTT GCTCTGTCTT CCCccAAGTC AGCTCCTGCT GAACAGCTTC
7141  TCAGCTGAAG TGAAccTGGA GTGCCTGGAT CTTGCTGGAT CTTTGAGTAT TGCCTCTGGg
7201  gTCCTTGGTT CCTTCTGCTG AGTTGCTCAG AATCTCCACT CCCCcaacCT TGTGTGGCCC
7261  TTCCTGCACT CCTCTGATTC CccTTGTCTT CCCTGGTTTC TTGCTTTGGT TTAAAGTCTC
7321  CACAGAACTT TTGCAGCTCT TCTGAAGACC TGGAAGCTTT TCTTCTTAA TTCTCTTCTC
7381  TTGACCTCTT TTCCCTTCTT TGAGAGCTAG AACTTCCCTT GGTGAACTTC TCTTTCCAGA
7441  ATTACTTGCC TTCTTTTCCC TCCCACTTAC CTGTTGTCCA GGAGAGGTCA GATTGCTGTG
7501  CTTATTGGAG GAGAACCCTT TCTTCCCTGG GCTCTTCTTC TCACTTGACT TCACCACTTC
7561  ACCTAATTCC TTGGACCCTC AGTGGTGTCA CTGCTGGATT TTTCTTTCCT TTGGCTGGCC
7621  TTAGGGCACA CCCAGGTTGA CTAGAATAGT CTTGGTATTT AGATCCACTC ACTTTTTCAG
7681  TTTCTGTGTC TGTCTCTTGC CTGCTTCTGA CTTAACCCAG AGAAAGCTTC TCTTTCACAA
7741  GGGTTCTTAG ATTTTTGTTC ACTGAGCACC TTCTTTTCTG AGGCAGTGTT TTACCAATAg
7801  gggTTTTCCT AGTCAGTCTA ACCTTACCTT TCTTGTTggG CTTGTCTTTG GTCCTGACCC
7861  TTTCTCTGAG TCTGTAAccc AGAATTGCTG TATAAcccAA TTACTTGAAA TCCTTTAGAA
7921  TCTTAACACT TCTTACACCT GATTTccccT TTTATTGTAT CCAAATTGAA CCAACCCTTT
7981  GTGAATTTGA CAGTGATTTC TCCCAGGGAT CCTAGTGTAT AAGGAATAGG ACTTAGTATT
8041  TTCTATTggg gGATATACCA CTTACCAGAT ACTGATTTTG TTGGACTTTT AACCCTTTTT
8101  TCTCTTTTTG AAAGAAAGTT AGGAATTATT TCTTCCAGTA GAACCAGTGT AACCTGAAAG
8161  CCTTTGAAAG AGTAGTTTgg GTATAGCTAT CTGAAAGGAA TTTCTTTCCA AgggATTTcc
8221  CCAGTGCTGA CAACAAACAA ACAGACACAC CCTGCAAGGT GAGTGTAAAG AACacTAGaG
8281  CAAGGCTACG TAGATAAGTA GCATGGCGGG TTAATCATTA ACTACAAGGA ACCCCTAGTG
8341  ATGGAGTTGG CCACTCCCTC TCTGCGCGCT CGCTCGCTCA CTGAGGCCGG GCGACCAAAG
8401  GTCGCCCGAC GCCCGGGCTT TGCCCGGGCG GCCTCAGTGA GCGAGCGAGC GCGCAGCTGC
8461  CTGCAGGTCT GAGACAATAA CCCTGATAAA TGCTTCAATA ATGTAAGCTT GTCGAGAAGT
8521  ACTAGAGGAT CATAATCAGC CATACCACAT TTGTAGAGGT TTTACTTGCT TTAAAAAACC
8581  TCCCACACCT CCCCCTGAAC CTGAAACATA AAATGAATGC AATTGAGGCC TTAATTCTAG
8641  CCATAAAAGG TCTTGAGCAG GCCGTTGAAA ACCTCAGCCG TATCAGCAAA ACGGCGGTGC
8701  CTGGTGCCGC CGCAATGACC ATTAACCGCG TTGCTTCATC CGCGATAGCG CAGTCGGCGT
8761  CACAGGTTGC CCGTGAGACA AAGGTACGCC GGAAACTGGT AAAGGAAAGG GCCAGGCTGA
8821  AAAGGGCCAC GGTCAAAAAT CCGCAGGCCA GAATCAAAGT TAGCCGGGGG GATTTGCCCG
8881  TAATCAAGCT GGGTAATGCG CGGGTTGTCC TTTCGCGCCG CAGGCGTCGT AAAAAGGGGC
8941  AGCGTTCATC CCTGAAAGGT GGCGGCAGCG TGCTTGTGGT GGGTAACCGT CGTATTCCCG
9001  GCGCGTTTAT TCAGCAACTG AAAAATGGCC GGTGGCATGT CATGCAGCGT GTGGCTGGGA
9061  AAAACCGTTA CCCCATTGAT GTGGTGAAAA TCCCGATGGC GGTGCCGCTG ACCACGGCGT
9121  TGAAACAAAA TAGTGAGCGG ATACGGCGTG AACGTCTTCC GAAAGAGCTG GGCTATGCGC
9181  TGAAGCATCA ACTCACACTG GTAATAAAGC GTAGAAACAT ACTGAACCTC CGTGCAGCCG
9241  TACTGGATGC ACTGGAGAAG CATGACACCG GGGCGACGTT TTTTGATGGT CGCCCCGCTG
9301  TTTTTGATGA GGCGGATTTT CCGGCAGTTG CCGTTTATCT CACCGGCGCT GAATACACGG
9361  GCGAAGAGCT GGACAGCGAT ACCTGGCAGG CGGAGCTGCA TATCGAAGTT TTCCTGCCTG
9421  CTCAGGTGCC GGATTCAGAG CTGGATGCGT GGATGGAGTC CCGGATTTAT CCGGTGATGA
```

```
9481 GCGATAGCCC GGCACTGTCA GATTTGATCA CCAGTATGGT GACCAGCGGC TATGACTACC
9541 GGCGCGACGA TGATGCGGGC TTGTGGAGTT CAGCCGATCT GACTTATGTC ATTACCTATG
9601 AAATGTCTCC ACGCTTATGA GCAGCAGACT CAACAGGACA AAAATCCGCA GCAGCAGAGC
9661 GATACCGAAG CGTCACGGCT GAAATATACC GAAGAGGCGC AGAAGGCTTA CGAACGGCTG
9721 AAGACGCCGC TGGAGAAATA TACCGCCCGT CAGGAAGAAC TGAACAAGGC ACTGAAAGAC
9781 GGGAAAATCC TGAAGGCGGA TTACAACACG CTGATGGCGG CGGCGAAAAA GGATTATGAA
9841 GCGACGCTGA AAAAGCCGAA ACAGTCCAGC GTGAAGGTGT CTGCGGGCGA TAGTCAGGAA
9901 GACAGTGCTC ATGCTGCCCT GCTGACGCTT CAGGCAGAAC TCCTGACGCT GGAGAAGCAA
9961 GCCGGAGCAA ATGAGAAAAT CAGCCAGCAG CGCCGGGATT TGTGGAAGGC GGAGAGTCAG
10021 TTCGCGGTAC TGGAGGAGGC GGCGCAACGT CGCCAGGTGT CTGCACAGGA GAAATCCCTG
10081 CTGGCGCATA AGATGAGAC GCTGGAGTAC AAACGCCAGG TGGCTGCACT TGGCGACAAG
10141 GTTAGGTATC AGGAGCGCCT GAACGCGCTG GCGCAGCAGG CGGATAAATT CGCACAGCAG
10201 CAACGGGCAA AACGGGCCGC CATTGATGCG AAAAGCCGGG GGCTGACTGA CCGGCAGGCA
10261 GAACGGGAAG CCACGGAACA GCGCCTGAAG GAACAGTATG GCGATAATCC GCTGGCGCTG
10321 AATAACGTCA TGTCAGAGCA GAAAAAGACC TGGGCGGCTG AAGACCAGCT TCGCGGGAAC
10381 TGGATGGCAG ACCTGAAGTC CGGCTGGAGT GAGTGGGAAG AGAGCGCCAC GGACAGTATG
10441 TCGCAGGTAA AAAGTGCAGC CACGCAGACC TTTGATGGTA TTGCACAGAA TATGGCGGCG
10501 ATGCTGACCG GCAGTGAGCA GAACTGGCGC AGCTTCACCC GTTCCGTGCT GTCCATGATG
10561 ACAGAAATTC TGCTTTAGCA GGCAATGGTG GGGATTGTCG GGAGTATCGG CAGCGCCATT
10621 GGCGGGGCTG TTGGTGGCGG CGCATCCGCG TCAGGCGGTA CAGCCATTCA GGCCGCTGCG
10681 GCGAAATTCC ATTTTGCAAC CGGAGGATTT ACGGGAACCG GCGGCAAATA TGAGCCAGCG
10741 GGGATTGTTC ACCGTGGTGA GTTTGTCTTC ACGAAGGAGG CAACCAGCCG GATTGGCGTG
10801 GGGAATCTTT ACCGGCTGAT GCGCGGCTAT GCCACCGGCG GTTATGTCGG TACACCGGGC
10861 AGCATGGCAG ACAGCCGGTC GCAGGCGTCC GGGACGTTTG AGCAGAATAA CCATGTGGTG
10921 ATTAACAACG ACGGCACGAA CGGGCAGATA GGTCCGGCTG CTCTGAAGGC GGTGTATGAC
10981 ATGGCCCGCA AGGGTGCCCG TGATGAAATT CAGACACAGA TGCGTGATGG TGGCCTGTTC
11041 TCCTGACCTC CACGATGAGG CGCGCCCAAT TGTTGTTGTT AACTTGTTTA TTGCAGCTTA
11101 TAATGGTTAC AAATAAAGCA ATAGCATCAC AAATTTCACA AATAAAGCAT TTTTTTCACT
11161 GCATTCTAGT TGTGGTTTGT CCAAACTCAT CAATGTATCT TATCATGTCT GGATCTGATC
11221 ACTGATATCG CCTAGGAGAT CCGAACCAGA TAAGTGAAAT CTAGTTCCAA ACTATTTTGT
11281 CATTTTTAAT TTTCGTATTA GCTTACGACG CTACACCCAG TTCCCATCTA TTTTGTCACT
11341 CTTCCCTAAA TAATCCTTAA AAACTCCATT TCCACCCCTC CCAGTTCCCA ACTATTTTGT
11401 CCGCCCACAG CGGGGCATTT TTCTTCCTGT TATGTTTTTA ATCAAACATC CTGCCAACTC
11461 CATGTGACAA ACCGTCATCT TCGGCTACTT TTTCTCTGTC ACAGAATGAA AATTTTTCTG
11521 TCATCTCTTC GTTATTAATG TTTGTAATTG ACTGAATATC AACGCTTATT TGCAGCCTGA
11581 ATGGCGAATG G
```

Example 2

RNAi directs sequence-specific gene silencing by double-stranded RNA (dsRNA) which is processed into functional small inhibitory RNAs (~21nt). In nature, RNAi for regulation of gene expression occurs primarily via small RNAs known as microRNAs (miRNAs). Mature microRNAs (~19-25 nucleotides) are processed from larger primary miRNA transcripts (pri-miRNAs) which contain stem-loop regions. Via a series of processing events catalyzed by the ribonucleases, Drosha and Dicer, the miRNA duplex region is liberated and a single strand (the antisense "guide" strand) is then incorporated into the RNA Induced Silencing Complex (RISC), thus generating a functional complex capable of base-pairing with and silencing target transcripts. The mode of target repression primarily depends upon the degree of complementarity; transcript cleavage typically requires a high-degree of base-pairing, whereas translational repression and mRNA destabilization occurs when small RNAs bind imperfectly to target transcripts (most often in the 3' UTR). Indeed for the latter, short stretches of complementarity—as little as 6 bp—may be sufficient to cause gene silencing.

Treatment of diseases of the central nervous system, e.g., inherited genetic diseases of the brain, remains an intractable problem. Examples of such are neurodegenerative diseases such as Spinocerebellar Ataxia Type 1 (SCA1, which is also called Ataxin-1).

Spinocerebellar ataxia 1 (SCA 1) is among a group of nine polyglutamine (polyQ) repeat/expansion diseases with no available treatment or cure. SCA 1 is characterized by cerebellar ataxia and neuronal degeneration in the cerebellum and brainstem. The incidence of SCA1 is approximately 1-2 per 100,000 people, indicating that there are ~3000-6,000 patients in the US alone. SCA1 is caused by an unstable CAG expansion in the ATXN1 gene, which encodes ataxin-1. Normally, a range of CAG repeats interspersed with 1-3 CATs are found in ATXN1. In SCA1 patients, the ATXN1 CAG repeat is greater than 39, conferring a toxic gain-of-function to ataxin-1 due to mutation.

Although clinical onset of SCA1 may occur from childhood through adulthood, most patients present between 30-40 years of age with progressive wide-based gait, difficulties with balance, speech, swallowing, coordination and spasticity. Extracerebellar dysfunction may also appear with increased deep tendon reflexes and oculomotor abnormalities. Mild cognitive impairment occurs in 10-20% of patients. Neuropathological studies of tissues from SCA1 patients show that the primary sites of degeneration are the dentate nucleus, the inferior olive and cerebellar Purkinje cells (PCs). There is more degeneration in the upper vermis, less severe in the lateral cerebellar cortex, and mild changes in the flocculonodular lobes. There is also involvement of brainstem nuclei and spinocerebellar tracts and variable reports of cerebral involvement. Ataxin-1 is ubiquitously expressed and is prevalent in cerebellar PCs. Tissues from SCA patients also show ataxin-1 positive nuclear inclusions in Purkinje cells and brainstem neurons and in cerebrum.

Animal studies have been pivotal to better define the cellular and molecular mechanisms underlying SCA1 pathogenesis. There is extensive evidence supporting the notion that the disease-causing mutation acts through a toxic gain of function mechanism, and that suppressing its expression would not only arrest disease progression, but may reverse disease phenotypes. Using a doxycycline-inducible transgenic mouse model for SCA1, Orr and colleagues showed that repressing mutant protein expression 12 weeks after sustained expression significantly improved pathology and behavioral deficits (Zu, T., L. A. Duvick, M. D. Kaytor, M. S. Berlinger, H. Y. Zoghbi, H. B. Clark and H. T. Orr (2004). "Recovery from polyglutamine-induced neurodegeneration in conditional SCA1 transgenic mice." J Neurosci 24(40): 8853-8861). Thus, a window of opportunity for gene silencing strategies, initiated after disease onset, may exist.

Gene silencing approaches include RNA interference (RNAi) (Xia, H., Q. Mao, S. L. Eliason, S. Q. Harper, I. H. Martins, H. T. Orr, H. L. Paulson, L. Yang, R. M. Kotin and B. L. Davidson (2004). "RNAi suppresses polyglutamine-induced neurodegeneration in a model of spinocerebellar ataxia." Nat Med 10(8): 816-820; Xia, H., Q. Mao, H. L. Paulson and B. L. Davidson (2002). "sRNA-mediated gene silencing in vitro and in vivo." Nat Biotechnol 20(10): 1006-1010), antisense oligonucleotides (Kole, R., A. R. Krainer and S. Altman (2011). "RNA therapeutics: beyond RNA interference and antisense oligonucleotides." Nat Rev Drug Discov 11(2): 125-140), inhibitory antibodies, and more recently DNA editing approaches ((Wood, A. J., T. W. Lo, B. Zeitler, C. S. Pickle, E. J. Ralston, A. H. Lee, R. Amora, J. C. Miller, E. Leung, X. Meng, L. Zhang, E. J. Rebar, P. D. Gregory, F. D. Urnov and B. J. Meyer (2011). "Targeted genome editing across species using ZFNs and TALENs." Science 333(6040): 307; Basu, S., A. Aryan, J. M. Overcash, G. H. Samuel, M. A. Anderson, T. J. Dahlem, K. M. Myles and Z. N. Adelman (2015). "Silencing of end-joining repair for efficient site-specific gene insertion after TALEN/CRISPR mutagenesis in *Aedes aegypti*." Proc Natl Acad Sci USA 112(13): 4038-4043; Ousterout, D. G., A. M. Kabadi, P. I. Thakore, W. H. Majoros, T. E. Reddy and C. A. Gersbach (2015). "Multiplex CRISPR/Cas9-based genome editing for correction of dystrophin mutations that cause Duchenne muscular dystrophy." Nat Commun 6: 6244). RNA interference (RNAi) is a naturally occurring process that mediates gene silencing and is currently being investigated as a therapy for dominant diseases such as SCA 1.

Previously, AAV vectors were used to deliver RNAi triggers to transgenic and knock-in mouse models of SCA 1 which provided improved neuropathological, motor phenotypes and transcriptional changes. Using this strategy, studies in non-human primates (NHPs) evaluating the biodistribution, safety and efficacy of vector delivery to the deep cerebellar nuclei (DCN) in NHPs have been completed.

Example 3

Methods and materials for the studies described in Examples 4-7.

Plasmids and Viral Vectors:

The therapeutic miRNA sequence targeting human and rhesus Ataxin-1 (miS1) has been described. (Keiser, M. S. et al. Neurobiol Dis 56, 6-13, doi:10.1016/j.nbd.2013.04.003 (2013)). The original therapeutic vector rAAV1.miS1.eGFP was modified to no longer express eGFP and instead contain a representative highly modified filler or stuffer sequence described in Example 1. Recombinant rAAV serotype 2/1 vectors (rAAV1 miS1 and rAAV1.miControl) were generated. AAV vectors were resuspended in Diluent Buffer and titers (viral genomes/ml) were determined by QPCR.

Cell Culture and Transfection:

HEK293 cells were transfected (Lipofectamine™ 2000) in quadruplicate in 24-well plates per manufacturer's instructions with 500 ng of plasmid containing pAAV.miS1.eGFP, pAAV.miS1, pAAV, or no plasmid. Total RNA was harvested 24 hours with TRIzol®.

Animals:

All animal protocols were approved by The Animal Care and Use Committee. Wild type FVB mice were obtained from Jackson Laboratories (Bar Harbor, Me.). B05 transgenic mice were previously provided by Dr. H. T. Orr and re-derived by Jackson Laboratories. The B05 line was maintained on the FVB background. Mice were genotyped using primers specific for the mutant human ataxin-1 transgene. (Burright, E. N. et al. Cell 82, 937-948 (1995)). Hemizygous and age-matched wildtype littermates were used for the indicated experiments. Treatment groups comprised of approximately equal numbers of male and female mice. Mice were housed in a controlled temperature environment on a 12-hour light/dark cycle. Food and water were provided ad libitum.

AAV Injections and Brain Tissue Isolation:

B05 mice were injected with rAAV1 vectors expressing miS1 or a control scrambled miRNA sequence (miC). Mice were stereotaxically injected bilaterally to the deep cerebellar nuclei (coordinates −6.0 mm caudal to bregma, ±2.0 mm from midline, and −2.2 mm deep from the cerebellar surface) with 4 µl of rAAV1 virus at doses of $1\times10^7$ vg, $1\times10^8$ vg, $6\times10^8$ vg, $1\times10^9$ vg, $6\times10^9$ vg or $1\times10^{10}$ vg/hemisphere or saline (Diluent Buffer). Mice were anesthetized with 4% isoflurane/oxygen mixtures and transcardially perfused with 20 ml of ice cold saline. For histological analyses, mice were sacrificed and brains removed and post-fixed overnight in 4% paraformaldehyde. Brains were stored in 30% sucrose/0.05% azide solution at 4° C. until cut on a sledge microtome at 40 µm thickness and stored at −20° C. in a cryoprotectant solution. For RNA and metabolite analyses, brains were removed and cerebellar hemispheres were flash frozen in liquid nitrogen and stored at −80° C. RNA was isolated from whole cerebellum using 1 ml of Trizol®, RNA quantity and quality were measured using a NanoDrop® 2000. For metabolite analysis, tissues were subjected to a perchloric acid extraction. Frozen samples were weighed and homogenized using beads in a TissueLyzer LT (Qiagen). Ice cold 3.6% $HClO_4$ was added, further homogenized and centrifuged at 4° C. Supernatant was buffered to a pH of ~7.0 with KOH, centrifuged, lyophilized and again weighed.

Immunohistochemical Analysis:

Free-floating sagittal cerebellar sections (40 µm thick) were washed in 1×TBS with 0.05% Triton®X-100 at room temperature and blocked for 1 hour in 5% serum, 0.05% Triton®X-100, in 1×TBS. Sections were incubated with primary antibody in 3% serum and 0.05% Triton®X-00 in TBS overnight at room temperature. Primary antibodies used were polyclonal rabbit anti-Calbindin (1:2000; Sigma), polyclonal anti-Iba1 (1:1000; WAKO), polyclonal anti-GFAP (1:2000; DAKO), and polyclonal rabbit 12NQ (1:1000; Orr Lab (Servadio, A. et al. Nat Genet 10, 94-98, doi:10.1038/ng0595-94 (1995))). For Fluorescent IHC, sections were incubated with goat anti-rabbit Alexa Fluor 488 or 568 (1:200; Life Technologies) in 3% serum and 0.05% Triton®X-100 in 1×TBS for 1 hour at room temperature. For DAB IHC, sections were incubated in goat anti-rabbit biotin-labeled secondary antibody (1:200; Jackson Immunoresearch) in 3% serum and 0.05% Triton®X-100 in 1×TBS for 1 hour at room temperature. Tissues were developed with Vectastain® ABC Elite Kit (Vector Laboratories), according to the manufacturer's instructions. All sections were mounted onto Superfrost Plus slides (Fischer Scientific) and cover-slipped with Fluoro-Gel (Electron Microscopy Sciences) or dehydrated and cover-slipped with DPX. Images were captured on a Leica DM6000B fluorescence microscope using LAS X software.

Semi-Quantitative PCR:

Reverse transcription (High Capacity cDNA Reverse Transcription Kit, Applied Biosystems) was performed on 1 µg total RNA collected from cerebellum using a standard stem-loop PCR primer designed to identify miS1 as described. (Keiser, M. S. et al. Neurobiol Dis 56, 6-13, doi:10.1016/j.nbd.2013.04.003 (2013)). sqRT-cDNA was subjected to RT-PCR with a standard reverse primer and a forward primer specific to miS1.

Quantitative PCR: Random-primer first-strand cDNA synthesis was performed using 2 µg total RNA (High Capacity cDNA Reverse Transcription Kit, Applied Biosystems) per manufacturer's instructions. Assays were performed on a BioRad CFX384 Real Time System using TaqMan® (Thermo-Fischer Scientific) primer/probe sets specific for human Ataxin-1, mouse Pcp2, mouse Grm1 or mouse β-Actin (TaqMan® 2× Universal Master Mix by Life Technologies).

$^1$H-magnetic resonance spectroscopy: Analysts were blinded to the treatment groups. NMR spectroscopy was performed at 400 MHz on a Bruker Avance III 400 widebore spectrometer. Each lyophilized tissue extract was dissolved in 0.4 ml of $D_2O$, the pH adjusted to 7.0 and the solution was introduced in a 5 mm NMR tube. An external standard made of a sealed capillary containing a solution of trimethylsilylpropionic acid (TSP) in $D_2O$ was centered in the NMR tube and used as chemical shift reference and quantitation standard. Fully relaxed proton spectra were acquired with a 5 mm proton probe. Standard acquisition conditions were as follows: PW 5 µs (45°) TR 8.84 s (AQ 4.84 s, D1 4 s), SW 6775 Hz, TD 64 k, 128 scans 4 DS. A soft water saturation pulse was applied during the 4 s relaxation delay.

Rotarod Analysis:

Mice were evaluated by a tester blinded to the treatment groups on an accelerated rotarod apparatus (model 47600; Ugo Basile). For distribution to groups of equal abilities at baseline, mice were first evaluated at 5 weeks of age prior to treatment. Mice were habituated to the rotarod for 4 min then subjected to three trials per day (with at least 30 min of rest between trials) for four consecutive days. For each trial, acceleration was from 4 to 40 rpm over 5 min, and then speed maintained at 40 rpm. Latency to fall (or if mice hung on for two consecutive rotations without running) was recorded for each mouse per trial. Trials were stopped at 500 seconds, and mice remaining on the rod at that time were scored as 500 seconds. Two-way analysis of variance followed by a Tukey post-hoc analysis was used to assess for significant differences. Variables were time and treatment.

Statistical Analysis:

For all studies, p values were obtained by using one-way analysis of variance followed by Tukey post-hoc analysis to assess for significant differences between individual groups. In all statistical analysis, P<0.05 was considered significant.

Example 4

Figure 1B:
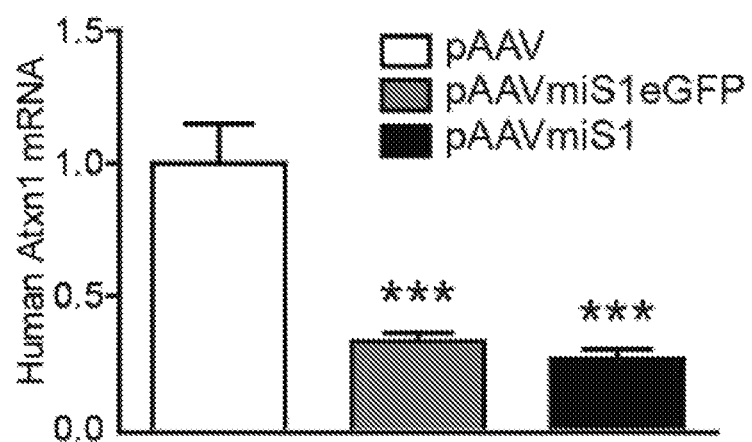

A representative highly modified filler or stuffer sequence described in Example 1 ensured appropriate length of the expression cassette for optimal AAV packaging (FIG. 1A). To confirm that this modification did not impact the silencing potency of the miRNA, HEK 293 cells were transfected with the shuttle plasmid pAAV.miS1.eGFP, pAAV.miS1 (having a representative highly modified filler or stuffer sequence described in Example 1) or a control plasmid. Compared to control transduced cells, both pAAV.miS1.eGFP and pAAV.miS1 significantly reduced ATXN1 mRNA expression 24 hours post-transfection (FIG. 1B); replacing eGFP with stuffer sequence did not alter the potency of the artificial miRNA.

Example 5

Using the representative vector comprising the highly modified filler or stuffer sequence described in Example 1, dosing studies in pre- and post-symptomatic mice to identify the lowest efficacious dose and the highest tolerated dose were then performed. Groups of presymptomatic mice were given 1 of 4 doses of AAV vector at 5 weeks of age and motor function assayed after symptom onset for untreated mice (34 weeks of age) and immediately sacrificed for post-necropsy analysis. A ceiling dose that conferred toxicity, a low dose that had no effect, and two doses that prevented phenotypic rotarod deficits relative to control injected SCA1 littermates were identified.

Figure 1C:
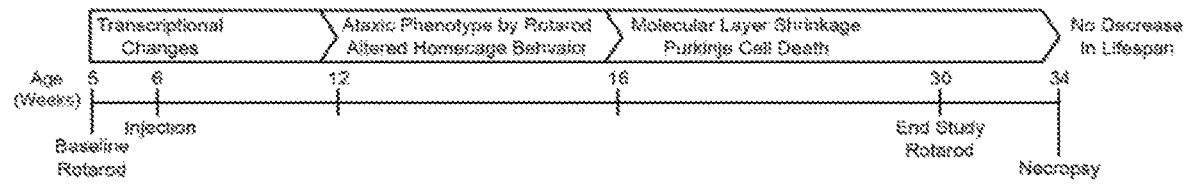

B05 transgenic mice show progressive disease, with transcriptional changes evident prior to noted behavioral deficits (FIG. 1C). To identify the efficacy and toxicity thresholds to prevent disease progression, mice were injected bilaterally into the DCN with increasing doses of rAAV1 miS1, rAAV1.miC or saline after baseline behavior testing (Table 1).

TABLE 1

Treatment Groups for Preventative Study

| Genotype | Injectate | Dose (vg) |
|---|---|---|
| B05 | rAAV1.miS1 | $8 \times 10^7$ |
| B05 | rAAV1.miS1 | $8 \times 10^8$ |
| B05 | rAAV1.miS1 | $8 \times 10^9$ |
| B05 | rAAV1.miS1 | $8 \times 10^{10}$ |
| B05 | rAAV1.miC | $8 \times 10^8$ |
| B05 | Saline | |
| Wildtype | | |

Figure 1D:
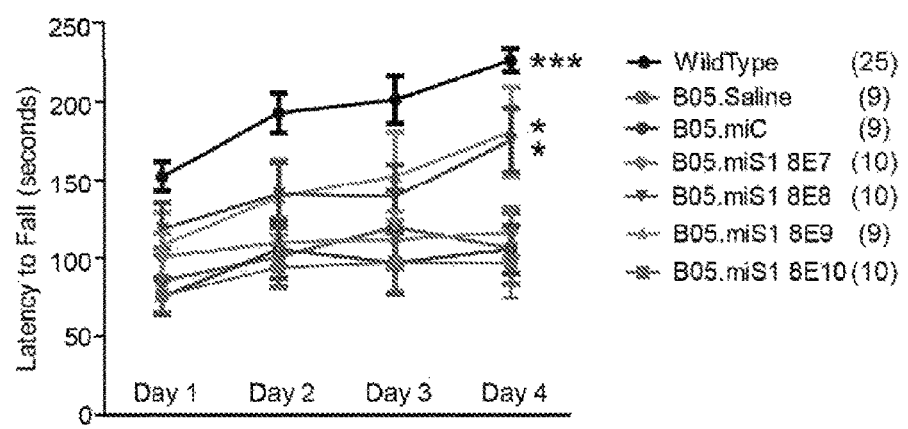

Twenty-four weeks after injection (30 weeks of age) animals were re-assayed by rotarod and then euthanized and tissues collected for post-necropsy analysis (FIG. 1C). As seen in FIG. 1D, at 30 weeks of age control treated transgenic mice could not remain on the rotarod apparatus after 98.8±22 seconds. B05 mice treated with rAAV1.miS1 at doses of $8 \times 10^8$ and $8 \times 10^9$ vg performed significantly better than control treated transgenic animals and were not statistically differently than their wildtype littermates.

Figure 2A:
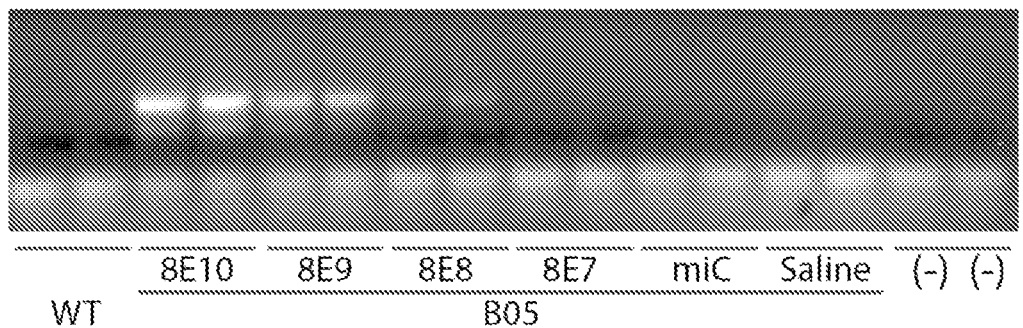
FIG. 2A-2C show sqPCR, qRT-PCR and NMR analyses of cerebellar extracts.
Figure 2B:
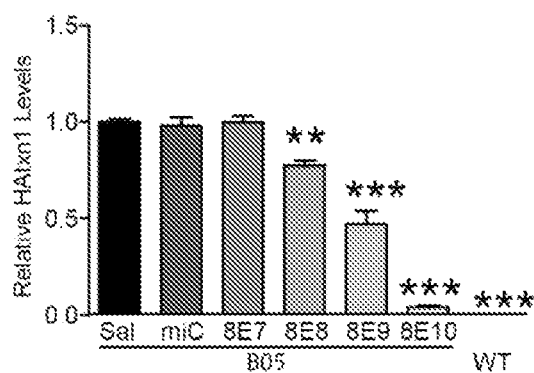

Semi-quantitative PCR on whole cerebellar lysates confirmed miS1 expression (FIG. 2A), with a clear dose-response. Quantitative RT-PCR for mutant human ATXN1 mRNA (FIG. 2B) showed a similar dose response that inversely correlated with miS1 levels. B05 mice treated with rAAV1.miC or rAAV1.miS1 at a dose of $8 \times 10^7$ vg had similar levels of ATXN1 mRNA (98±4% and 100±3% respectively) relative to saline-treated animals. B05 mice administered $8 \times 10^8$ or $8 \times 10^9$ vg of rAAV1.miS1 had increasingly reduced levels of ATXN1 mRNA (77±3 and 47±7%, respectively). B05 mice in the high dose group had almost complete reduction of human ATXN1 mRNA levels (4±1) relative to the control treated animals.

Figure 2C:
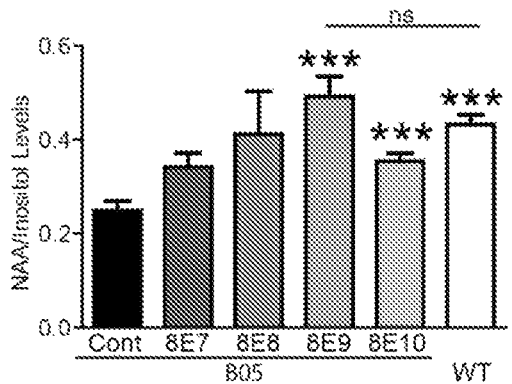

High field proton magnetic resonance spectroscopy ($^1$H MRS) allows quantitation of biomarkers in SCA1 patients in a non-invasive manner. SCA1 patients have reduced N-acetylaspartate (NAA) levels and elevated inositol levels, consistent with observations made in SCA1 mouse models. The levels of these metabolites in cerebellar lysates from all groups using nuclear magnetic resonance (NMR) were measured. Similar to results on untreated B05 mice (Oz, G. et al. J Neurosci 30, 3831-3838, doi:10.1523/JNEUROSCI.5612-09.2010 (2010)), control treated mice had reduced NAA/inositol ratios compared to wildtype littermates (FIG. 2C). However, this difference was normalized to wildtype levels in B05 mice treated with $8 \times 10^9$ or $8 \times 10^{10}$ vg of rAAV1.miS1 (FIG. 2C).

In SCA1, PC dendrites progressively retract, resulting in cerebellar molecular layer (ML) thinning. (Klement, I. A. et al. Cell 95, 41-53 (1998)). To evaluate a potential protective effect of rAAV1.miS1 on this phenotype, brain sections were evaluated by anti-calbindin staining of sagittal sections, and ML widths quantified. In control treated B05 animals, lobules III-IV/V have marked thinning, as do sections from animals injected with $8 \times 10^8$ vg of rAAV1 miS1 compared to wildtype littermates (FIG. 3A). However, there was no significant difference between the ML widths of wildtype animals and B05 mice treated with $8 \times 10^8$, $8 \times 10^9$, or $8 \times 10^{10}$ vg of rAAV1.miS1 In lobules IV/V-VI, all groups of B05 treated mice, except those treated with rAAV1 miS1 at $8 \times 10^9$ vg, were significantly reduced relative to their wildtype littermates (FIG. 3B).

Immunohistochemistry for human ATXN1 in PCs of control treated mice confirmed expression of the transgene in B05 but not wildtype mice (FIG. 3C). B05 mice treated with increasing doses of rAAV1.miS1 had progressively less ATXN1-positive PCs. At a dose of $8 \times 10^{10}$ vg, no ATXN1-positive PCs were detectable. Histological staining for glial fibrillary acidic protein (Gfap, a marker of astroglial activation), revealed enhanced immunoreactivity at the site of injection (the DCN) in all injected animals, and those treated at $8 \times 10^{10}$ vg had robust enhancement (FIG. 3D). Histological staining for Iba1, a marker for microglial activation, did not show differences among any experimental groups except for those receiving the highest dose of rAAV1 miS1 (FIG. 3E, F). Thus, rAAV.miS1 prevents cerebellar pathology.

Example 6

Two doses ($8 \times 10^8$ and $8 \times 10^9$ vg) were effective and non-toxic in the pre-onset treatment design. Because most patients with SCA1 present to the clinic with some disease manifestations, we tested the effects of miS1 therapy after disease onset. Using the representative vector comprising the highly modified filler or stuffer sequence described in Example 1, post-symptomatic mice were injected at 12 weeks of age at 5 escalating doses of AAV vector.

TABLE 2

Treatment Groups for Reversal Study

| Genotype | Injectate | Dose (total vg) |
|---|---|---|
| B05 | rAAV1.miS1 | $8 \times 10^8$ |
| B05 | rAAV1.miS1 | $2.6 \times 10^9$ |
| B05 | rAAV1.miS1 | $8 \times 10^9$ |
| B05 | rAAV1.miS1 | $2.6 \times 10^{10}$ |
| B05 | rAAV1.miS1 | $8 \times 10^{10}$ |
| B05 | rAAV1.miC | $8 \times 10^8$ |
| B05 | rAAV1.miC | $8 \times 10^9$ |
| B05 | Saline | |
| Wildtype | | |

Figure 4A:
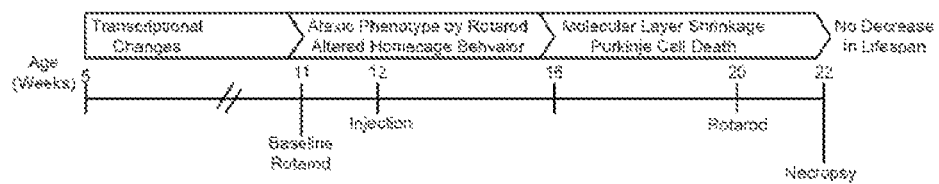
FIG. 4A-4C show experimental design of reversal study and rotarod data.

B05 mice have deficits on the rotarod by 10-11 weeks of age (FIG. 4A). B05 mice and wildtype littermates were baseline tested on the rotarod at 11 weeks, to confirm deficits (FIG. 4B), and then performed dosing studies as before, except that 5 doses (rather than 4) of rAAV1 miS1, or control were injected at 12 weeks of age. Additionally, the doses stepped up by ½ log and the lowest dose in the pre-disease onset treatment paradigm, which resulted in no silencing, was omitted (Table 2). End-study rotarod was conducted at 20 weeks of age (FIG. 4C) and 2 weeks later tissue collected for post-necropsy analysis.

Nine weeks after injection, wildtype mice performed significantly better than B05 mice receiving saline, control rAAV1.miC, and the low and two high dose groups. In contrast to wildtype mice, treated B05 mice in these groups had poorer performance relative to their baseline. However, B05 mice treated with $2.6 \times 10^9$ vg or $8 \times 10^9$ vg of rAAV1 miS1 performed significantly better than they did at 11 weeks of age, and also significantly better than the other B05 treatment groups. The data support the hypothesis that rAAV1.miS1 delivery into the DCN of symptomatic ataxic mice improves motor symptoms in the B05 model of SCA1, and is effective after disease onset. Thus, the AAV-mediated delivery of RNAi to the SCA 1 model can reverse motor impairment in mice, and is scalable to nonhuman primates, two important considerations in advancing this therapy to the clinic.

Figure 5A:
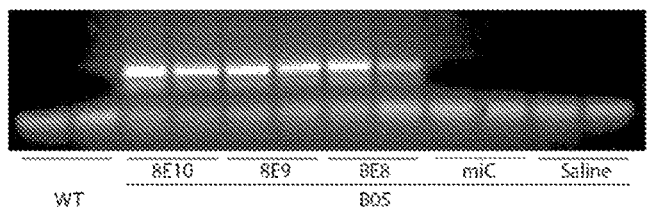
FIG. 5A-5E show sqPCR, qRT-PCR and NMR analyses of cerebellar extracts.
Figure 5B:
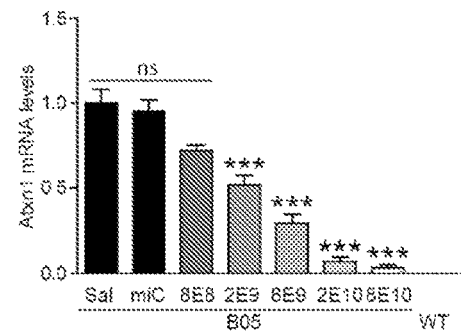
Figure 5C:
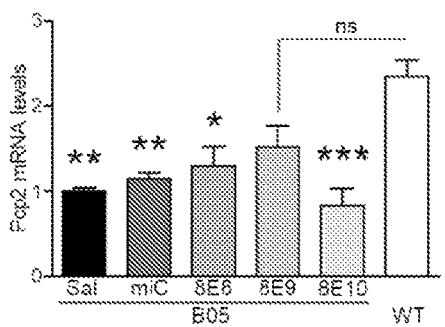
Figure 5D:
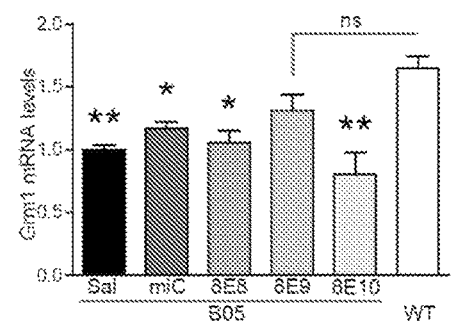
Figure 5E:
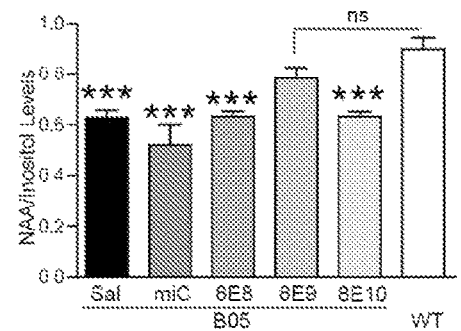

Example 7 miS1 expression was detected in B05 mice treated with rAAV1.miS1 (FIG. 5A), and there was a clear dose-dependent reduction of human ATXN1 mRNA levels in cerebellar lysates (FIG. 5B). ATXN1 mRNA levels were not different between B05 mice treated with saline, rAAV1.miC, and $8 \times 10^8$ vg rAAV1.miS1. B05 mice treated with $2.6 \times 10^9$ vg, $8 \times 10^9$, $2.6 \times 10^{10}$ or $8 \times 10^{10}$ vg of rAAV1.miS1 had progressively greater levels of knockdown relative to saline-treated B05 mice. rAAV1.miS1 therefore reduced ATXN1 levels in symptomatic B05 mice mRNA levels of Pcp2 and the metabotropic glutamate receptor type 1 (Grin1), two transcripts down-regulated in this model, were also evaluated (Serra, H. G. et al. Hum Mol Genet 13, 2535-2543, doi:10.1093/hmg/ddh268 (2004)); (Skinner, P. J. et al. Am J Pathol 159, 905-913, doi:10.1016/S0002-9440(10)61766-X (2001)). B05 mice treated with or rAAV1.miC had significantly lower levels of Pcp2 mRNA than wildtype littermates (FIG. 5C). Although B05 mice treated with $8 \times 10^8$ or $8 \times 10^{10}$ vg of rAAV1.miS1 had significantly lower levels of Pcp2, B05 mice given $8 \times 10^9$ vg of rAAV1.miS1 had Pcp2 levels that were not different from wildtype. Similar to Pcp2, significantly reduced Grm1 mRNA levels in control treated B05 mice or B05 mice treated with rAAV1.miS1 at $8 \times 10^8$ or $8 \times 10^{10}$ vg (FIG. 5D) was detected. Of note, SCA1 mice treated with $8 \times 10^9$ vg of rAAV1.miS1 expressed Grm1 at levels not significantly different from wildtype littermates. Consistent with the results (FIG. 2C), cerebellar lysates of control treated B05 mice had abnormal NAA/inositol ratios as measured by NMR that improved with treatment (FIG. 5E). B05 mice treated with $8 \times 10^9$ vg of rAAV1.miS1 had a NAA/inositol ratio that was not significantly different from their wildtype littermates. rAAV1.miS1 therefore improved molecular readouts in symptomatic B05 mice Sagittal sections were processed to quantify the molecular layer widths in medial cerebellar regions of lobules IV/V and VI. The data show marked thinning in control-treated B05 mice, and mice treated with $8 \times 10^8$ or $8 \times 10^{10}$ vg of rAAV.miS1 relative to those regions in wildtype mice (FIG. 6A). However, there was no significant difference between wildtype mice and B05 mice treated with $8 \times 10^9$ vg of rAAV1.miS1. ML widths in the caudal medial cerebellar sections between lobules VIII and IX also show significant thinning in control treated B05 mice and B05 mice administered $8 \times 10^{10}$ vg rAAV1.miS1 (FIG. 6B). B05 mice treated with $8 \times 10^8$ or $8 \times 10^9$ vg of rAAV1 miS1 had ML widths that were not significantly different from wildtype littermates.

Similar to the results observed in the pre-symptomatic dosing study, B05 mice treated with saline or rAAV1.miC are immunoreactive for human ATXN1 in most PCs. B05 mice treated post-symptomatically with rAAV1.miS1 show decreasing levels of ATXN1-positive PCs that correlate inversely to the dose injected (FIG. 6C). B05 mice treated with rAAV1 miS1 at $8 \times 10^8$ vg had fewer ATXN1-positive PCs than control treated mice; whereas those treated with rAAV1 miS1 at $8 \times 10^9$ or $8 \times 10^{10}$ have few to no detectable ATXN1-positive PCs. In the DCN, the site of injection, there were similar amounts of Gfap$^+$ immunoreactive cells in all sections, with the exception of enhanced immunoreactivity in B05 mice treated with $8 \times 10^{10}$ vg of rAAV1.miS1 (FIG. 6D). B05 mice treated with saline or rAAV1.miC showed slightly higher levels of Iba1 immunoreactivity in the cortex and DCN than those treated with $8 \times 10^8$ or $8 \times 10^9$ vg rAAV1.miS1, or wildtype mice. B05 mice treated with rAAV1.miS1 at $8 \times 10^{10}$ vg showed elevated Iba1 immunoreactivity in both the cortex and the DCN (FIG. 6E, F). rAAV1.miS1 therefore improved cerebellar pathology in symptomatic B05 mice.

Example 8

This foregoing studies provide solid evidence demonstrating that RNAi-mediated suppression of ATXN1 mRNA alters disease progression, reverses symptoms and normalizes cerebellar pathology and disease biomarkers in a SCA1 model. In addition, it identifies doses within the efficacy-toxicity window to guide clinical development of RNAi for the treatment of SCA1. The least effective dose, the toxicity threshold, and several effective doses that could either prevent or improve SCA1 readouts were identified.

Figure 4B:
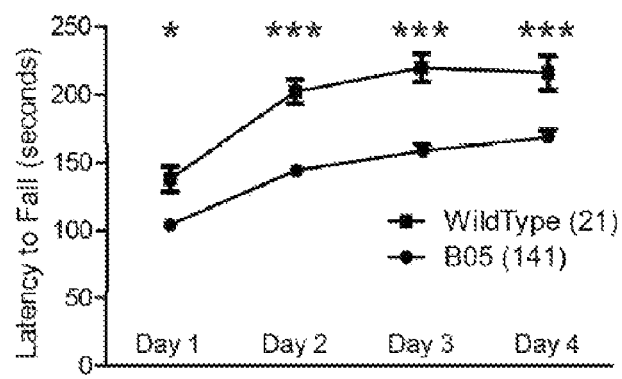
Figure 4C:
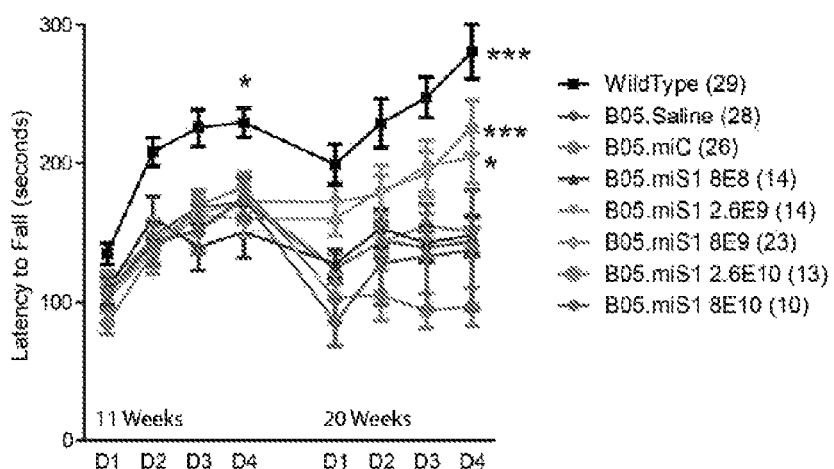

Cumulatively, the data in symptomatic mice extend earlier work demonstrating that eliminating mutant human ataxin-1 expression is therapeutic, even after cerebellar pathology and neurological deficits are evident. (Zu, T. et al. J Neurosci 24, 8853-8861, doi:10.1523/JNEUROSCI.2978-04.2004 (2004)); Oz, G. et al. Exp Neurol 232, 290-298, doi:10.1016/j.expneurol.2011.09.021 (2011)). In earlier reports, mutant ataxin-1 was completely eliminated and aggregates resolved quickly with recovery of cerebellar pathology. (Zu, T. et al. J Neurosci 24, 8853-8861, doi: 10.1523/JNEUROSCI.2978-04.2004 (2004)). The results herein are similar but contrast in significant ways. In particular, RNAi trigger expression, even when initiated after symptom onset, was therapeutic and improved symptomatology. The major difference is that the suppression was partial, and mutant ATXN1 was not suppressed in every Purkinje cell. However, this result is significant in that i) partial suppression even after disease onset can be beneficial; and ii) limiting coverage of the RNAi therapy to even a portion of the cerebellum, notably the medial regions, can improve behavioral outcomes. A rAAV vector dose of $2.6 \times 10^9$ vg had a 48% reduction of mutant ATXN1 mRNA, and a rAAV vector dose of $8 \times 10^9$ vg had ~71% reduction of mutant ATXN1 mRNA, and both provided benefit.

rAAV miS1 not only prevented further disease progression, but also improved disease readouts (e.g. see rotarod studies). At baseline, B05 animals were significantly impaired (FIG. 4B, C). After receiving miS1 at doses of $2.6 \times 10^9$ and $8 \times 10^9$ vg, rotarod performance at 20 weeks of age demonstrated a reversal of pre-existing impairment, and B05 mice performed no differently from their wildtype littermates. The difference between a 28% reduction in ATXN1 produced by $8 \times 10^8$ vg and a 48% reduction in ATXN1 produced by $2.6 \times 10^9$ vg of rAAV1.miS1 delineates the threshold for reversal of rotarod performance when delivered to post-symptomatic B05 mice. This is the first time that delivery of an RNAi vector has been shown to quantifiably reverse disease pathology in B05 SCA1 mice.

Of note, pre-symptomatic B05 mice receiving $8 \times 10^8$ vg at 6 weeks of age failed to develop the phenotypic rotarod deficit by 30 weeks of age, suggesting that earlier treatment with less viral load can be beneficial.

PC dysfunction occurs prior to cell loss in SCA1 and in SCA1 mice models. One measure of this is a reduction in molecular layer width due to PC dendritic retraction. The anterior lobe (rostral lobules) of the cerebellum is key to maintain balance, and dysfunction causes truncal ataxia. (Dale Purves, G. J. A. et al. Neuroscience. Third Edition edn, 439 (Sinauer Associates, Inc, 2004)). It is also a region affected early in the pathogenesis of SCA1. (Robitaille, Y. et al. Acta Neuropathol 90, 572-581 (1995)); (Robitaille, Y. et al. Brain Pathol 7, 901-926 (1997)). The posterior lobe (caudal) plays an important role in motor coordination. (Cicirata, F. et al. Brain Res Brain Res Rev 14, 117-141 (1989)). In mice that received $8 \times 10^8$ vg, molecular layer widths were similar in width to wildtype mice in caudal lobules, with measurable thinning in rostral lobules. However mice treated with $8 \times 10^9$ vg of rAAV.miS1 retained molecular layer widths similar to wildtype in both rostral and caudal lobules. This suggests that this dose, with scaling for human use, will provide preservation of both rostral and caudal aspects of the molecular layers providing improved balance and motor coordination respectively, as well as rescue motor symptoms.

In the B05 model, the transgene is expressed in the PCs only. However, assays for transduction efficiency, molecular readouts of efficacy, and transgene (miS1) levels were performed on whole cerebellar lysates. These data demonstrate the PC-targeting efficiency of this vector system. Molecular indicators of efficacy include Pcp2, the mRNA of which is trafficked to the dendrites, (Vassileva, G. et al. Brain Res Mol Brain Res 46, 333-337 (1997)). and Grm1, a metabotropic glutamate receptor 1 located in the post-synaptic termini of dendrites. (Vassileva, G. et al. Brain Res Mol Brain Res 46, 333-337 (1997)). The latter is important for coordinated motor function. (Knopfel, T. et al. Cerebellum 1, 19-26, doi:10.1007/BF02941886 (2002)). Both Pcp2 and Grm1 deficits were reversed in mice by 67% reduction in ATXN1.

B05 mice were reported to have increased Iba1+ immunoreactivity which is reversible in the SCA1 conditional model. (Cvetanovic, M. et al. Neuroscience 289, 289-299, doi:10.1016/j.neuroscience.2015.01.003 (2015)). The data show enhanced Iba1+ immunoreactivity in control treated B05 mice relative to WT animals, and qualitatively more in the $8 \times 10^{10}$ vg rAAV1.miS1 treatment group. In B05 mice treated with $8 \times 10^8$ or $8 \times 10^9$ vg, Iba1+ immunoreactivity was reduced. Thus, even a 28% reduction in ATXN1 ($8 \times 10^8$ vg dose), which does not result in behavioral rescue, can abate the phenotypic increase in Iba1+ signal.

Non-invasive biomarkers can provide tools for assessing efficacy in SCA1. High field proton magnetic resonance spectroscopy ($^1$H MRS) indicates that SCA1 patients have lower levels of N-acetylaspartate (NAA), and elevated levels of inositol. (Oz, G. et al. Mov Disord 25, 1253-1261, doi:10.1002/mds.23067 (2010)). These observations have been reproduced in transgenic SCA1 mice (Oz, G. et al. J Neurosci 30, 3831-3838, doi:10.1523/JNEUROSCI.5612-09.2010 (2010)). and were reversed in a conditional mouse model of SCA1. (Oz, G. et al. Exp Neurol 232, 290-298, doi:10.1016/j.expneurol.2011.09.021 (2011)). NAA reduction usually precedes neuronal loss, and is used as a marker of neuronal dysfunction. (Demougeot, C. et al. J Neurochem 77, 408-415 (2001)). The data herein reveal that NAA levels were modestly reduced in control treated SCA1 mice at 20 weeks of age, a time prior to significant PC loss. Importantly, mice treated with $8 \times 10^9$ vg of rAAV.miS1 had a NAA/inositol similar to their wildtype littermates. This indicates that the NAA/Inositol may be a sensitive, non-invasive measure of efficacy and a possible biomarker in disease-modifying clinical trials for SCA1.

Motor deficits quantified by the Scale for Assessment and Rating of Ataxia (SARA) correlate with altered neurochemical levels quantified by MRS. (Adanyeguh, I. M. et al. Mov Disord 30, 662-670, doi:10.1002/mds.26181 (2015)). A similar relationship is observed in untreated B05 mice, with improved "scores" upon treatment. These data therefore indicate that rAAV1 miS1 could provide therapeutic benefit and prevention of further pathogenesis in SCA1 patients. For example, if rAAV1.miS1 were administered prior to disease onset in patients. Furthermore, rAAV1.miS1 could halt or even reverse pre-existing motor deficits in early, symptomatic SCA1 patients. Thus, SARA scores could stabilize or improve with treatment, along with concomitant improvements in neurochemical levels.

In summary, the data demonstrate that AAV-mediated delivery of RNAi can reverse neuropathological phenotypes, transcriptional changes, and behavioral phenotypes in a mouse model of SCA1. Importantly, the minimal effective and maximally tolerated doses that will guide clinical application for SCA1 therapy appear to be identified. These studies are an important advance with application to other cerebellar diseases in which PCs, brainstem neurons and the DCN are important therapeutic targets.

What is claimed is:

1. An AAV vector filler or stuffer sequence comprising a nucleic acid from 500 to 5000 nucleotides in length and having at least 95% identity to SEQ ID NO:1.

2. The filler or stuffer sequence of claim 1, wherein the nucleic acid has at least 96% identity to SEQ ID NO:1.

3. The filler or stuffer sequence of claim 1, wherein the nucleic acid has 97% identity to SEQ ID NO:1.

4. The filler or stuffer sequence of claim 1, wherein the nucleic acid has 98% identity to SEQ ID NO:1.

5. The filler or stuffer sequence of claim 1, wherein the nucleic acid has 99% identity to SEQ ID NO:1.

6. The filler or stuffer sequence of claim 1, wherein the nucleic acid has 100% identity to SEQ ID NO:1.

7. A plasmid comprising the filler or stuffer sequence of claim 1, said plasmid comprising a selectable marker and/or an origin of replication.

8. A plasmid comprising SEQ ID NO:8.

9. The filler or stuffer sequence of any of claim 1, linked to heterologous nucleic acid sequence.

10. The filler or stuffer sequence of claim 1, linked to one or more AAV ITRs flanking the heterologous nucleic acid sequence, one or more AAV ITRs flanking the filler or stuffer sequence, a promoter, a poly-adenylation signal and/or an intron.

11. The filler or stuffer sequence of claim 9, wherein the heterologous nucleic acid sequence encodes or produces a therapeutic agent.

12. The filler or stuffer sequence of claim 11, wherein the sequence encoding or producing a therapeutic agent comprises a nucleic acid encoding a protein or an inhibitory nucleic acid, optionally flanked by a poly-Adenine sequence located 3' of the sequence encoding the therapeutic agent.

13. The filler or stuffer sequence of claim 12, wherein said inhibitory nucleic acid comprises a micro-RNA (miRNA), siRNA (small interfering RNA), trans-splicing RNA, antisense RNA or triplex forming RNA molecule.

14. The filler or stuffer sequence of claim 12, wherein said inhibitory nucleic acid comprises SEQ ID NO:3, or a sequence complementary thereto.

15. The filler or stuffer sequence of claim 12, wherein the protein comprises a growth factor, a cytokine, a blood clotting factor, or an immunoglobulin.

16. A recombinant adeno-associated virus (rAAV) vector comprising an AAV capsid protein comprising the filler or stuffer sequence of claim 1.

17. The rAAV vector of claim 16, wherein the AAV capsid is an AAV1, AAV2, AAV3, AAV4, AAV5, AAV6, AAV7, AAV8, AAV9, and/or AAV10 capsid protein, or a hybrid or chimera of any of the foregoing AAV capsids.

18. The plasmid comprising the filler or stuffer sequence of claim 7, wherein said selectable marker comprises an antibiotic resistance gene.

19. The filler or stuffer sequence of claim 1, wherein the nucleic acid has reduced CpG residues compared to SEQ ID NO:1.

* * * * *